The finding of inactivity in a given test is indicated by the letter I. All doses are expressed in milligrams per kilogram (mg./kg.).

| Example | Ach | Phen. | PPQ | BK | Tail Flick Agonist |
|---|---|---|---|---|---|
| 18A | 1.7 | I | — | — | 14 ± 2 |
| 18B | 0.3 | I | — | — | 6.9 ± 0.8 |
| 18C | 1.1 | — | — | — | 11 ± 1.0 |
| 18D | 7.4 | 24 | 64%/50 | — | I |
| 18H | 18 | I | — | 40%/10 | I/240 |
| 18M | 1.9 | I | — | — | 5.9 ± 0.95 |
| 18N | 0.89 | I | — | — | 2.0 ± 0.22 |
| 18P | 87%/75 33%/25 | 7.8 | — | — | I |
| 18Q | ~6.9 | I | — | — | 16%/120 14%/10 |
| 18S | 1.0 | I | — | — | 4.3 ± 0.52 |
| 18U | 53%/75 43%/25 7%/7.5 | I | — | — | I |
| 18V | 2.0 | I | — | 2.4 | 16 ± 3.3 |
| 18W | 60%/75 20%/25 | I | — | — | I |
| 18Y | 0.63 | I | — | — | 1.35 |
| 18Z | 11 | 21 | — | — | I |
| 18AA, 34B | 3.5 | — | — | — | 66%/120 |
| 18AB, 34D | 1.9 | I/80 | — | — | 16 |
| 18AC, 34F | ~1.3 | I/80 | — | — | 15 |
| 18AD, 34H | 11 | I/80 | — | — | 13%/120 |
| 18AE, 34L | 1.2 | I/80 | — | — | 31 |
| 18AF, 34K | 7.5 | I/80 | — | — | 70%/120 |
| 18AG, 34A | 1.3 | I/80 | — | — | 9.4 |
| 18AH | ~0.71 | I/1.0 | — | — | 2.6 |
| 18AJ, 34N | 10 | 26%/80 | — | — | 33%/240 12%/120 |
| 18AK, 34P (H$_2$SO$_4$) | 5.6 | I/80 | — | 28 | 16%/120 |
| 18AK (base) | 60%/75 47%/25 33%/10 | I/80 | — | — | I/240 |
| 18AL, 31A | ~0.22 | I/10 | — | — | 0.86 |
| 18AM, 34Q | 0.081 | I/10 | — | — | 0.28 |
| 18AN, 34R | 0.025 | I/0.1 | — | — | 0.18 |
| 18AP, 34S | 0.24 | I/0.1 | — | — | 0.46 |
| 18AQ, 34T | 0.90 | I/0.1 | — | — | 1.5 |
| 19B | 1.4 | I | — | 0.24 | 42 ± 21 |
| 19C | ~0.18 | I | — | — | 0.99 ± 0.14 |
| 19D | 0.023 | I | — | — | 0.099 ± 0.014 |
| 19E | 0.19 | I | — | — | 0.95 ± 0.11 |
| 19F(d,l-HCl) | 0.074 | 0.30 | 0.018 | 0.032 | 47%/240 |
| 19F(d-HCl) | 13%/10 27%/1.0 27%/0.5 | I | — | — | I |
| 19F(l-HCl) | 0.016 | ~0.088 | — | — | 9%/120 |
| 19F(d,l-CH$_3$SO$_3$H) | 0.049 | — | — | — | — |
| 19G | 12 | 0.04 | — | 2.2 | 16 |
| 19H(d,l-HCl) | 0.24 26(p.o) | 0.008 7.8(p.o.) | 0.28 | 0.043 | I |
| 19H(d,l-CH$_3$SO$_3$H) | 0.23 | — | — | — | — |
| 19H(l-CH$_3$SO$_3$H) | 0.74 0.19 | 0.005 | 0.052 | 0.022 | I/95 |
| 19H(d-CH$_3$SO$_3$H) | 6.3 ~11 | I/80 | 5.6 | I/50 | I/85 |
| 19H(napsylate) | 0.10 | ~2(i.p.) | — | — | — |
| 19J | 0.019 | I | — | — | 0.067 |
| 19K | 0.24 | I | — | — | 1.5 |
| 19L | 8.1 | 0.015 | — | 0%/10,50 | I |
| 19M(base) | 0.25 | — | — | 100%/0.5 | 70%/60 |
| 19M(CH$_3$SO$_3$H) | 0.17 | — | 0.21 | 0.19 | 2.5 |
| 19N | 4.2 | 0.42 | — | — | I/120 |
| 19R | 5.3 | 0.029 | — | — | I/120 |
| 19S | 0.15 | 1.1 | — | — | 13%/120 |
| 19U | 0.066 | 0.86 | — | — | 59%/120 36%/60 19%/30 |
| 19V | 60%/75 47%/25 | 0.012 | — | 0%/25 | I/100 |
| 19W | 0.0012 | — | — | — | 0.00135 |
| 19X | 0.0036 | I/0.001 | — | — | 0.0046 |
| 19Y | 0.011 | I/0.01 | — | — | 0.028 |
| 19Z | 1.3 | ~0.004 | — | 0.28 | I/120 |
| 19AA | 8.2 | 0.0052 | — | — | I/120 |

OCTAHYDRO-3,5-ETHENO- AND 3,5-ETHANOBENZO[G]QUINOLINES

RELATED APPLICATIONS

This is a division of my prior copending application Ser. No. 877,166, filed Feb. 13, 1978, now Pat. No. 4,180,667, patented Dec. 25, 1979 a continuation-in-part of my prior application Ser. No. 741,227, filed Nov. 12, 1976, now U.S. Pat. No. 4,100,164, patented July 11, 1978, which in turn is a continuation-in-part of my prior, now abandoned application Ser. No. 695,977, filed June 14, 1976, which in turn is a continuation-in-part of my prior, now abandoned application Ser. No. 576,313, filed May 12, 1975, which in turn is a continuation-in-part of my prior application Ser. No. 471,571, filed May 20, 1974, now U.S. Pat. No. 3,932,422, patented Jan. 13, 1976.

BACKGROUND OF THE INVENTION (a) Field of the Invention

This invention relates to 11(eq)-substituted-2,6-methano-3-benzazocines useful as analgesics and narcotic antagonists.

(b) Description of the Prior Art 2,6-Methano-3-benzazocines substituted in the 11-position with a lower-alkyl group are known. (See for example Gordon et al. U.S. Pat. No. 2,924,603, patented Feb. 9, 1960). Moreover, it is known that compounds in the 5,14-endo-etheno-and ethanotetrahydrothebaine and 6,14-endo-etheno- and ethano-tetrahydrooöripavine series having ketone, carbinol or lower-alkenyl groups at the 7-position thereof have unusual analgesic potency relative to morphine. [See Bentley et al., J. Am. Chem. Soc. 89, 3267–3292 (1967)]. Consequently there has been much interest in the field of analgesics in incorporating the ketone, carbinol or lower-alkenyl function present in the latter series at the 11-position of 2,6-methano-3-benzazocine-type analgesics, but all synthetic efforts in this direction have previously been unsuccessful.

SUMMARY OF THE INVENTION

In one of its composition of matter aspects, the invention relates to certain 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines, where Z is a ketone, carbinol or lower-alkenyl function and $R_1$, $R_2$, $R_2'$, $R_2''$, $R_2'''$, $R_3$ and $R_4$ are hydrogen, lower-alkyl or other organic groups more specifically defined hereinafter, which are useful as analgesics and narcotic antagonists.

In another composition of matter aspect, the invention relates to certain 6-$R_2''$-7-$R_2$-8-$R_2'$-9-$R_2'''$-1-$R_1$-2-Q-4aα-$R_3$-5α-$R_4$-1,2,3,4,4a,5,10,10a-octahydro-3,5-etheno- (and 3,5-ethano-)-benzo[g]quinolines useful as analgesics and narcotic antagonists.

In another composition of matter aspect, the invention relates to certain 2-$R_1$-3-(4-$R_2$-3-$R_2''$-$R_2'$-6-$R_2'''$-benzyl)-4-$R_3$-5-$R_4$-7-Y'-2-azabicyclo[2.2.2]oct-5-enes, where Y' is carboxy, cyano, carbo-lower-alkoxy or lower-alkanoyl, which are useful as intermediates for the preparation of the above-described octahydro-2,5-methanobenzo[g]quinolines and hexahydro-2,6-methano-3-benzazocines.

In one of its process aspects, the invention relates to a process for preparing certain 7-$R_2''$-8-$R_2$-9-$R_2'$-10-$R_2'''$-6(eq)-$R_4$-1,2,3,4,5,6-hexahydro-3-$R_1$11-(ax)-$R_3$-11(eq)-$CH_2Z$-2,6-methano-3-benzazocines comprising heating with formic acid in an inert organic solvent or with a benzyl-di-lower-alkylammonium formate or a tri-lower-alkylammonium formate certain 6-$R_2''$-7-$R_2$-8-$R_2'$-9-$R_2'''$-1-$R_1$-3-Y-4aα-$R_3$-5α-$R_4$-1,2,3,4,4a,5,10,10a-octahydro-2,5-methanobenzo[g]quinolines.

In another of its process aspects, the invention relates to a process for preparing certain 6-$R_2''$-7-$R_2$-8-$R_2'$-9-$R_2'''$-1-$R_1$-2-Q-4aα-5α-$R_4$-1,2,3,4,4a,5,10,10a-octahydro-3,5-ethenobenzo[g]quinolines comprising heating with formic acid in an inert organic solvent or with a benzyl-di-lower-alkylammonium formate or a tri-lower-alkylammonium formate certain 6-$R_2''$-7-$R_2$-8-$R_2'$-9-$R_2'''$-1-$R_1$-3-Y-4aα-$R_3$-5α-$R_4$-1,2,3,4,4a,5,10,10a-octahydro-2,5-methanobenzo[g]quinolines.

DETAILED DESCRIPTION INCLUSIVE OF THE PREFERRED EMBODIMENTS

More specifically this invention has, as its ultimate object, the obtainment of a new class of chemical compounds, useful as analgesics and narcotic antagonists, having the formula I:

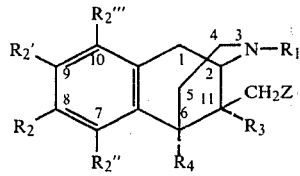

and chemically designated 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines.

The new 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines of formula I and other novel intermediates useful in their preparation are obtained according to my invention by novel reactions, including molecular rearrangements involving novel intermediates, according to the general reaction sequence as follows:

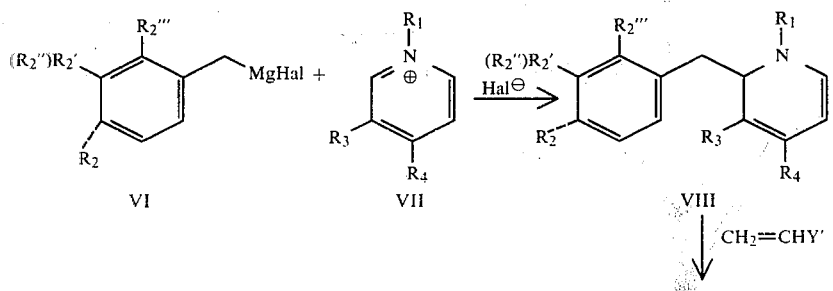

is hydrogen or lower-alkyl; or an acid addition salt thereof.

2. A compound having one of the formulas

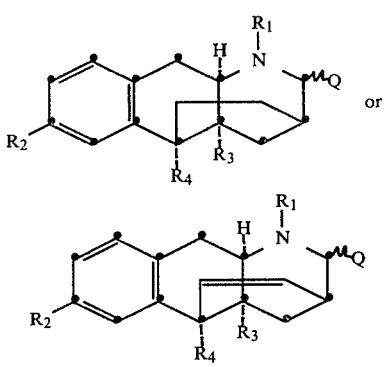

where $R_1$ is hydrogen, lower-alkyl, lower alkenyl, cycloalkyl-lower-alkyl, 2- or 3-furylmethyl, or such 2- or 3-furylmethyl substituted on the unsubstituted ring carbon atoms by from one to three methyl groups, or phenyl-lower-alkyl; $R_2$ is hydrogen, hydroxy or lower-alkoxy; $R_3$ is hydrogen or lower-alkyl; $R_4$ is lower-alkyl or lower-alkoxy-lower-alkyl or $R_3$ and $R_4$ together are divalent lower-alkylene, $-(CH_2)_n-$, where n is one of the integers 3 or 4; and Q is oxo, $H_2$ or CH-lower-alkyl or an acid addition salt thereof.

3. A compound according to claim 2 where Q is $H_2$.

4. A compound according to claim 2 where Q is CH-lower-alkyl.

5. A compound according to claim 2 wherein Q is oxo.

6. 7-Methoxy-5α-methyl-1,2,3,4,4a,5,10,10a-octahydro-3,5-ethenobenzo[g]quinoline according to claim 3.

7. 7-Methoxy-5α-methyl-1,2,3,4,4a,5,10,10a-octahydro-3,5-ethanobenzo[g]quinoline according to claim 3.

8. 7-Hydroxy-5α-methyl-1,2,3,4,4a,5,10,10a-octahydro-3,5-ethenobenzo[g]quinoline according to claim 3.

9. 1-Allyl-7-hydroxy-5α-methyl-1,2,3,4,4a,5,10,10a-octahydro-3,5-ethenobenzo[g]quinoline according to claim 3.

10. 1-(2-Phenylethyl)-7-hydroxy-5α-methyl-1,2,3,4,4a,5,10,10a-octahydro-3,5-ethenobenzo[g]quinoline according to claim 3.

11. 1-Allyl-7-hydroxy-5α-methyl-1,2,3,4,4a,5,10,10a-octahydro-3,5-ethanobenzo[g]quinoline according to claim 3.

12. 7-Hydroxy-5α-methyl-1-(2-phenylethyl)-1,2,3,4,4a,5,10,10a-octahydro-3,5-ethanobenzo[g]quinoline according to claim 3.

13. 7-Hydroxy-5α-methyl-1-propyl-1,2,3,4,4a,5,10,-10a-octahydro-3,5-ethenobenzo[g]quinoline according to claim 3.

14. 1-Cyclopropylmethyl-7-hydroxy-5α-methyl-1,2,3,4,4a,5,10,10a-octahydro-3,5-ethanobenzo[g]quinoline according to claim 3.

15. 7-Hydroxy-5α-methyl-1-propyl-1,2,3,4,4a,5,10,-10a-octahydro-3,4-ethanobenzo[g]quinoline according to claim 3.

16. 1,5α-Dimethyl-7-hydroxy-1,2,3,4,4a,5,10,10a-octahydro-3,5-ethenobenzo[g]quinoline according to claim 3.

17. 1,5α-Dimethyl-7-hydroxy-1,2,3,4,4a,5,10,10a-octahydro-3,5-ethanobenzo[g]quinoline according to claim 3.

18. 1,2-Dimethyl-5α-ethyl-1,2,3,4,4a,5,10,10a-octahydro-3,5-ethanobenzo[g]quinoline according to claim 4.

19. 1,2-Dimethyl-5α-ethyl-1,2,3,4,4a,5,10,10a-octahydro-3,5-ethanobenzo[g]quinoline according to claim 4.

20. 5α-Ethyl-1,2,4aα-trimethyl-1,2,3,4,4a,5,10,10a-octahydro-3,5-ethenobenzo[g]quinoline according to claim 4.

21. 1-Cyclopropylmethyl-5α-ethyl-2-methyl-1,2,3,4,4a,5,10,10a-octahydro-3,5-ethenobenzo[g]quinoline according to claim 4.

22. 7-Methoxy-5α-methyl-3,4,4a,5,10,10a-hexahydro-3,5-ethenobenzo[g]quinoline-2-(1H)-one according to claim 5.

23. A compound having one of the formulas

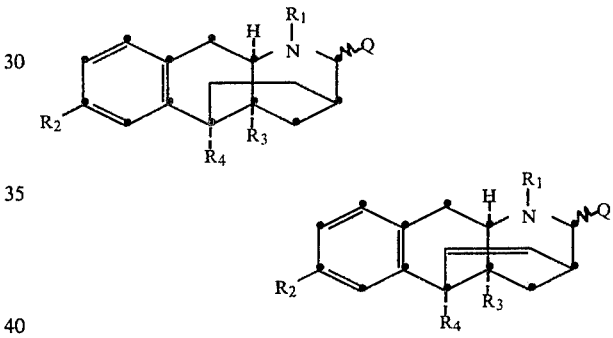

where $R_1$ is hydrogen, lower-alkyl, lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups or phenyl-lower-alkyl; $R_2$ is hydrogen, hydroxy or lower-alkoxy; $R_3$ is hydrogen or lower-alkyl; $R_4$ is lower-alkyl or lower-alkoxy-lower-alkyl, or $R_3$ and $R_4$ together are divalent lower-alkylene, $-(CH_2)_n-$, where n is one of the integers 3 or 4; and Q is CH—cycloalkyl or CH—phenyl or CH—lower-alkylphenyl substituted in the phenyl ring thereof by from one to two members of the group consisting of lower-alkyl, lower alkoxy, lower-alkylmercapto, trifluoromethyl or methylenedioxy attached to adjacent carbon atoms; or an acid addition salt thereof.

* * * * *

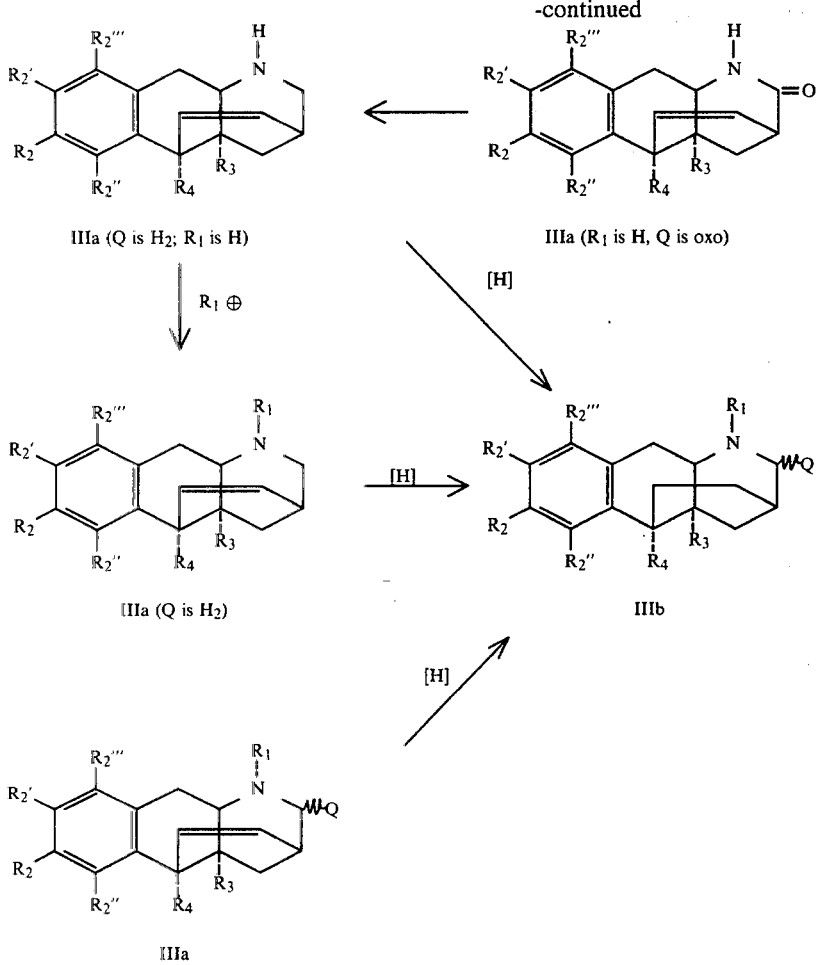

Thus the 7-$R_2''$-8-$R_2$-9-$R_2'$-10-$R_2'''$-6(eq)-$R_4$-1,2,3,4,5,6-hexahydro-3-$R_1$-11(ax)-$R_3$-11(eq)-$CH_2Z$-2,6-methano-3-benzazocines having the formula I are prepared via any of several methods from the intermediate 6-$R_2''$-7-$R_2$-8-$R_2'$-9-$R_2'''$-1-$R_1$-3-Y-3-$R_8$-4aα-$R_3$-5α-$R_4$-1,2,3,4,4a,5,10,10a-octahydro-2,5-methanobenzo[g]quinolines of formula II, which themselves are obtained from the 2-$R_1$-3-(4-$R_2$-3-$R_2''$ [or 5-$R_2$]-6-$R_2'''$-benzyl)-4-$R_3$-5-$R_4$-7-Y'-2-azabicyclo[2.2.2]oct-5-enes of formula IV which, in turn, are prepared according to standard procedures by reaction of a Grignard reagent derived from a 4-$R_2$-3-$R_2'$- (or $R_2''$)-2-$R_2'''$-benzyl halide of formula VI with a 3-$R_3$-4-$R_4$-1-$R_1$-pyridinium halide of formula VII and reaction of the resulting 1-$R_1$-2-(4-$R_2$-3-$R_2'$ [or $R_2''$]-2-$R_2'''$-benzyl)-3-$R_3$-4-$R_4$-1,2-dihydropyridine of formula VIII with a dienophile, $CH_2$=CHY'. The 6-$R_2''$-7-$R_2$-8-$R_2'$-9-$R_2'''$-1-$R_1$-2-Q-4aα-$R_3$-5α-$R_4$-1,2,3,4,4a,5,10,10a-octahydro-3,5-ethenobenzo[g]quinolines of formula IIIa are obtained along with certain compounds of formula I from the compounds of formula II where Y is $COR_5$ and $R_8$ is hydrogen, and the compounds of formula IIIa are also obtainable by rearrangement of a 3-(4-$R_2$-3-$R_2'$ [or 5-$R_2''$]-2-$R_2'''$-benzyl)-4-$R_3$-5-$R_4$-2-azabicyclo[2.2.2]-oct-5-ene-7-carboxylic acid ester of formula IV to a 1-$R_3$-2-(4-$R_2$-3-$R_2'$ [or 5-$R_2''$]-2-$R_2'''$-benzyl)-8-lower-alkylidene-3-azabicyclo[3.3.1]non-6-en-4-one of formula V and cyclization of the latter to a 6-$R_2''$-7-$R_2$-8-$R_2'$-9-$R_2'''$-2-oxo-4aα-$R_3$-5α-$R_4$-1,2,3,4,4a,5,10,10a-octahydro-3,5-ethenobenzo[g]quinoline having the formula IIIa. The compounds of formula IIIa can be catalytically reduced to the 6-$R_2''$-7-$R_2$-8-$R_2'$-9-$R_2'''$-1-$R_1$-2-Q-4aα-$R_3$-5α-$R_4$-1,2,3,4,4a,5,10,10a-octahydro-3,5-ethanobenzo[g]quinolines of formula IIIb.

In the final products and intermediates depicted in the above reaction sequences:

$R_1$ is hydrogen, lower-alkyl, lower-alkanoyl only when $R_4$ is hydrogen, lower-alkenyl, lower-alkynyl, halo-lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups, phenyl-lower-alkyl, or phenyl-lower-alkyl substituted in the phenyl ring by from one to two members of the group consisting of halogen (including bromine, chlorine and fluorine), lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms;

$R_2$, $R_2'$, $R_2''$ and $R_2'''$ are each hydrogen, or three of them are hydrogen and the fourth is halogen (including bromine, chlorine or fluorine), lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or two of the adjacent such groups together are methylenedioxy.

$R_3$ is hydrogen or lower-alkyl;

$R_4$ is hydrogen, lower-alkyl, lower-alkoxy-lower-alkyl, hydroxy-lower-alkyl, lower-alkylthio-lower-alkyl, lower-alkylsulfinyl-lower-alkyl, phenylthio-lower-alkyl, phenylsulfinyl-lower-alkyl, lower-alkenyl or halo-lower-alkyl, or $R_3$ and $R_4$ together are divalent lower-alkylene, —$(CH_2)_n$—, where n is one of the integers 3 or 4;

$R_4'$ is hydrogen or lower-alkyl;

Z is one of the groups

or the ethylene glycol ketal or the oxime or O-carboxymethyloxime (=NOCH$_2$COOH) thereof,

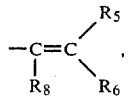

or a group of the formula:

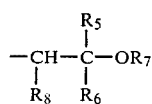

where $R_5$ and $R_6$ are the same or different hydrogen, lower-alkyl, cycloalkyl, cycloalkyl-lower-alkyl, phenyl, phenyl-lower-alkyl, or phenyl or phenyl-lower-alkyl substituted in the phenyl ring by from one to two members of the group consisting of lower-alkyl, /lower-alkoxy, lower-alkyl-mercapto, trifluoromethyl or methylenedioxy attached to adjacent carbon atoms;

$R_7$ is hydrogen, lower-alkanoyl, benzoyl, or benzoyl substituted by from one to three members of the group consisting of lower-alkyl, lower-alkoxy, hydroxy, halo (including chlorine, bromine and fluorine) or trifluoromethyl;

$R_8$ is hydrogen or lower-alkyl;

$R_9$ is lower-alkyl, cycloalkyl-lower-alkyl or phenyl-lower-alkyl;

Q is oxo(=O), H$_2$, CH-lower-alkyl, CH-cycloalkyl, CH-lower-alkylcycloalkyl, CH-phenyl, CH-lower-alkylphenyl, or the latter two groups substituted in the phenyl ring by from one to two members of the group consisting of lower-alkyl, lower-alkoxy, lower-alkyl-mercapto, trifluoromethyl or methylenedioxy attached to adjacent carbon atoms;

Y is carboxy, cyano, carbo-lower-alkoxy, COR$_5$, COO-lower-alkylene-cycloalkyl, COO-lower-alkylene-phenyl, or a group of the formula:

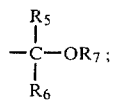

$Y'$ is carboxy, cyano, carbo-lower-alkoxy, COO-lower-alkylene-cycloalkyl, COO-lower-alkylene-phenyl or lower-alkanoyl; and Hal is halogen.

As used herein, the terms lower-alkyl or lower-alkoxy mean saturated, acyclic groups which may be straight or branched containing from one to about seven carbon atoms as exemplified by methyl, ethyl, propyl, isopropyl, butyl, nonadjacent t-butyl, methoxy, ethoxy, propoxy, isopropoxy, or t-butoxy.

As used herein, the terms lower-alkenyl, halo-lower-alkenyl and lower-alkynyl represent monovalent groups of from three to seven carbon atoms containing one double or triple bond as illustrated, for example, by 1-propenyl, 2-butenyl, 4-pentenyl, 3-methyl-2-butenyl, 1-methyl-2-propenyl, 2-methyl-2-propenyl, 2-propynyl, 2-butynyl, 4-pentynyl, 2-hexynyl, and the like. The term halo-lower-alkenyl includes, for example, 2-chloroethenyl, 2-bromoethenyl, 3,3-dichloro-2-propenyl, 1-bromo-2-methylpropenyl, and the like.

As used herein, the term cycloalkyl means saturated carbocyclic groups containing from three to seven ring carbon atoms as illustrated, for example, by cyclopropyl, cyclobutyl, cyclopentyl, cyclohexyl, 2-methylcyclobutyl, 4-ethylcyclohexyl, and the like.

As used herein, the term lower-alkanoyl means such groups derived from saturated, aliphatic monocarboxylic acids having from one to four carbon atoms, as illustrated, for example, by formyl, acetyl, propionyl, butyryl, isobutyryl, and the like.

As used herein, the term lower-alkylene means a saturated, divalent radical, which can be straight or branched, and having from one to four carbon atoms, as illustrated, for example, by methylene [—CH$_2$—], 1,2-ethylene [—CH$_2$CH$_2$—], 1,3-propylene [—CH$_2$CH$_2$CH$_2$—], 1,2-(1-methylethylene) [—CH(CH$_3$)CH$_2$—], 1,4-butylene [—CH$_2$CH$_2$CH$_2$CH$_2$—], and the like.

As determined by standard pharmacological test procedures to be described hereinafter, the compounds of formula I and certain species of formula II have been found to have useful analgesic activity, and as disclosed following Example 42B infra, some compounds of formula I have also been found to have useful narcotic antagonist activity. The compounds of formula I are thus useful as analgesic agents and narcotic antagonists, and certain species of formula II are useful as analgesic agents. The compounds of formula III have also been found to have analgesic activity and are thus useful as analgesic agents.

Preferred compounds within the ambit of formula I are those where Z is the group CH$_2$COR$_5$ where R$_5$ is lower-alkyl, cycloalkyl-lower-alkyl or phenyl-lower-alkyl, and R$_1$, R$_2$, R$_2'$, R$_2''$, R$_2'''$, R$_3$ and R$_4$ have the meanings given above, and particularly preferred compounds are those of the latter type where R$_1$, R$_3$ and R$_4$ are each lower-alkyl; R$_2$ is hydroxy; and R$_2'$, R$_2''$ and R$_2'''$ are each hydrogen.

In accordance with the above general description, the 7-R$_2''$-8-R$_2$-9-R$_2'$-10-R$_2'''$-6(eq)-R$_4$-1,2,3,4,5,6-hexahydro-3-R$_1$-11(ax)-R$_3$-11(eq)-CH$_2$Z-2,6-methano-3-benzazocines of formula I where Z is

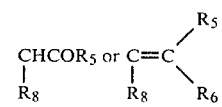

and R$_1$, R$_2$, R$_2'$, R$_2''$, R$_2'''$, R$_3$, R$_4$, R$_5$, R$_6$ and R$_8$ have the meanings given above are prepared by heating, with formic acid in an organic solvent, for example toluene, xylene or mesitylene, or with a benzyl-di-lower-alkylammonium or a tri-lower-alkylammonium formate at a temperature in the range from 120°–150° C., a 6-R$_2''$-7-R$_2$-8-R$_2'$-9-R$_2'''$-1-R$_1$-3-Y-3-R$_8$-4aα-R$_3$-5α-R$_4$-1,2,3,4,4a,5,10,10a-octahydro-2,5-methanobenzo[g]quinoline of formula II where R$_8$ is hydrogen and Y is either COR$_5$ (to give the compounds of formula I where Z is CH$_2$COR$_5$) or the group:

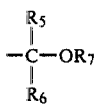

where R$_7$ is hydrogen (to give the compounds of formula I where Z is

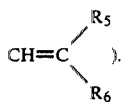).

A preferred solvent is mesitylene. The compounds of formula II where Y is COR$_5$ or the group

where R$_7$ is hydrogen are thus intermediates for preparing the compounds of formula I where Z is, respectively, the groups —CH$_2$COR$_5$

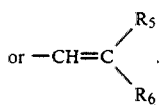

The compounds of formula I where R$_5$ is benzyl (or benzyl substituted in the phenyl ring thereof by the substituents enumerated above) and R$_1$, R$_2$, R$_2'$, R$_2''$, R$_2'''$, R$_3$, R$_4$, R$_6$ and R$_8$ have the meanings given above can also be prepared by reaction of a lower-alkyl β-[-7-R$_2''$-8-R$_2$-9-R$_2'$-10-R$_2'''$-6(eq)-R$_4$-1,2,3,4,5,6-hexahydro-3-R$_1$-11(ax)-R$_3$-2,6-methano-3-benzazocin-11(eq)-yl]-propionate of formula Ia with an alkali metal salt of phenylacetic acid (or a phenylacetic acid substituted in the phenyl ring thereof), the latter prepared by reaction of the desired phenylacetic acid with two molar equivalents of an alkali metal amide, followed by hydrolysis and simultaneous decarboxylation of the resulting condensation product. The method is illustrated by the reaction using unsubstituted phenylacetic acid:

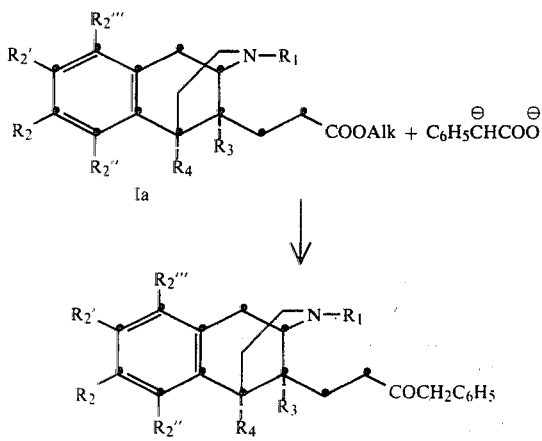

where Alk represents lower-alkyl. The esters of formula Ia and the method for their preparation are disclosed in Lewis and Michne U.S. Application Ser. No. 818,713, filed July 25, 1977, now U.S. Pat. No. 4,119,628 patented Oct. 10, 1978 and c.i.p. thereof Ser. No. 878,308, filed Feb. 16, 1978, now U.S. Pat. No. 4,148,794, patented Apr. 10, 1979, which applications are more fully described below.

The oximes or O-carboxymethyloximes of the compounds of formula I where Z is

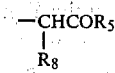

are prepared by reacting the latter with hydroxylamine or O-carboxymethylhydroxylamine in an inert organic solvent, for example a lower-alkanol. The reaction is carried out by heating the reactants in the solvent at the reflux temperature of the latter.

The compounds of formula I where Z is

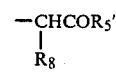

where R$_8$ is lower-alkyl, are prepared by treatment of the compounds of formula IIB, where R$_8$ is hydrogen and Y is a proton activating group, i.e. an ester or keto (COR$_5$) group, with a strong base, for example a lithium di-lower-alkylamide, a preferred base being lithium diisopropylamide, and reaction of the resulting lithium salt with a lower-alkyl ester of a strong mineral acid, for example a lower-alkyl halide or a di-lower-alkyl sulfate. The ester or keto group Y in the compounds of formula IIA thus obtained can then be converted to other groups, for example

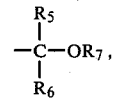

before conversion of the latter to the compounds of formula I where Z is

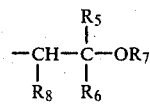

and R$_8$ is lower-alkyl by heating the compounds of formula II where R$_8$ is lower-alkyl with formic acid in an organic solvent or with a benzyl-di-lower-alkylammonium or tri-lower-alkylammonium formate as described above.

As indicated in the above reaction sequence, alkylation of the compounds of formula IIB via the lithium salt results in epimerization of the Y group. It had been previously thought that the group Y in the compounds of formula IIB as obtained by cyclization of the compounds of formula IV possesses the β-configuration, i.e. the group Y is cis to the 2,5-methano bridge (vide infra), and such steric configuration of the group Y is disclosed in Sterling Drug Inc.-owned Japanese Provisional Patent Publication No. 160,275, published Dec. 26, 1976 from Japanese patent appln. No. 60,111/75, filed May 20, 1975 as well as in U.S. Pat. No. 3,932,422, patented Jan. 13, 1976 on application Ser. No. 471,571, filed May 20, 1974 and on which Japanese appln. No. 60,111/75 was based. However, since the time of preparation and filing of the Japanese application on which the patent publication is based, some uncertainty has developed over whether the group Y has the α- or β-configuration. In any event, alkylation of the compounds of formula IIB via the lithium salt results in epimerization of the group Y, and in fact, the compounds of formula IIA where R₈ is hyrogen and the Y group is in either the α- or the β-configuration can be prepared from the respective β-Y or α-Y compounds by treatment first with a strong base and then with acid. In view of the fact that either of the groups Y and R₈ in the compounds of formulas IIA and IIB, respectively, can occupy either the α- or the β-configuration, the compounds of formulas IIA and IIB can be generally represented by the formula:

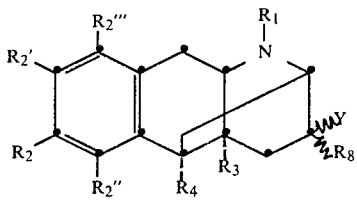

II where R₈ is hydrogen or lower-alkyl.

Insofar as the structures of the 2,6-methano-3-benzazocines of formula I are concerned, the question of the steric configuration at the 3-position of the compounds of formula II is moot, because the asymmetry at the 3-position is destroyed on conversion of the compounds of formula II to the compounds of formula I, and the compounds of formula II having both possible steric configurations at the 3-position are fully operable for the preparation of the compounds of formula I.

Insofar as the steric configuration of the group Q in the compounds of formula IIIa is concerned, a study of molecular models of hypothetical reaction intermediates indicates that the group Q probably has the β-configuration, i.e. Q is cis to the 3,5-etheno bridge, but the configuration has not been rigorously established.

The compounds of formula I where Z is the group:

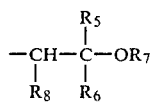

where R₇ is hydrogen and R₅, R₆ and R₈ have the meanings given above are prepared from the corresponding compounds where Z is the group

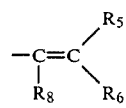

by hydroxylation of the latter, for example with concentrated sulfuric acid and hydrolysis of the resulting hydrogen sulfate ester. The compounds of formula I where Z is the group

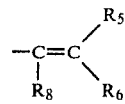

are thus intermediates for the carbinols of formula I.

The compounds of formula I where Z is the group

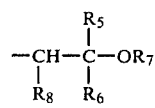

where each of R₆ and R₇ is hydrogen and R₅ and R₈ have the meanings given above are prepared by selective reduction of the corresponding compounds where Z is

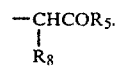

When R₅ is hydrogen the selective reduction is carried out with an alkali metal aluminum hydride in an inert organic solvent such as dioxane, tetrahydrofuran or diethyl ether at temperatures in the range from about 0° C. to 100° C. When R₅ is lower-alkyl, cycloalkyl-lower-alkyl, phenyl or phenyl-lower-alkyl, the reduction is carried out with an alkali metal borohydride in an inert organic solvent, for example lower-alkanols, such as methanol, ethanol or isopropanol.

The compounds of formula I where Z is

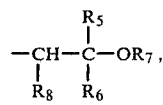

R₅ and R₆ are each lower-alkyl, cycloalkyl, cycloalkyl-lower-alkyl, phenyl, phenyl-lower-alkyl, or substituted-phenyl or phenyl-lower-alkyl, R₇ is hydrogen and R₈ is hydrogen or lower-alkyl are prepared by reaction of the corresponding compounds where Z is

where R₅ is lower-alkyl, cycloalkyl, cycloalkyl-lower-alkyl, phenyl, phenyl-lower-alkyl or substituted-phenyl or phenyl-lower-alkyl with one molar equivalent of an appropriate organo lithium, R₆Li, where R₆ has the meanings given above. The reaction is carried out in an inert organic solvent such as benzene or toluene. In this manner compounds where R₅ and R₆ are either the same or different lower-alkyl, cycloalkyl, cycloalkyl-lower-alkyl, phenyl, phenyl-lower-alkyl, or substituted phenyl or phenyl-lower-alkyl groups can be prepared depending upon the identity of the R₅ group and the choice of the particular organo lithium.

The compounds of formula I where Z is

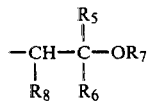

$R_5$ and $R_6$ are each hydrogen or the same or different lower-alkyl, cycloalkyl, cycloalkyl-lower-alkyl, phenyl, phenyl-lower-alkyl or substituted phenyl or phenyl-lower-alkyl, $R_8$ has the meanings given above, and $R_7$ is lower-alkanoyl, benzoyl or substituted-benzoyl are prepared by esterification of the corresponding compounds where $R_7$ is hydrogen, for example with an appropriate acid halide, anhydride or other acylating agent. The reaction is advantageously carried out using an appropriate acid halide in a pyridine solvent which serves as an acid acceptor to take up the hydrogen halide split out during the course of the reaction.

The compounds of formula I where $R_1$ is lower-alkenyl, lower-alkynyl, halo-lower-alkenyl or 2- or 3-furylmethyl (or such 2- or 3-furylmethyl substituted by from one to three methyl groups) are advantageously prepared from the corresponding compounds where $R_1$ is hydrogen by reaction of the latter with an appropriate lower-alkenyl halide, lower-alkynyl halide or halo-lower-alkenyl halide, as the case may be, in an inert organic solvent, for example a lower-alkanol, acetone or dimethylformamide (hereinafter designated DMF), in the presence of an acid-acceptor, for example an alkali metal carbonate or bicarbonate. A preferred solvent is DMF.

The compounds of formula I where $R_2$, $R_2'$, $R_2''$ or $R_2'''$ is lower-alkanoyloxy are advantageously prepared from the corresponding compounds where $R_2$, $R_2'$, $R_2''$ and $R_2'''$ is hydroxy by esterification with an appropriate lower-alkanoyl halide in the presence of pyridine.

The compounds of formula I where $R_2$, $R_2'$, $R_2''$ or $R_2'''$ is amino are prepared by hydrolysis of the corresponding compounds where $R_2$, $R_2'$, $R_2''$ or $R_2'''$ is lower-alkanoylamino or lower-alkoxycarbonylamino by heating the latter in aqueous alkali.

Alternatively, the compounds of formula I where $R_2$, $R_2'$, $R_2''$ or $R_2'''$ is amino are prepared by reaction of the compounds of formula I where Z is

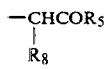

and $R_1$ is hydrogen with nitric acid in glacial acetic acid. The reaction is carried out at temperatures from 0° to 5° C. The resulting nitro compound is then alkylated as desired in the manner described above to prepare compounds where $R_1$ has the other various meanings given above, and in a final step, the nitro group is reduced to the corresponding amino group by either catalytic means, for example with hydrogen over palladium-on-charcoal, or by chemical means, for example by iron and hydrochloric acid or by tin and hydrochloric acid.

As indicated in the reaction sequence shown above, the 6-$R_2''$-7-$R_2$-8-$R_2'$-9-$R_2'''$-1-$R_1$-2-Q-4aα-$R_3$-5α-$R_4$-1,2,3,4,4a,5,10,10a-octahydro-3,5-ethenobenzo[g]quinolines of formula IIIa where Q is $H_2$, CH-lower-alkyl, CH-cycloalkyl, CH-cycloalkyl-lower-alkyl, CH-phenyl, CH-lower-alkylphenyl, or substituted CH-phenyl or CH-lower-alkylphenyl are produced along with the compounds of formula I (where Z is —$CH_2COR_5$) when the compounds of formula II where Y is $COR_5$ and $R_8$ is hydrogen are heated with formic acid in an organic solvent or with a benzyl-di-lower-alkylammonium formate or a tri-lower-alkylammonium formate as described above. When the benzazocines of formula I are the desired product, it is preferred to carry out the reaction in mesitylene using a concentration of 0.05 molar in starting material of formula II and 1.0 molar in formic acid. This mixture gives a reaction temperature at reflux of about 120° C. and affords the benzazocines of formula I and the benzo[g]quinolines of formula IIIa in a ratio of from 2:1 to 3:1. By progressively decreasing the formic acid concentration, successively higher boiling mixtures are produced, which result in production of progressively increased relative amounts of the benzo[g]quinolines. Thus at formic acid concentration of 0.5 molar and 0.15 molar (0.05 molar in starting material), the benzo[g]quinolines and benzazocines are produced in ratios of about 2:1 and 7:1, respectively. Similarly, by using a ratio of 1 mole of starting material to 5 moles of, respectively, benzyldimethylammonium formate or trimethylammonium formate or triethylammonium formate and heating the mixture (in the absence of any organic solvent) at 150° C. for about fifteen minutes, a mixture of benzo[g]quinoline and benzazocine is produced in ratios of 10:1, 3:1 and 20:1, respectively.

The two transformations thus take place simultaneously under the given conditions and are best seen by reference to the reaction sequence:

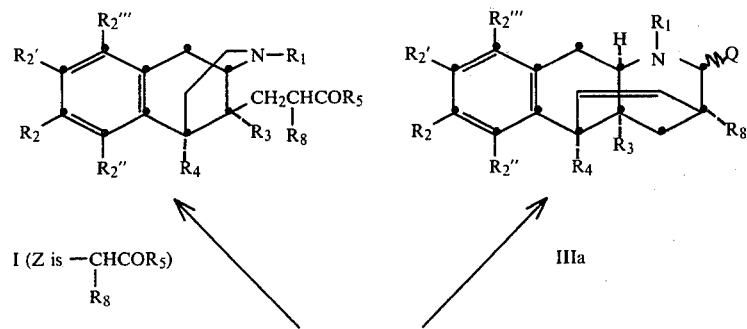

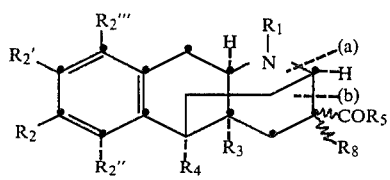

II (Y is COR$_5$)

wherein $R_1$, $R_2$, $R_2'$, $R_2''$, $R_2'''$, $R_3$, $R_4$, $R_5$, $R_8$ and Q have the meanings given above. It will be seen from the above that the compounds of formula I result by rupture, under the reaction conditions, of bond (b) in the compounds of formula II, whereas the compounds of formula IIIa result when bond (a) is broken, followed by ring closure between the nitrogen atom and the carbonyl group of the COR$_5$ moiety.

An alternative process for preparing the compounds of formula I which does not result in production of compounds of formula IIIa is the process described in T. R. Lewis and W. F. Michne U.S. Pat. No. 4,119,628, the disclosure of which is incorporated herein by reference, which is useful for the preparation of the compounds of formula I when Z is

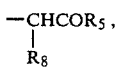

where $R_8$ is hydrogen and $R_5$ has all the meanings given above. According to the Lewis and Michne process, a lower-alkyl 1-$R_1$-3-$R_5$CO-4aα-$R_3$-5α-$R_4$-6-$R_2''$-7-$R_2$-8-$R_2'$-9-$R_2'''$ 1,2,3,4,4a,5,10,10a-octahydro-2,5-methanobenzo[g]quinoline-3-carboxylate having the formula IX is heated with formic acid in an inert organic solvent, for example toluene, xylene, or mesitylene, or with a benzyl-di-lower-alkylammonium formate or a tri-lower-alkylammonium formate using the same conditions as described above for the conversion of the compounds of formula II to the compounds of formula I. The reaction results in simultaneous ring opening between the carbon atoms at the 2- and 3-positions of the compounds of formula IX and hydrolysis and decarboxylation of the 3-carbo-lower-alkoxy group, COOAlk according to the following reaction:

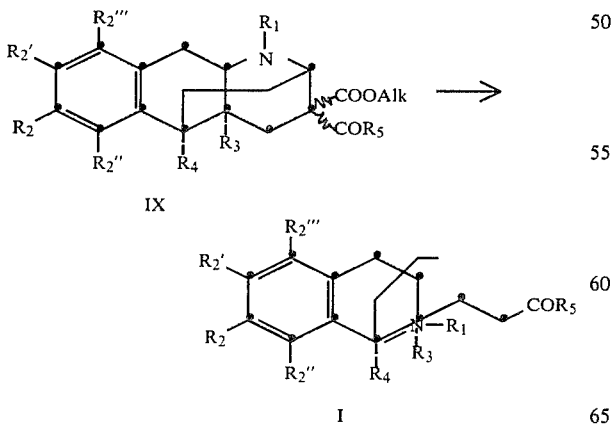

where $R_1$, $R_2$, $R_2'$, $R_2''$, $R_2'''$, $R_3$, $R_4$ and $R_5$ have the meanings given above and Alk represents lower-alkyl.

The compounds of formula IX and the methods for their preparation are described in the above-identified Lewis and Michne U.S. Pat. No. 4,119,628.

The compounds of formula IIIa where Q is oxo (=O), $R_1$ is hydrogen and $R_4$ is lower-alkyl are prepared by reaction of a 3-(4-$R_2$-3-$R_2'$[or 5-$R_2''$]-2-$R_2'''$-benzyl)-4-$R_3$-5-$R_4$-7-Y'-2-azabicyclo[2.2.2]oct-5-ene of formula IV where $R_1$ is hydrogen and Y' is COOR$_9$ with an alkali metal lower-alkoxide in a lower-alkanol solvent at a temperature in the range from 20° to 80° C. followed by heating the resulting 1-$R_3$-2-(4-$R_2$-3-$R_2'$[or 5-$R_2''$]-2-$R_2'''$-benzyl)-8-lower-alkylidene-3-azabicyclo[3.3.1]non-6-en-4-one of formula V with a mineral acid. The method is represented by the reaction sequence:

As indicated, the rearrangement of the compounds of formula IV to the compounds of formula V takes place by cleavage of the bond designated (c) in formula IV, cyclization of the ester group, $COOR_9$, to the nitrogen atom with formation of the lactam, shift of the endocyclic double bond and generation of an exocyclic double bond with loss of a proton from the $R_4$ lower-alkyl group. It will also be seen from the above-depicted reaction sequence that cyclization of the compounds of formula V to the compounds of formula III can take place either at the 2- or 6-position of the benzyl group to give rise to compounds of formula IIIa where the $R_2'$ (or $R_2''$) group occupies either the 6- or 8-position of the latter.

Furthermore, it will also be appreciated that the cyclization affords the compounds where both the $R_3$ and $R_4$ groups are in the α-configuration, i.e. trans to the 3,5-etheno bridge (vide infra).

The compounds of formula IIIa where Q is $H_2$ and $R_1$ is hydrogen are prepared by reduction of the corresponding compounds where Q is oxo (=O) with an alkali metal aluminum hydride. The reaction takes place in an organic solvent inert under the conditions of the reaction, for example diethyl ether, dibutyl ether, tetrahydrofuran, dioxane and the like, at a temperature in the range from 20° C. to 100° C.

The compounds of formula IIIa where $R_1$ is other than hydrogen are advantageously prepared by reaction of the compounds where $R_1$ is hydrogen with an appropriate lower-alkyl, lower-alkenyl, lower-alkynyl, halo-lower-alkenyl, cycloalkyl, cycloalkyl-lower-alkyl, 2- or 3-furylmethyl (or 2- or 3-furylmethyl substituted by from one to three methyl groups), phenyl-lower-alkyl or substituted-phenyl-lower-alkyl ester of a strong mineral acid, such as esters of hydrochloric, hydrobromic or sulfuric acid. The reaction is preferably carried out in the presence of an acid-acceptor, for example an alkali metal carbonate or bicarbonate, and in an inert organic solvent such as methanol, ethanol, acetone, isopropanol and the like.

The 6-$R_2''$-7-$R_2$-8-$R_2'$-9-$R_2'''$-1-$R_1$-2-Q-4aα-$R_3$-5α-$R_4$-1,2,3,4,4a,5,10,10a-octahydro-3,5-ethanobenzo[g]quinolines of formula IIIb are prepared by catalytic reduction of the corresponding 3,5-etheno compounds of formula IIIa with hydrogen over a palladium-on-charcoal catalyst using an inert organic solvent, for example methanol, ethanol or isopropanol.

The 6-$R_2''$-7-$R_2$-8-$R_2'$-9-$R_2'''$-1-$R_1$-3-Y-4aα-$R_3$-5α-$R_4$-1,2,3,4,4a,5,10,10a-octahydro-2,5-methanobenzo[g]quinolines of formula II which, as described above, serve as key intermediates for the preparation of the final products of formulas I, IIIa and IIIb are in turn prepared as follows:

The compounds of formula II where Y is carboxy, cyano, carbo-lower-alkoxy, $COR_5$, COO-lower-alkylene-cycloalkyl or COO-lower-alkylene-phenyl are prepared by the acid catalyzed cyclization of an appropriate 2-$R_1$-3-(4-$R_2$-3-$R_2'$-[or 5-$R_2''$]-2-$R_2'''$-benzyl)-4-$R_3$-5-$R_4$-7-$Y'$-2-azabicyclo[2.2.2]oct-5-ene of formula IV, where $R_5$ is lower-alkyl. The compounds of formula II where $R_4$ is hydrogen are prepared from the corresponding compounds of formula IV where $R_1$ is lower-alkanoyl. The reaction is carried out by adding the starting material of formula IV to the acid and either allowing the reaction mixture to stand at a temperature in the range from about 0° C. to about 10° C. or heating to about 100° C. Preferred acids are hydrofluoric acid, hydrobromic acid, sulfuric acid, phosphoric acid, and the like. A particularly preferred acid is hydrofluoric acid.

As in the case of the cyclization of the compounds of formula V to the compounds of formula IIIa, cyclization of the compounds of formula IV to the compounds of formula II can take place at either the 2- or the 6-position of the benzyl group to produce compounds of formula II where the $R_2'$ (or $R_2''$) group occupies either the 6- or the 8-position of the latter. And furthermore, as in the cyclization of the compounds of formula V to the compounds of formula IIIa, cyclization of the compounds of formula IV to those of formula II affords the compounds where both the $R_3$ and the $R_4$ groups are in the α-configuration, i.e. trans to the 2,5-methano bridge.

Moreover, during the course of the cyclization reaction, various ester or ether groups, [e.g. compounds where $Y'$ in the compounds of formula IV or Y in the compounds of formula II is an ester group or one of $R_2$, $R_2'$, $R_2''$ or $R_2'''$ is, for example, lower-alkoxy] are often cleaved to the respective carboxylic acid or the phenolic compound, particularly when the reaction mixture is heated using, for example, hydrobromic acid. In such cases the products must be re-esterified or realkylated using standard procedures, if the esters or the ethers are the desired product. This circumstance is readily obviated if desired by use of hydrofluoric acid as the acid catalyst which only requires a reaction temperature of around 0°–10° C. Under these mild conditions, ester and ether groups remain unchanged during the reaction.

The above described method for the preparation of compounds of formula II is particularly advantageous for the preparation of compounds of formula II where Y is carboxy, cyano, carbo-lower-alkoxy, $COR_5$, COO-lower-alkylene-cycloalkyl or COO-lower-alkylene-phenyl where $R_5$ is lower-alkyl. The compounds of formula II where Y is the group

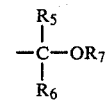

where $R_5$, $R_6$ and $R_7$ have the meanings given above are advantageously prepared from the compounds of formula II where Y has the other meanings given above by methods involving various transformations of the Y group as carboxy, carboxylic acid ester or $COR_5$ as described above in connection with the preparation of the compounds of formula I.

The compounds of formula II where Y is carboxy, cyano, carbo-lower-alkoxy, COO-lower-alkylene-cycloalkyl, COO-lower-alkylene-phenyl, or a group of the formula:

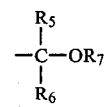

where one or both of $R_5$ and $R_6$ is hydrogen or lower-alkyl, and $R_7$ has the same meanings as in formula I can be converted to the compounds of formula II where Y is a $COR_5$ group by simple chemical transformations such as hydrolysis of a nitrile or ester to the carboxylic acid, or saponification of an ester of an hydroxymethyl-bearing compound ($R_5$, $R_6$ and $R_7$ are hydrogen) and oxidation of the hydroxymethyl group to the carboxylic acid. The latter can then be reacted with two moles of an appropriate organo lithium, $R_5Li$, or the ester (Y is carbo-lower-alkoxy) can be reacted with one mole of an appropriate sterically hindered organo lithium, e.g. t-butyl lithium, to produce, in either case, the compounds where Y is $COR_5$. Compounds of formula II where $R_7$ and one of $R_5$ and $R_6$ is hydrogen and the other is lower-alkyl, cycloalkyl, cycloalkyl-lower-alkyl, phenyl, phenyl-lower-alkyl or substituted-phenyl or phenyl-lower-alkyl can likewise be converted to the compounds where Y is $COR_5$ by oxidation. The compound of formula II where Y has the above-indicated meanings are thus also useful as intermediates for preparing the compounds of formula II where Y is $COR_5$, which in turn are useful as intermediates for the preparation of the compounds of formula I.

The compounds of formula II where Y is the group

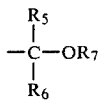

where $R_5$ and $R_6$ are hydrogen, lower-alkyl, cycloalkyl, cycloalkyl-lower-alkyl, phenyl, phenyl-lower-alkyl or substituted-phenyl or phenyl-lower-alkyl and $R_7$ is hydrogen, which as indicated above are intermediates for preparing the compounds of formula I, are prepared by saponification of the corresponding compounds where $R_7$ is lower-alkanoyl, benzoyl or substituted-benzoyl. The compounds of formula II where $R_7$ is lower-alkanoyl, benzoyl or substituted-benzoyl are thus intermediates for the compounds where $R_7$ is hydrogen. The ester forms are useful compounds for purification of the carbinols and serve as intermediates for the latter.

The compounds of formulas I or II where $R_1$ is benzyl can be catalytically debenzylated to give the corresponding compounds where $R_1$ is hydrogen. The latter can then be realkylated with an appropriate alkylating agent to give other different compounds where $R_1$ has the meanings, other than hydrogen, given above. Reduction is carried out in an inert organic solvent, for example ethanol, isopropanol, and the like, and at pressures from 40 to 100 p.s.i.g. A preferred catalyst is palladium-on-charcoal. The alkylation of the compounds of formulas I or II where $R_1$ is hydrogen is carried out in an inert organic solvent, for example acetone, ethanol or DMF, and in the presence of an acid-acceptor, for example alkali metal carbonates or bicarbonates.

Finally the 2-$R_1$-3-(4-$R_2$-3-$R_2'$[or 5-$R_2''$]-2-$R_2'''$-benzyl)-4-$R_3$-5-$R_4$-7-Y'-2-azabicyclo[2.2.2]oct-5-enes of formula IV, which serve as intermediates for the preparation of the key intermediates of formula II are themselves prepared by reaction of a Grignard reagent derived from a 4-$R_2$-3-$R_2'$(or 5-$R_2''$)-2-$R_2'''$-benzyl halide of formula VI with an appropriate 3-$R_3$-4-$R_4$-1-$R_1$-pyridinium halide of formula VII followed by Diels-Alder condensation of the resulting 1-$R_1$-2-(4-$R_2$-3-$R_2'$[or 5-$R_2''$]-2-$R_2'''$-benzyl)-3-$R_3$-4-$R_4$-1,2-dihydropyridine of formula VIII with an appropriate dienophile, $CH_2=CHY'$.

The reaction with the Grignard reagent is carried out at a temperature in the range from 0° C. to 25° C. in an inert organic solvent, for example diethyl ether, tetrahydrofuran or dibutyl ether and is effected by addition of a solution of the Grignard to a suspension of the quaternary salt in the reaction solvent. The resulting dihydro compound of formula VIII is generally not isolated and purified, but rather is carried forward directly to the next step involving reaction with the dienophile without further purification. The reaction of the dihydro compounds of formula VIII with the dienophile can either be carried out in an excess of the latter as a solvent or in an inert organic solvent such as benzene, toluene or xylene. Reaction is preferably carried out at the reflux temperature of the mixture.

The 3-$R_3$-4-$R_4$-pyridines, from which the quaternaries of formula VII are prepared, and also the 4-$R_2$-3-$R_2'$-(or 5-$R_2''$)-2-$R_2'''$-benzyl halides, from which the Grignard reagents are prepared, are known classes of compounds.

Due to the presence of a basic amino grouping, the free base forms represented by formulas I, II, IIIa, IIIb and IV above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed.

The compounds of this invention can exist in stereochemically isomeric forms, that is, optical isomers and geometric isomers. If desired, the isolation or the production of a particular stereochemical form can be accomplished by application of the general principles known in the prior art. In the nomenclature employed for the compounds of formula I herein, "ax" stands for axial and "eq" for equatorial, and the configurations are given with reference to the hydroaromatic ring. Thus, the 6(eq), 11(ax) compounds of formula I are in the cis configuration, whereas the 6(eq), 11(eq) compounds are in the trans configuration.

In the nomenclature employed for the compounds of formulas II, IIIa and IIIb, again configurations are given with reference to the hydroaromatic ring, and the designation "β" indicates the cis configuration relative to the 2,5-methano bridge of the compounds of formula II or the 3,5-ethano (or 3,5-etheno) bridge of the compounds of formulas IIIa and IIIb. Conversely, the designation "α" indicates the trans configuration relative to the same groups.

In standard pharmacological test procedures, the compounds of formulas I, IIIa and IIIb and the acid-addition salts thereof have been found useful as depressants of the central nervous system, and more particularly have been found useful as analgesics and as antagonists of strong analgesics such as phenazocine, meperidine and morphine. In addition, particular species of the compounds of formula II have been found useful as analgesics.

The compounds of formulas I, II, IIIa and IIIb can be administered in the same manner as known analgesics and antagonists of strong analgesics, i.e. parenterally or orally in any of the conventional pharmaceutical forms, as for instance solutions, suspensions, tablets, capsules, and the like.

As described above and as will be seen hereinbelow, many of the species of formulas I, II, IIIa, IIIb and IV are readily interconvertible by simple and well-known reactions such as reduction, oxidation, hydrolysis, esterification, etherification, and the like, so that they are also useful as intermediates for each other.

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation.

The test procedures used to determine the analgesic and analgesic antagonist activities of the compounds of the invention have been described in detail in the prior art and are as follows: the acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); the phenyl-p-quinone-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol. Exptl. Therap. 72, 74 (1941) as modified by Bass and Vander-Brook, J. Am. Pharm. Assoc. Sci. Ed. 41, 569 (1956); and the phenazocine antagonist test, which is designed to measure the ability of a test agent to antagonize the effect of phenazocine in the above-indicated rat tail flick response test, described by Harris and Pierson, J. Pharmacol. Exptl. Therap. 143, 141 (1964).

The structure of the compounds of this invention were established by the modes of synthesis, by elementary analyses and by ultraviolet, infrared and nuclear magnetic resonance spectra. The course of reactions and homogeneity of the products were ascertained by thin layer chromatography.

The manner and process of making and using the invention, and the best mode contemplated by the inventor of carrying out this invention, will now be described so as to enable any person skilled in the art to which it pertains to make and use the same. The melting points are uncorrected unless noted otherwise.

PREPARATION OF INTERMEDIATES

Example 1

A. A solution of 76 g. (0.6 mole) of benzyl chloride in 450 ml. of diethyl ether was added to a mixture of 14.6 g. (0.6 moles) of magnesium turnings in 150 ml. of dry ether at such a rate as to maintain gentle reflux. The resulting solution was then added by filtration through glass wool to a suspension of 75 g. (0.3 mole) of 4-ethylpyridine methiodide in 150 ml. of ether. The mixture was stirred for three hours at room temperature, poured into a mixture of ice/water containing ammonium chloride, and the organic layer was separated, dried, filtered, and diluted with ether to a volume of 900 ml.

The solution containing 1-methyl-2-benzyl-4-ethyl-1,2-dihydropyridine was divided into three 300 ml. portions, and each portion was evaporated to dryness, dissolved, respectively, in 200 ml. portions of benzene, toluene and xylene, and the three separate solutions treated with 22 ml. of ethyl acrylate and refluxed overnight. The solutions were each allowed to cool, diluted with diethyl ether and extracted with 150 ml. of 1 N hydrochloric acid. The combined extracts were washed once with diethyl ether, then basified with 15 ml. of concentrated ammonium hydroxide and the mixtures each extracted with 150 ml. of diethyl ether. The extracts of the three samples afforded, respectively, 18.2 g., 20.0 g. and 19.3 g. of product as oils. The three samples were dissolved in diethyl ether and acidified with ethereal hydrochloric acid to give a total of 32.2 g. of ethyl 2-methyl-3-benzyl-5-ethyl-2-azabicyclo[2.2.2]oct-5-ene-7-carboxylate hydrochloride, m.p. 189°–191° C.

Following a procedure similar to that described in Example 1A, using either benzene, toluene or xylene as solvent, an appropriate 4-$R_2$-3-$R_2'$-2-$R_2'''$-benzylmagnesium chloride of formula VI, an appropriate 3-$R_3$-4-$R_4$-1-$R_1$-pyridinium halide of formula VII and an appropriate dienophile, $CH_2=CHY'$, the following 2-$R_1$-3-(4-$R_2$-3-$R_2'$-2-$R_2'''$-benzyl)-4-$R_3$-5-$R_4$-7-$Y'$-2-azabicyclo[2.2.2]oct-5-enes of formula IV are prepared. Unless noted otherwise, the products were isolated and characterized in the form of the hydrochloride salt. The anion of the quaternary of formula VII is given in parentheses along with the weight of VII used.

Here and elsewhere throughout this specification in subsequent tables, the weights of the principal, organic starting materials (S.M.) and products (Prod.) are given in grams in the appropriate columns headed "Wt.___", and the melting points of the final products, together with the solvent of recrystallization, are given in the last column.

Where weights of only one of several reactants are given, the weights of such other reactants can be calculated on a proportionate molar basis from the amounts used in the example referred to for the preparative procedure employed. In some instances, the products were neither characterized nor purified, either by distillation or recrystallization, but rather were used directly in the next step as isolated from the reaction mixture.

The particular form of the starting material or product, whether base or salt, is specified along with the weights by use of designations such as "base", "HCl", "HBr", etc. to indicate that the weights are given, respectively, for the free base or the hydrochloride, hydrobromide, etc. salts.

TABLE 1a

| Example | $R_1/Y'$ | $R_2/R_2'$ | $R_3/R_4$ | Wt. VII/Wt. IV | m.p. (°C.)/Solv. |
|---|---|---|---|---|---|
| 1B | $C_6H_5CH_2$ | H | H | 23.4 ($Cl^-$) | 196-199 |
|  | $COOC_2H_5$ | H | $C_2H_5$ | 15.3 | ethanol/ether |
| 1C | $C_6H_5CH_2$ | $CH_3O$ | H | 117 ($Cl^-$) | 183-186 |
|  | $COOC_2H_5$ | H | $C_2H_5$ | 76 | ethanol/ether |
| 1D | $CH_3$ | $CH_3O$ | H | 124 ($I^-$) | 202-204 |
|  | $COOC_2H_5$ | H | $C_2H_5$ | 76 | ethanol/ether |
| 1E | $CH_3$ | H | H | 117 ($I^-$) | 237-238 |
|  | $COOC_2H_5$ | H | $CH_3$ | 57 | ethanol/ether |
| 1F | $C_6H_5CH_2$ | H | H | 109.9 ($Cl^-$) | 215-217 |
|  | $COOC_2H_5$ | H | $CH_3$ | 114.9 | ethanol/ether |
| 1G | $C_6H_5CH_2$ | H | H | 117 ($Cl^-$) | 106-111 (a) |
|  | $COCH_3$ | H | $C_2H_5$ | 43.7 | ethanol |
| 1H | $C_6H_5CH_2$ | $CH_3O$ | H | 154 ($Cl^-$) | 216-219 |
|  | $COOC_2H_5$ | H | $CH_3$ | 120 | ethanol/ether |
| 1J | $CH_3$ | H | $CH_3$ | 75.9 ($I^-$) | 168-170 |
|  | $COCH_3$ | H | $CH_2H_5$ | 26.8 | ethanol/ether |
| 1K | $CH_3$ | H | $CH_3$ | 50 ($I^-$) | 174 |
|  | $COCH_3$ | H | $CH_3$ | 19.3 | ethanol/ether |
| 1L | $CH_3$ | H | $CH_3$ | 37.4 ($I^-$) | 240-241 (b) |
|  | CN | H | $CH_3$ | 17 | ethanol |
| 1M | $CH_3$ | $CH_3O$ | H | 165 ($I^-$) | 200-202 (c) |
|  | $COOCH_3$ | H | $CH_3$ | 58.8 | ethanol/acetone |
| 1N | $C_6H_5CH_2$ | H | H | 165 ($Cl^-$) | 165-170 (d) |
|  | $COCH_3$ | H | $CH_3$ | 123.1 | ethanol/ether |
| 1P | $CH_3$ | H | H | 27.9 ($I^-$) | 146-149 |
|  | $COOC_2H_5$ | H | $CH_2CH_2OCH_3$ | 6.4 | ethanol/ether |
| 1Q | $C_3H_5-CH_2$ (e) | H | H | 11.6 ($Br^-$) | 230 |
|  | $COOC_2H_5$ | H | $CH_3$ | 8.6 | ethanol |
| 1R | $CH_3$ | H | H | 184 ($I^-$) | 171-174 |
|  | $COOC_2H_5$ | H | $C_3H_7$ | 71.3 | ethanol/ether |
| 1S | $C_6H_5CH_2$ | $CH_3O$ | H | 112 ($Cl^-$) | 125-130 |
|  | $COCH_3$ | H | $CH_3$ | 64.5 | ethanol/ether |
| 1T | $C_6H_5CH_2$ | H | $CH_3$ | 11.7 ($Cl^-$) | 218-220 |
|  | $COOC_2H_5$ (g) | H | $CH_3$ | 6.1 | ethanol/ether |
| 1U | $C_6H_5CH_2$ | $CH_3O$ | $CH_3$ | 157 ($Cl^-$) | 146 |
|  | $COCH_3$ | H | $CH_3$ | 15.3 | ethanol/ether |
| 1V | $C_6H_5CH_2$ | $CH_3O$ | H | 165 ($Cl^-$) | 122-127 |
|  | $COCH_3$ | H | $C_2H_5$ | 105.3 | acetone |
| 1W | $C_6H_5CH_2$ | H | $CH_3$ | 238 ($I^-$) | 166-168 |
|  | $COCH_3$ | H | $C_2H_5$ | 36.3 | ethanol/ether |
| 1X | $C_6H_5CH_2$ | H | $CH_3$ | 46.8 ($Cl^-$) | oil |
|  | $COCH_3$ | H | $CH_3$ | 54 |  |
| 1Y | $CH_3$ | H | H | 40.0 ($I^-$) | 127-129 (f) |
|  | $COOC_2H_5$ | H | $CH_2CH_2SC_6H_5$ | 37 | acetone |
| 1Z | $C_6H_5CH_2$ | H | $C_2H_5$ | 172 ($I^-$) | 204-208 |
|  | $COOC_2H_5$ | H | $CH_3$ | 54 | ethanol/ether |
| 1AA | $CH_3$ | H | $CH_3$ | 149 | 188-190 |
|  | $COOC_2H_5$ | H | $C_2H_5$ | 109 | ethanol/ether |
| 1AB | $CH_3$ | $CH_3O$ | $CH_3$ | 148 | 186-188 |
|  | $COOC_2H_5$ | H | $C_2H_5$ | 46 | ethanol/ether |
| 1AC | $C_6H_5CH_2$ | H | $CH_3$ | 33.9 | 214-217 |
|  | $COOC_2H_5$ | H | $C_2H_5$ | 5.5 | ethanol/ether |
| 1AD | $CH_3$ | H | H | 94 | 167-169 |
|  | $COOC_2H_5$ | H | H | 2.7 | ethanol/ether |
| 1AE | $C_6H_5CH_2$ | H | H | 25.3 | 201-203 |
|  | $COOC_2H_5$ | H | H | 0.9 | ethanol/ether |
| 1AF | $CH_3$ | H | $CH_3$ | 50 | 25-218 |
|  | $COOC_2H_5$ | H | $CH_3$ | 27.5 | ethanol/ether |
| 1AG | $C_6H_5CH_2$ | $CH_3O$ | $CH_3$ | 200 | 208-210 |
|  | $COOC_2H_5$ | H | $CH_3$ | 31.5 | — |
| 1AH | $C_6H_5CH_2$ | H | $CH_3$ | 285 ($Cl^-$) | 203-212 |
|  | $COOC_2H_5$ | $CH_3O$ | $CH_3$ | 120.7 | acetone/ether |
| 1AJ | $C_6H_5CH_2$ | H | $CH_3$ | 11.9 ($Cl^-$) | 229.5-232.5 |
|  | $COOC_2H_5$ | $CH_3O$ (h) | $CH_3$ | 6.0 | ethanol/ether |
| 1AK | $CH_3$ | $CH_3O$ | $CH_3$ | 121.3 ($Br^-$) | 191.0-201.0 (f) |
|  | $COOC_2H_5$ | H | $CH_3$ | 70.1 |  |
| 1AL | $CH_3$ | $CH_3O$ | $-(CH_2)_4-$ | 19.0 ($I^-$) | 181-183 |

TABLE 1a-continued

| Example | R₁/Y'   | R₂/R₂' | R₃/R₄ | Wt. VII/Wt. IV | m.p. (°C.)/Solv. |
|---------|---------|--------|-------|----------------|------------------|
|         | COOC₂H₅ | H      |       | 10.6           | ethanol/ether    |

(a) Free base
(b) Hydrochloride hemiethanolate
(c) The corresponding ethyl ester hydrochloride prepared similarly using ethyl acrylate as the dienophile has m.p 205°-206° C. (from ethanol).
(d) The free base has m.p. 118°-120° C. (from isopropanol).
(e) Cyclopropylmethyl
(f) Oxalate. The free base has m.p. 67°-68° C. (from pentane).
(g) The carboxylic acid (47 g.), m.p. 191°-196° C. (free base), was prepared by saponification of the ester (58.5 g.)
(h) CH₃O group in 2-position.

Example 1AM

A solution of 21.1 g. (0.05 mole) of the ethyl 2,3-dibenzyl-5-ethyl-2-azabicyclo[2.2.2]oct-5-ene-7-carboxylate hydrochloride described above in Example 1B was dissolved in a solution of 100 ml. of 1 N sodium hydroxide and 100 ml. of ethanol, and the solution was heated and stirred under reflux for four hours. The ethanol was then removed in vacuo, the mixture diluted with water and then acidified with glacial acetic acid. Extraction of the mixture with chloroform afforded 21.1 g. of a gummy material which was dissolved in methanol and treated with an excess of methanesulfonic acid. The solid which separated on dilution with diethyl ether was collected to give 15.1 g. of 2,3-dibenzyl-5-ethyl-2-azabicyclo[2.2.2]oct-5-ene-7-carboxylic acid methanesulfonate, m.p. 220°-222° C.

Example 1AN

A solution of 10 g. (0.02 mole) of ethyl 2-benzyl-3-(4-methoxybenzyl)-5-methyl-2-azabicyclo[2.2.2]oct-5-ene-7-carboxylate hydrochloride described above in Example 1H in 100 ml. of absolute ethanol was reduced with hydrogen over 1.0 g. of 10% palladium-on-charcoal, and when reduction was complete, the catalyst was removed by filtration and the filtrate taken to dryness. The residue was recrystallized from ethanol/ether to give 7.0 g. of ethyl 3-(4-methoxybenzyl)-5-methyl-2-azabicyclo[2.2.2]oct-5-ene-7-carboxylate hydrochloride, m.p. 173°-175° C., which on further recrystallization gave material having m.p. 177°-179° C.

Following a procedure similar to that described in Example 1AN, above, the following compounds of formula IV were prepared, where in each case R₁, R₂, R₂', R₂" and R₂''' are hydrogen; R₄ is CH₃ and Y' is COOC₂H₅. Both compounds were isolated and characterized as the hydrochloride salt.

TABLE 1b

| Example | R₃  | Wt.S.M./Wt.Prod. | m.p.(°C.)/Solvent     |
|---------|-----|------------------|-----------------------|
| 1AP     | CH₃ | 42.6             | 223-226               |
|         |     | 24.2             | ethanol/ether         |
| 1AQ     | H   | 34.0             | 160-162               |
|         |     | 20.1             | acetone               |

Following a procedure similar to that described in Example 1A, using an appropriate 4-R₂-3-R₂'-2-R₂"'-benzylmagnesium chloride of formula VI, an appropriate 3-R₃-4-R₄-1-R₁-pyridinium halide of formula VII and methyl vinyl ketone as dienophile, the following 2-R₁-3-(4-R₂-3-R₂'-2-R₂"-benzyl)-4-R₃-5-R₄-7—CH₃CO—2-azabicyclo[2.2.2]oct-5-enes of formula IV are prepared, where in each case Y' is COCH₃ and R₂''' is hydrogen.

TABLE 1c

| Ex. | R₁                                      | R₂/R₂'            | R₃/R₄                |
|-----|-----------------------------------------|-------------------|----------------------|
| 1AR | CH₃                                     | H                 | H                    |
|     |                                         | Cl                | CH₃                  |
| 1AS | CH₃                                     | H                 | H                    |
|     |                                         | Br                | CH₃                  |
| 1AT | CH₃                                     | H                 | H                    |
|     |                                         | F                 | CH₃                  |
| 1AU | CH₃                                     | H                 | H                    |
|     |                                         | CH₃               | CH₃                  |
| 1AV | CH₃                                     | H                 | H                    |
|     |                                         | CH₃               | CH₃                  |
| 1AW | CH₃                                     | C₆H₅              | H                    |
|     |                                         | H                 | CH₃                  |
| 1AX | CH₃                                     | CH₂<O—O           | H                    |
|     |                                         |                   | CH₃                  |
| 1AY | CH₃                                     | H                 | H                    |
|     |                                         | H                 | H                    |
| 1AZ | CH₃                                     | H                 | H                    |
|     |                                         | H                 | CH₂CH₂Cl             |
| 1BA | CH₃                                     | H                 | —(CH₂)₃—             |
|     |                                         | H                 |                      |
| 1BB | CH₃                                     | H                 | —(CH₂)₄—             |
|     |                                         | H                 |                      |
| 1BC | C₆H₁₁                                   | CH₃S              | H                    |
|     |                                         | H                 | CH₃                  |
| 1BD | 4-BrC₆H₄CH₂CH₂                          | CH₃O              | H                    |
|     |                                         | H                 | CH₃                  |
| 1BE | 4-ClC₆H₄CH₂CH₂                          | CH₃CONH           | H                    |
|     |                                         | H                 | CH₃                  |
| 1BF | 4-FC₆H₄CH₂CH₂                           | C₂H₅OCONH         | H                    |
|     |                                         | H                 | CH₃                  |
| 1BG | 4-Cl—3-CH₃C₆H₃CH₂CH₂                    | H                 | H                    |
|     |                                         | H                 | CH₃                  |
| 1BH | 3-CH₃COOC₆H₄CH₂CH₂                      | H                 | H                    |
|     |                                         | H                 | CH₃                  |
| 1BJ | 3,4-(CH₃O)₂C₆H₃CH₂CH₂                   | H                 | H                    |
|     |                                         | H                 | CH₃                  |
| 1BK | 4-CH₃SC₆H₄CH₂CH₂                        | H                 | H                    |
|     |                                         | H                 | CH₃                  |
| 1BL | 3-CF₃C₆H₄CH₂CH₂                         | H                 | H                    |
|     |                                         | H                 | CH₃                  |
| 1BM | 3-CH₃CONHC₆H₄CH₂CH₂                     | H                 | H                    |
|     |                                         | H                 | CH₃                  |
| 1BN | 3,4-OCH₂OC₆H₃CH₂CH₂                     | H                 | H                    |
|     |                                         | H                 | CH₃                  |
| 1BP | CH₃                                     | H                 | H                    |
|     |                                         | H                 | CH₂CH₂SCH₃           |

EXAMPLE 1BQ

Reduction of the ethyl 2,3-dibenzyl-2-azabicyclo[2.2.2]-oct-5-ene-7-carboxylate described in Example 1AE in the form of the hydrochloride salt with one molar equivalent of hydrogen over a palladium-on-charcoal catalyst at ambient temperature and reaction of the resulting ethyl 3-benzyl-2-azabicyclo[2.2.2]oct-5-ene-7-carboxylate with acetyl chloride in the presence of pyridine affords ethyl 2-acetyl-3-benzyl-2-azabicyclo[2.2.2]oct-5-ene-7-carboxylate.

EXAMPLE 2

A. A mixture of 12.3 g. (0.035 mole) of the ethyl 2-methyl-3-benzyl-5-ethyl-2-azabicyclo[2.2.2]oct-5-ene-7-carboxylate hydrochloride, described above in Example 1A, in 125 ml. of 48% aqueous hydrobromic acid was stirred under reflux for twenty-four hours and cooled. The solid which separated was collected to give 8.4 g. of 1-methyl-5α-ethyl-1,2,3,4,4a,5,10,10a-octahydro-2,5-methanobenzo[g]quinoline-3-carboxylic acid hydrobromide, m.p. 290°–293° C., which on recrystallization from water gave material having m.p. 295°–299° C.

Following a procedure similar to that described in Example 2A, using an appropriate 2-$R_1$-3-(4-$R_2$-benzyl)-4-$R_3$-5-$R_4$-7-Y'-2-azabicyclo[2.2.2]oct-5-ene of formula IV, the following 7-$R_2$-1-$R_1$-3-Y-4aα-$R_3$-5α-$R_4$-1,2,3,4,4a,5,10,10a-octahydro-2,5-methanobenzo[g]quinolines of formula II are prepared where, unless noted otherwise, $R_2'$, $R_2''$, $R_2'''$ and $R_8$ in each case are hydrogen. The cyclization can be carried out using hydrofluoric acid at 0°–15° C., concentrated sulfuric acid at ambient temperature, or hydrobromic acid in glacial acetic acid at reflux temperature. The particular acid used to promote reaction in each case is identified below by the designations HF, $H_2SO_4$ and HBr, as the case may be. Unless noted otherwise the products were isolated as the hydrochloride salts.

TABLE 2a

| Example | $R_1$/Y | $R_2$ | $R_3$/$R_4$ | Wt. IV/Wt. II | m.p. (°C.)/Solv. |
|---|---|---|---|---|---|
| 2B | $C_6H_5CH_2$ | H | H | 42.6 | 258–260 |
| HBr | COOH (a) | | $C_2H_5$ | 11.5 | ethanol/ether |
| 2C | $CH_3$ | HO | H | 58.1 | 293 (c) |
| HBr | COOH (b) | | $C_2H_5$ | 30.2 | $H_2O$ |
| 2D | $CH_3$ | H | H | 50 | 269 (c) |
| HBr | COOH (a) | | $CH_3$ | 36.7 | ethanol/ether |
| 2E | $C_6H_5CH_2$ | H | H | 10 | 109–111 (d) |
| $H_2SO_4$ | $COCH_3$ | | $C_2H_5$ | 7.1 | methanol |
| 2F | $C_6H_5CH_2$ | $CH_3O$ | H | 10 | 225–228 |
| HF | $COOC_2H_5$ | | $CH_3$ | 7.3 | acetone |
| 2G | $CH_3$ | H | $CH_3$ | 10 | 99–103 (d) |
| $H_2SO_4$ | $COCH_3$ | | $C_2H_5$ | 3.7 | hexane |
| 2H | $CH_3$ | HO (e) | H | 45.0 | 283–284 |
| HBr | $COOCH_3$ | | $CH_3$ | 17.6 | ethanol |
| 2J | $CH_3$ | H | H | 88.4 | 228–229 |
| HBr | $COOC_2H_5$ | | $C_3H_7$ | 23.2 | isopropanol |
| 2K | $C_6H_5CH_2$ | $CH_3O$ | H | 5.0 | 126–129 (d) |
| HF | $COCH_3$ | | $CH_3$ | 2.6 | ethanol |
| 2L | $C_6H_5CH_2$ | $CH_3O$ | H | 176 | 88–90 (d) |
| HF | $COCH_3$ | | $C_2H_5$ | 43.2 | ethanol |
| 2M | $CH_3$ | $CH_3O$ | H | 153.7 | 101–102 (d) |
| HF | $COOC_2H_5$(f) | | $CH_3$ | 94.6 | ethyl acetate |
| 2N | $C_6H_5CH_2$ | H | $CH_3$ | 200 | 207–209 |
| HF | $COOC_2H_5$ | | $CH_3$ | 167 | ethanol/ether 88–90 (d) |
| 2P | $C_6H_5CH_2$ | $CH_3O$ | $CH_3$ | 4.3 | 125–126 (d) |
| HF | $COCH_3$ | | $CH_3$ | 3.2 | ethanol |
| 2Q | $C_6H_5CH_2$ | H | $CH_3$ | 79.2 | 95–98 (d) |
| HF | $COCH_3$ | | $C_2H_5$ | 29.3 | ethanol |
| 2R | $C_6H_5CH_2$ | $CH_3O$ | H | 0.5 | 244–246 |
| HF | $COOC_2H_5$ | | $C_2H$ hd 5 | 0.25 | ethanol/ether |
| 2S | $C_6H_5CH_2$ | H | H | 66 | 200–203 |
| HF | $COOC_2H_5$ | | $CH_3$ | 53 | ethanol/ether |
| 2T | $C_6H_5CH_2$ | H | H | 10 | 136–138 (d) |
| $H_2SO_4$ | $COCH_3$ | | $CH_3$ | 3 | ethanol |
| 2U | $CH_3$ | H | H | 1.0 | 189–191 |
| HF | $COOC_2H_5$ | | $CH_2CH_2OCH_3$ | 0.85 | ethanol/ether |
| 2V | $CH_3$ | H | H | 10 | 185–189 |
| HF | $COOC_2H_5$ | | $CH_2CH_2SC_6H_5$ | 5.6 | acetone |
| 2W | $CH_3$ | H | $CH_3$ | 11.1 | 225–227 |
| HF | $COOC_2H_5$ | | $CH_3$ | 9.2 | acetone |
| 2X | $CH_3$ | H | $CH_3$ | 10.9 | 202–205 |
| $H_2SO_4$ | $COOC_2H_5$ | | $C_2H_5$ | 5.9 | acetonitrile/ether |
| 2Y | $C_6H_5CH_2$ | H | $CH_3$ | 33.7 | 82–83(d) |
| $H_2SO_4$ | $COOC_2H_5$ | | $C_2H_5$ | 21.4 | hexane |
| 2A | $C_6H_5CH_2$ | H | $C_2H_5$ | 75 | 213–215 |
| $H_2SO_4$ | $COOC_2H_5$ | | $CH_3$ | 29 | ethanol/ether |
| 2AA | $C_6H_5CH_2$ | $CH_3O$ | $CH_3$ | 314.5 | 98–100(d) |
| HF | $COOC_2H_5$ | | $CH_3$ | 137.9 | |
| 2AB | $CH_3$ | $CH_3O$ | $CH_3$ | 21.7 | 98–101 |
| HF | $COOC_2H_5$ | | $C_2H_5$ | 16.1 | ethanol |
| 2AC | $C_6H_5CH_2$ | $CH_3O$ (g) | $CH_3$ | 94 | 123–124 (d,h) |
| HF | $COOC_2H_5$ | | $CH_3$ | 31.4 (h) | ethanol |
| 2AD | $C_6H_5CH_2$ | $CH_CO$(j) | $CH_3$ | 73.5 | 207.0–14 209.5 |
| HF | $COOC_2H_5$ | | $CH_3$ | 48.2 | ethanol/ether |
| 2AE | $CH_3$ | $CH_3O$ | $CH_3$ | 60.3 | 93.0–14 94.0(d) |
| HF | $COOC_2H_5$ | | $CH_3$ | 36.3 | ethanol |
| 2AF | $CH_3$ | $CH_3O$ | —$(CH_2)_4$— | 6.6 | oil |

TABLE 2a-continued

| Example | $R_1$/Y | $R_2$ | $R_3$/$R_4$ | Wt. IV/Wt. II | m.p. (°C.)/Solv. |
|---------|---------|-------|-------------|---------------|-------------------|
| HF      | COOC$_2$H$_5$ |   |             | 4.7           |                   |

(a) Starting material was the ethyl ester.
(b) Starting material was the methoxy ether/ethyl ester.
(c) Hydrobromide salt
(d) Free base
(e) Starting material was the methoxy ether/methyl ester.
(f) 100 g. of the ester was saponified with aqueous alkali and the product isolated as the free base to give 55.7 g. of the corresponding carboxylic acid, m.p. 195°–197° C. (acetonitrile).
(g) Prepared from compound of Example 1AH. CH$_3$O group is in the 8-position.
(h) Yield and m.p. given for 8-methoxy isomer. An additional 16.3 g. of isomeric 6-methoxy hydrochloride obtained, m.p. 226°14 227° C. (ethanol/ether).
(j) Prepared from the compound of Example 1AJ. CH$_3$O group is in the 9-position.

EXAMPLE 2AG

A solution of 4.2 g. (0.01 mole) of ethyl 1-methyl-5α-[2-(phenylthio)ethyl]-1,2,3,4,4a,5,10,10a-octahydro-2,5-methanobenzo[g]quinoline-3-carboxylate described in Example 2V in 80 ml. of glacial acetic acid was treated with 1.4 ml. of 30% aqueous hydrogen peroxide, allowed to stand at ambient temperature for one hour and fifteen minutes and then concentrated to dryness in vacuo at 40° C. The residue was partitioned between dilute sodium hydroxide and methylene dichloride and the organic layer separated, dried and taken to dryness to give 5.0 g. of ethyl 1-methyl-5α-[2-(phenylsulfinyl)ethyl]-1,2,3,4,4a,5,10,10a-octahydro-2,5-methanobenzo[g]quinoline-3-carboxylate as an oil.

The latter (14.0 g., 0.032 mole) was distilled under reduced pressure, and the fraction boiling at 122°–156° C./0.03–0.11 mm. was collected (7 g.) and chromatographed on silica in a 6:4 solution of hexane:ether. The column was eluted until the yellow color passed through, and the next 550 ml. was collected separately and taken to dryness to give 6.4 g. of a gum which was dissolved in anhydrous ether and diluted with ethereal hydrogen chloride. The solid which separated was collected and dried to give 3.8 g. of ethyl 1-methyl-5α-vinyl-1,2,3,4,4a,5,10,10a-octahydro-2,5-methanobenzo[g]quinoline-3-carboxylate hydrochloride, m.p. 241°–243° C.

The latter (2.1 g., 0.006 mole) was converted to the free base which was dissolved in 15 ml. of tetrahydrofuran and treated with 15.6 ml. of a 1 M solution of diborane in tetrahydrofuran. The solution was stirred for an hour and a half, poured into 10 ml. of ice water, the mixture basified with 3.6 ml. of 3 N sodium hydroxide and treated with 2.2 ml. of 30% hydrogen peroxide. After stirring for an hour, the mixture was filtered, diluted with water, extracted with ether and the ether extracts extracted with dilute hydrochloric acid. Isolation of the basic product from the aqueous acid medium in the usual manner by basifying and extraction with ether and conversion of the product to the hydrochloride salt gave ethyl 1-methyl-5α-(2-hydroxyethyl)-1,2,3,4,4a,5,10,10a-octahydro-2,5-methanobenzo[g]quinoline-3-carboxylate hydrochloride, m.p. 212°–216° C. (from acetone).

Following a procedure similar to that described in Example 2A, using an appropriate 2-$R_1$-3-(4-$R_2$-3-$R_2'$-benzyl)-4-$R_3$-5-$R_4$-7-Y'-2-azabicyclo[2.2.2]oct-5-ene of formula IV and hydrofluoric acid at 0°–15° C., the following 7-$R_2$-8-$R_2'$1-$R_1$-3-Y-4aα-$R_3$-5α-$R_4$-1,2,3,4,4a,5,10,10a-octahydro-2,5-methanobenzo[g]quinolines of formula II, where $R_2''$, $R_2'''$ and $R_8$ in each case are hydrogen, are prepared.

TABLE 2b

| Example | $R_1$/Y | $R_2$/$R_2'$ | $R_3$/$R_4$ |
|---------|---------|--------------|-------------|
| 2AH | C$_6$H$_5$CH$_2$ | CH$_3$O | H |
|     | COOC$_2$H$_5$ | H | CH$_3$ |
| 2AJ | CH$_3$ | H | CH$_3$ |
|     | COCH$_3$ | H | CH$_3$ |
| 2AK | CH$_3$ | H | CH$_3$ |
|     | CN | H | CH$_3$ |
| 2AL | cyclopropyl-CH$_2$ | H | H |
|     | COOC$_2$H$_5$ | H | CH$_3$ |
| 2AM | CH$_3$ | H | H |
|     | COCH$_3$ | Cl | CH$_3$ |
| 2AN | CH$_3$ | H | H |
|     | COCH$_3$ | Br | CH$_3$ |
| 2AP | CH$_3$ | H | H |
|     | COCH$_3$ | F | CH$_3$ |
| 2AQ | CH$_3$ | H | H |
|     | COCH$_3$ | CF$_3$ | CH$_3$ |
| 2AR | CH$_3$ | H | H |
|     | COCH$_3$ | CH$_3$ | CH$_3$ |
| 2AS | CH$_3$ | C$_6$H$_5$ | H |
|     | COCH$_3$ | H | CH$_3$ |
| 2AT | CH$_3$ | —O—CH$_2$—O— | H |
|     | COCH$_3$ |  | CH$_3$ |
| 2AU | CH$_3$ | H | H |
|     | COCH$_3$ | H | H |
| 2AV | CH$_3$ | H | H |
|     | COCH$_3$ | H | CH$_2$CH$_2$Cl |

TABLE 2b-continued

| Example | R₁/Y | R₂/R₂' | R₃/R₄ |
|---|---|---|---|
| 2AW | CH₃<br>COCH₃ | H<br>H | (CH₂)₃ |
| 2AX | CH₃<br>COCH₃ | H<br>H | (CH₂)₄ |
| 2AY | C₆H₁₁<br>COCH₃ | CH₃S<br>H | H<br>CH₃ |
| 2AZ | 4-BrC₆H₄CH₂CH₂<br>COCH₃ | CH₃O<br>H | H<br>CH₃ |
| 2BA | 4-ClC₆H₄CH₂CH₂<br>COCH₃ | CH₃CONH<br>H | H<br>CH₃ |
| 2BB | 4-FC₆H₄CH₂CH₂<br>COCH₃ | C₂H₅OCONH<br>H | H<br>CH₃ |
| 2BC | 4-Cl-3-CH₃C₆H₃CH₂CH₂<br>COCH₃ | H<br>H | H<br>CH₃ |
| 2BD | 3-CH₃COOC₆H₄CH₂CH₂<br>COCH₃ | H<br>H | H<br>CH₃ |
| 2BE | 3,4-(CH₃O)₂C₆H₃CH₂CH₂<br>COCH₃ | H<br>H | H<br>CH₃ |
| 2BF | 4-CH₃SC₆H₄CH₂CH₂<br>COCH₃ | H<br>H | H<br>CH₃ |
| 2BG | 3-CF₃C₆H₄CH₂CH₂<br>COCH₃ | H<br>H | H<br>CH₃ |
| 2BH | 3-CH₃CONHC₆H₄CH₂CH₂<br>COCH₃ | H<br>H | H<br>CH₃ |
| 2BJ | 3,4-OCH₂OC₆H₃CH₂CH₂<br>COCH₃ | H<br>H | H<br>CH₃ |
| 2BK | CH₃<br>COCH₃ | H<br>H | H<br>CH₂CH₂SCH₃ |
| 2BL | C₂H₅<br>CO(CH₂)₄CH₃ | CH₃O<br>H | CH₃<br>CH₃ |
| 2BM | CH₃<br>CO(CH₂)₂CH(CH₃)₂ | CH₃O<br>H | CH₃<br>CH₃ |
| 2BN | CH₃<br>CO(CH₂)₂CH(CH₃)₂ | CH₃O<br>H | (CH₂)₄ |

EXAMPLE 2BP

Cyclization of 2,5-dimethyl-3-(3-methylbenzyl)-7-acetyl-2-azabicyclo [2.2.2]oct-5-ene, described in Example 1AV, in the presence of hydrofluoric acid at 0°–15° C. using a procedure similar to that described above in Example 2A affords 1,5α,6-trimethyl-3-acetyl-1,2,3,4,4a,5,10,10a-octahydro-2,5-methanobenzo[g]quinoline.

EXAMPLE 2BQ

Cyclization of ethyl 2-acetyl-3-benzyl-2-azabicyclo-[2.2.2]oct-5-ene-7-carboxylate, described in Example 1BQ, in the presence of hyrofluoric acid at 0°–15° C. using a procedure similar to that described in Example 2A affords ethyl 1-acetyl-1,2,3,4,4a,5,10,10a-octahydro-2,5-methanobenzo[g]quinoline-3-carboxylate.

EXAMPLE 3

A solution containing 21.3 g. (0.05) of ethyl 2,3-dibenzyl-5-ethyl-2-azabicyclo[2.2.2]oct-5-ene-7-carboxylate hydrochloride (described in Example 1B) in 200 ml. of ethanol was reduced over 2.1 g. of palladium-on-charcoal using the procedure described above in Example 1AN. There was thus obtained 18 g. of ethyl 3-benzyl-5-ethyl-2-azabicyclo[2.2.2]-oct-5-ene-7-carboxylate which, without further purification, was dissolved in 170 ml. of 48% hydrobromic acid and heated under reflux for about eight hours. The crude product obtained was recrystallized from water to give 9.4 g. of 5α-ethyl-1,2,3,4,4a,5,10,10a-octahydro-2,5-methanobenzo[g]quinoline-3-carboxylic acid hydrobromide, m.p.>310° C.

EXAMPLE 4

A. A mixture of 48.3 g. (0.13 mole) of 1-methyl-5α-ethyl-1,2,3,4,4a,5,10,10a-octahydro-2,5-methanobenzo[g]quinoline-3-carboxylic acid hydrobromide (described in Example 2A) in 480 ml. of absolute ethanol was treated with anhydrous hydrogen chloride until all material had dissolved. The solution was refluxed for three hours, taken to dryness, and the solid residue was partitioned between dilute ammonium hydroxide and diethyl ether. The ether layer was separated, combined with additional ether washes of the aqueous layer, and the combined organic extracts dried and evaporated to dryness. The resulting solid residue was dissolved in ethanol and treated with ethereal hydrogen chloride to give 39.3 g. of ethyl 1-methyl-5α-ethyl-1,2,3,4,4a,5,10,-10a-octahydro-2,5-methanobenzo[g]quinoline-3-carboxylate hydrochloride, m.p. 244°–246° C.

Following a procedure similar to that described in Example 4A, using an appropriate 7-R₂-1-R₁-4aα-R₃-5α-R₄-1,2,3,4,4a,5,10,10a-octahydro-2,5-methanobenzo[g]quinoline-3-carboxylic acid hydrobromide of formula II and an appropriate lower-alkanol, the corresponding lower-alkyl esters of formula II given in Table 4 below are prepared, where $R_2'$, $R_2''$, $R_2'''$ and $R_8$ in each case are hydrogen. Unless noted otherwise, melting points are given for the free base form.

TABLE 4

| Example | $R_1$/Y | $R_2$ | $R_3$/$R_4$ | Wt.Acid/Wt.Prod. | m.p.(°C.)/Solv. |
|---|---|---|---|---|---|
| 4B | $CH_3$ | H | H | 10.3 | 129–133 |
|  | $COOCH_3$ |  | $CH_3$ | 5.0 | methanol |
| 4C | H | H | H | 11.2 | 245–246 (a) |
|  | $COOC_2H_5$ |  | $C_2H_5$ | 8.0 | ethanol/ether |
| 4D | $CH_3$ | HO | H | 10.0 | 190–193 |
|  | $COOCH_3$ |  | $C_2H_5$ | 5.4 | ethyl acetate/hexane |
| 4E | $C_6H_5CH_2$ | H | $CH_3$ | 18.1 | (b) |
|  | $COOC_3H_7$ |  | $CH_3$ | — |  |

(a) Hydrochloride salt
(b) Not isolated but treated further in Example 6D. Acid (50.3 g.) obtained by saponification of 77.9 g. of compound of Example 2N.

EXAMPLE 5

A. A solution of 53.7 g. (0.15 mole) of 1-benzyl-3-acetyl-5α-methyl-7-methoxy-1,2,3,4,4a,5,10,10a-octahydro-2,5-methanobenzo[g]quinoline (described in Example 2K) in 250 ml. of 48% aqueous hydrobromic acid was warmed on a steam bath for two hours and then filtered and cooled. The solid which had precipitated was collected and recrystallized from water to give 10.3 g. of 1-benzyl-3-acetyl-5α-methyl-7-hydroxy-1,2,3,4,4a,5,10,10a-octahydro-2,5-methanobenzo[g]quinoline hydrobromide, m.p. 192°–197° C.

Following a procedure similar to that described in Example 5A, using an appropriate 6-, 8- or 9-methoxy-3-Y-4aα,5α-dimethyl-1,2,3,4,4a,5,10,10a-octahydro-2,5-methanobenzo[g]quinoline of formula II, the corresponding 6-, 8- or 9-hydroxy compounds of formula II in Table 5 below were prepared, the position of the hydroxy group ($R_2$, $R_2'$, $R_2''$ or $R_2'''$) being given in the column headed "$R_2$ Posn.". In each case $R_1$ is hydrogen, and $R_3$ and $R_4$ are both methyl. The compounds were prepared from the hydrochloride salts and, unless indicated otherwise, were isolated as the methanesulfonates.

TABLE 5

| Example | Y | $R_2$ Posn. | Wt.S.M./Wt.Prod. | m.p.(°C.)/Solv. |
|---|---|---|---|---|
| 5B | $COOC_2H_5$ | 8-HO | 6.2 | 275–277 |
|  |  |  | 2.8 | ethanol |
| 5C | $COOC_2H_5$ | 6-HO | 7.0 | 219–221 |
|  |  |  | 3.2 | acetone |
| 5D | $COOC_2H_5$ | 9-HO | 16.5 | 255–257(a) |
|  |  |  | 2.4(a) | ethanol/ether |

(a) Hydrochloride salt

EXAMPLE 6

A. A solution of 21.7 g. (0.06 mole) of 1-benzyl-3-acetyl-5α-ethyl-1,2,3,4,4a,5,10,10a-octahydro-2,5-methanobenzo[g]quinoline (described in Example 2E) in 100 ml. of ethanol was made acidic with aqueous hydrochloric acid, and the solution was reduced with hydrogen over 2.0 g. of 10% palladium-on-charcoal at room temperature using a Parr shaking apparatus. When reduction was complete, the catalyst was removed by filtration, the filtrate concentrated to dryness in vacuo, and the residue recrystallized from isopropanol to give 14.4 g. of 3-acetyl-5α-ethyl-1,2,3,4,4a,5,10,10a-octahydro-2,5-methanobenzo[g]quinoline hydrochloride, m.p. 240°–241° C.

Following a procedure similar to that described in Example 6A, using an appropriate 6-$R_2''$-7-$R_2$-8-$R_2'$-9-$R_2'''$-1-benzyl-3-Y-4aα-$R_3$-5α-$R_4$-1,2,3,4,4a,5,10,10a-octahydro-2,5-methanobenzo[g]quinoline of formula II, the corresponding debenzylated compounds of formula II in Table 6 below were prepared, where $R_1$ and $R_8$ in each case are hydrogen. The position of the $R_2$, $R_2'$, $R_2''$ or $R_2'''$ group when other than hydrogen is given in the column headed "$R_2$ Posn.". The compounds were prepared from, and isolated as, either the hydrobromide, the hydrochloride or the free base as indicated.

TABLE 6

| Example | Y | $R_2$Posn. | $R_3$/$R_4$ | Wt.S.M./Wt.Prod. | m.p.(°C.)/Solv. |
|---|---|---|---|---|---|
| 6B | $COCH_3$ | 7-HO | H | 8.2 (HBr) | 247–248 |
|  |  |  | $CH_3$ | 4.8 (HBr) | acetonitrile |
| 6C | $COOC_2H_5$ | — | $CH_3$ | 42.6 (HCl) | 213–216 |
|  |  |  | $CH_3$ | 26.4 (HCl) | ethanol/ether |
| 6D | $COOC_3H_7$ | — | $CH_3$ | (a) | 213–215 |
|  |  |  | $CH_3$ | 13.6 (HCl) | acetonitrile |
| 6E | $COOC_2H_5$ | — | $CH_3$ | 16.1 (base) | 226–229 |
|  |  |  | $C_2H_5$ | 9.0 (HCl) | ethanol/ether |
| 6F | $COOC_2H_5$ | — | H | 18.8 (base) | 213–214 |
|  |  |  | $CH_3$ | 11.9 (HCl) | ethanol/ether |
| 6G | $COOC_2H_5$ | — | $C_2H_5$ | 22.0 (HCl) | 150–151 |
|  |  |  | $CH_3$ | 12.6 (HCl) | ether |
| 6H | $COOCH_3$(b) | — | $CH_3$ | 15.0 (base)(b) | 221–223 |
|  |  |  | $CH_3$ | 7.5 (HCl) | ethanol/ether |
| 6J | $COOC_2H_5$ | 7-$CH_3O$ | $CH_3$ | 21.0 (base) | 202–203 |
|  |  |  | $CH_3$ | 14.2 (HCl) | acetone/ether |
| 6K | $COOC_2H_5$ | 7-HO(c) | $CH_3$ | 21.0 (base) | 185–187 |
|  |  |  | $CH_3$ | 8.0 (base) | ethyl acetate |
| 6L | $COOC_2H_5$ | 8-$CH_3O$ | $CH_3$ | 15.0 (base) | 226–228 |
|  |  |  | $CH_3$ | 11.2 (HCl) | acetone |
| 6M | $COOC_2H_5$ | 6-$CH_3O$ | $CH_3$ | 16.3 (HCl) | 227–228 |
|  |  |  | $CH_3$ | 10.3 (HCl) | acetone |
| 6N | $COOC_2H_5$ | 9-$CH_3O$ | $CH_3$ | 20.0 (HCl) | 261–262 |
|  |  |  | $CH_3$ | 13.3 (HCl) | ethanol/ether |

(a) Reaction carried out on product of Example 4E without isolation of the latter.
(b) Prepared by saponification of 61.1 g. of the compound of Example 2N (36.9 g. of free base of the carboxylic acid, m.p. 178°–185° C. obtained) and reesterification of the acid with methanol. Debenzylation carried out on the product directly without isolation.
(c) The crude product, without isolation, was cleaved with boiling 48% hydrobromic acid using the procedure described in Example 5.

EXAMPLE 7

A. A mixture of 5.0 g. (0.017 mole) of ethyl 5α-ethyl-1,2,3,4,4a,5,10,10a-octahydro-2,5-methanobenzo[g]quinoline-3-carboxylate hydrochloride (described in Example 4C), 2.8 g. (0.17 mole) of cyclopropylmethyl bromide and 1.4 g. (0.017 mole) of sodium bicarbonate in 40 ml. of DMF was stirred and refluxed for three hours, and then evaporated to dryness in vacuo. The residue was partitioned between water and diethyl ether, the ether layer was washed with water, dried, charcoaled and filtered, and the filtrate was diluted with ethanol and acidified with ethereal hydrogen chloride. The solid which separated was collected and recrystallized from ethanol/ether to give 4.4 g. of ethyl 1-cyclopropylmethyl-5α-ethyl-1,2,3,4,4a,5,10,10a-octahydro-2,5-methanobenzo[g]quinoline-3-carboxylate hydrochloride, m.p. 215°-217° C.

Following a procedure similar to that described in Example 7A, using an appropriate alkylating agent and an appropriate 3-Y-4aα-R₃-5α-R₄-1,2,3,4,4a,5,10,10a-octahydro-2,5-methanobenzo[g]quinoline, the following compounds of formula II in Table 7 were prepared, where in each case, unless noted otherwise, $R_2$, $R_2'$, $R_2''$, $R_2'''$ and $R_8$ are each hydrogen. The form of the starting materials and the products, whether free base or a particular salt form, is indicated in each case.

late with cyclopropylmethyl bromide in DMF in the presence of sodium carbonate using the procedure described above in Example 7A affords ethyl 1-cyclopropylmethyl-4aα,5α-dimethyl-7-methoxy-1,2,3,4,4a,5,10,10a-octahydro-2,5-methanobenzo[g]quinoline-3-carboxylate.

EXAMPLE 8

A. A mixture of 18.0 g. (0.05 mole) of 5α-ethyl-1,2,3,4,4a,5,10,10a-octahydro-2,5-methanobenzo[g]quinoline-3-carboxylic acid hydrobromide (described in Example 3), 20.4 g. (0.11 mole) of β-phenylethyl bromide and 13.5 g. (0.16 mole) of sodium bicarbonate in 200 ml. of DMF was stirred under reflux for four hours, and then worked up in the manner described above in Example 7A. The crude product was converted to the hydrochloride salt which was recrystallized from isopropanol to give 4.4 g. of 2-phenylethyl 1-(2-phenylethyl)-5α-ethyl-1,2,3,4,4a,5,10,10a-octahydro-2,5-methanobenzo[g]quinoline-3-carboxylate hydrochloride, m.p. 237°-238° C.

B. Following a procedure similar to that described in Example 8A, 20.5 g. (0.058 mole) of 5α-ethyl-1,2,3,4,4a,5,10,10a-octahydro-2,5-methanobenzo[g]quinoline-3-carboxylic acid hydrobromide (described in Example 3) was reacted with 19.8 g. (0.12 mole) of cyclopropylmethyl bromide in the presence of sodium bicarbonate, and the product converted to the hydrochloride salt which was recrystallized from ethanol/ether to give 6.6 g. of cyclopropylmethyl 1-cyclopropylmethyl-5α-ethyl-1,2,3,4,4a,5,10,10a-octahydro-2,5-methanobenzo[g]quinoline-3-carboxylate hydrolchloride, m.p. 184°-187° C.

| Example | $R_1/Y$ | $R_3/R_4$ | Wt. S.M./Wt. Prod. | m.p. (°C.)/Solv. |
|---|---|---|---|---|
| 7B | cyclopropyl-CH₂ | H | 27.6 (HCl) | 202-204 |
| | COCH₃ | C₂H₅ | 24.1 (HCl) | ethanol/ether |
| 7C | C₆H₅CH₂CH₂ | CH₃ | 11.3 (base) | 173-174 |
| | COOC₂H₅ | CH₃ | 5.9 (CH₃SO₃H) | ethyl acetate/ether |
| 7D | C₂H₅ | CH₃ | 11.0 (HCl) | 218-219 |
| | COOC₂H₅ | CH₃ | 7.4 (HCl) | acetone |
| 7E | n-C₃H₇ | CH₃ | 11.0 (HCl) | 210-213 |
| | COOC₂H₅ | CH₃ | 8.7 (HCl) | acetone |
| 7F | n-C₄H₉ | CH₃ | 11.0 (HCl) | 213-216 |
| | COOC₂H₅ | CH₃ | 7.2 (HCl) | acetone |
| 7G | n-C₅H₁₁ | CH₃ | 11.0 (HCl) | 200-203 |
| | COOC₂H₅ | CH₃ | 7.8 (HCl) | acetone |
| 7H | CH₂CH=CH₂ | CH₃ | 6.0 (base) | 120-123 |
| | COOC₂H₅ | CH₃ | 5.3 (HCl) | acetone |
| 7J | CH₂CH=C(CH₃)₂ | CH₃ | 8.6 (base) | 196-199 |
| | COOC₂H₅ | CH₃ | 7.8 (HCl) | acetone |
| 7K | cyclopropyl-CH₂ | CH₃ | 7.5 (base) | 213-215 |
| | COOC₂H₅ | CH₃ | 6.2 (HCl) | acetone |
| 7L | CH₂C≡CH | CH₃ | 7.5 (base) | 184-186 |
| | COOC₂H₅ | CH₃ | 5.8 (HCl) | ethanol/ether |
| 7M | cyclobutyl-CH₂ | CH₃ | 6.6 (base) | 217-219 |
| | COOC₂H₅ | CH₃ | 1.2 (HCl) | acetone |
| 7N | 3-furyl-CH₂ | CH₃ | 7.5 (base) | 213-215 |
| | COOC₂H₅ | CH₃ | 5.5 (HCl) | ethanol |
| 7P | CH₃ (a) | CH₃ | 27.6 (base) | 235-238 |
| | COOC₂H₅ | CH₃ | 14.5 (HCl) | ethanol/ether |
| 7Q | CH₃ (a) (b) | CH₃ | 9.0 (base) | 200-202 |
| | COOC₂H₅ | CH₃ | 2.7 (HCl) | acetone/ether |
| 7R | CH₃ (a) (c) | CH₃ | 20.5 (base) | 98-100 |
| | COOC₂H₅ | CH₃ | 22.9 (base) | hexane |

(a) Prepared by warming the starting material of formula II with a molar excess each of formic acid and 37% aqueous formaldehyde.
(b) Product is ethyl 1,3,4aα,5α-tetramethyl-1,2,3,4,4a,5,10,10a-octahydro-2,5-methanobenzo[g]quinoline-3-carboxylate prepared from the 3-methyl-3-carboxylate described in Example 17.
(c) R₂ is CH₃O.

EXAMPLE 7S

Debenzylation of the ethyl 1-benzyl-4aα,5α-dimethyl-7-methoxy-1,2,3,4,4a,5,10,10a-octahydro-2,5-methanobenzo[g]quinoline-3-carboxylate described above in Example 2AA using the procedure described above in Example 6A and alkylation of the resulting ethyl 4aα,5α-dimethyl-7-methoxy-1,2,3,4,4a,5,10,10a-octahydro-2,5-methanobenzo[g]quinoline-3-carboxy-

EXAMPLE 9

A. A solution of 0.035 mole of ethyl 1-methyl-5α-propyl-1,2,3,4,4a,5,10,10a-octahydro-2,5-methanobenzo[g]quinoline-3-carboxylate (obtained from 14.4 g. of the corresponding hydrochloride described above in Example 2J) in diethyl ether was added in a fine stream to 81 ml. of a 2.16 M solution (0.175 mole) of methyl lithium in diethyl ether. When addition was complete, the mixture was stirred for about thirty minutes, allowed to stand overnight, and then poured into an ice/aqueous ammonium chloride mixture. The ether layer was separated, the aqueous layer washed with diethyl ether, and the combined organic extracts washed with saturated brine, dried, filtered, and concentrated to dryness. The residue was dissolved in ethanol/ether, and the solution acidified with ethereal hydrogen chloride. The solid which separated was collected and recrystallized from ethanol/ether to give 2.5 g. of 1-methyl-3-(2-hydroxy-2-propyl)-5α-propyl-1,2,3,4,4a,5,10,10a-octahydro-2,5-methanobenzo[g]quinoline hydrochloride, m.p. 257°–258° C.

Following a procedure similar to that described in Example 9A, using an appropriate lower-alkyl 7-$R_2$-1-$R_1$-4aα-$R_3$-5α-$R_4$-1,2,3,4,4a,5,10,10a-octahydro-2,5-methanobenzo[g]quinoline-3-carboxylate of formula II described in Examples 4A, 4B, 4D, 8A, 2M, 7A and 2N, respectively, and methyl lithium, the following compounds of formula II in Table 9, where in each case Y is $C(CH_3)_2OH$ and $R_2'$, $R_2''$, $R_2'''$ and $R_8$ are hydrogen, are prepared. In each case, the weights of starting materials are given for the free base form, and unless noted otherwise, melting points of the products are given for the hydrochloride salt.

EXAMPLE 10

A. To a suspension of 44.1 g. (0.16 mole) of 1-methyl-5α-ethyl-1,2,3,4,4a,5,10,10a-octahydro-2,5-methanobenzo[g]-quinoline-3-carboxylic acid (from the hydrobromide described in Example 2A) in 390 ml. of diethyl ether was added in a fine stream 230 ml. (0.5 mole) of a 2.16 M solution of methyl lithium in diethyl ether. When addition was complete, the mixture was stirred for three hours, poured into an ice/aqueous ammonium chloride solution, and worked up in the manner described in Example 9A. There was thus obtained 32.8 g. of product as an oily crude base, 3.3 g. of which was converted to the hydrochloride salt. The latter was recrystallized from methanol/diethyl ether to give 2.3 g. of 1-methyl-3-acetyl-5α-ethyl-1,2,3,4,4a,5,10,10a-octahydro-2,5-methanobenzo[g]quinoline hydrochloride, m.p. 191° C.

Following a procedure similar to that described in Example 10A, using an appropriate 7-$R_2$-1-$R_1$-4aα-$R_3$-5α-$R_4$-1,2,3,4,4a,5,10,10a-octahydro-2,5-methanobenzo[g]quinoline-3-carboxylic acid of formula II described in Examples 2A, 2C, 2M, 2F and 2AA and an appropriate organo lithium, $R_5Li$, the following compounds of formula II in Table 10a were prepared, where in each case $R_2'$, $R_2''$, $R_2'''$ and $R_8$ are hydrogen. The form (salt or base) of the starting material is given in each case in parentheses along with the weight of starting material, and, of course, salt forms were converted to the free base before reaction with the organo lithium. The melting points for the compounds of Examples 10B and 10D are given for the hydrochloride salts and for the free base of the compounds of Examples 10C, 10E, 10H and 10J.

TABLE 9

| Example | $R_1$ | $R_2$ | $R_3/R_4$ | Wt. S.M./Wt. Prod. | m.p. (°C.)/Solv. |
|---|---|---|---|---|---|
| 9B | $CH_3$ | H | H | 15.7 | 275 |
| | | | $C_2H_5$ | 6.9 | ethanol |
| 9C | $CH_3$ | H | H | 15 | 256–257 |
| | | | $CH_3$ | 12.2 | ethanol/ether |
| 9D | $CH_3$ | HO | H | 12.9 | 272 |
| | | | $C_2H_5$ | 8.1 | ethanol/ether |
| 9E | $C_6H_5CH_2CH_2$ | H | H | 8.2 | 248–248.5 |
| | | | $C_2H_5$ | 3.9 | ethanol/ether |
| 9F | $CH_3$ | $CH_3O$ | H | 25 | 126–127 (a) |
| | | | $CH_3$ | 22.1 | hexane |
| 9G | $C_3H_5-CH_2$ (b) | H | H | 6.1 | 256 |
| | | | $C_2H_5$ | 4.5 | ethanol/ether |
| 9H | H (c) | H | $CH_3$ | 13.7 | 152–153 (a) |
| | | | $CH_3$ | 4.4 | isopropyl acetate/hexane |

(a) Free base
(b) Cyclopropylmethyl
(c) Product debenzylated without isolation using the procedure of Example 6A.

TABLE 10a

| Example | $R_1/COR_5$ | $R_2$ | $R_3/R_4$ | Wt. S.M./Wt. Prod. | m.p. (°C.)Solv. |
|---|---|---|---|---|---|
| 10B | $CH_3$ | H | H | 12.1 (base) | 190–191 |
| | $COC_3H_7$ | | $C_2H_5$ | 8.0 (HCl) | isopropanol/ether |
| 10C | $CH_3$ | HO | H | 36 (HBr) | 201–204 |
| | $COCH_3$ | | $C_2H_5$ | 18.9 (base) | $DMF/H_2O$ |
| 10D | $CH_3$ | H | H | 8.6 (base) | 200–202 |
| | $COC_6H_5$ | | $C_2H_5$ | 6.4 (HCl) | ethanol/ether |
| 10E | $CH_3$ | $CH_3O$ | H | 18 (base) | 65–67 |
| | $COC_5H_{11}$ | | $CH_3$ | 6.3 (base) | ethanol |
| 10F | $C_6H_5CH_2$ | H | $CH_3$ | 59.8 (base) | — |
| | $COCH_3$ | | $CH_3$ | 55.3 (base) | — |
| 10G | $CH_3$ | $CH_3O$ | $CH_3$ | 27.8 (base) | 130 |
| | $C(OH)(C_5H_{11})_2$ (a) | | $CH_3$ | 2.3 (HCl) | acetone/ether |
| 10H | $C_6H_5CH_2$ | $CH_3O$ | H | 60 (HCl) (b) | 146–151 |
| | $COC(CH_3)_3$ | | $CH_3$ | 25.2 (base) | ethanol |

TABLE 10a-continued

| Example | $R_1$/$COR_5$ | $R_2$ | $R_3$/$R_4$ | Wt. S.M./Wt. Prod. | m.p. (°C.)Solv. |
|---|---|---|---|---|---|
| 10J | $C_6H_5CH_2$ | $CH_3O$ | $CH_3$ | 4.2 (base) (b) | 112–115 |
|  | $COC(CH_3)_3$ |  | $CH_3$ | 1.6 (base) | ethanol |

(a) Product isolated was result of reaction of three moles of amyl lithium per mole of carboxylic acid, i.e. 1,4aα,5α-trimethyl-7-methoxy-3-(6-hydroxy-6-undecyl)-1,2,3,4,4a,5,10,10a-octahydro-2,5-methanobenzo[g]quinoline hydrochloride.
(b) Starting material was ethyl 3-carboxylate ester.

Following a procedure similar to that described in Example 10A, using an appropriate 7-$R_2$-1-$R_1$-4aα-$R_3$-5α-$R_4$-1,2,3,4,4a,5,10,10a-octahydro-2,5-methanobenzo[g]quinoline-3-carboxylic acid (prepared by alkaline saponification of the corresponding esters described above) and an appropriate loweralkyl or cycloalkyl-lower-alkyl lithium, the following compounds of formula II in Table 10b are prepared where, in each case, $R_2'$, $R_2''$, $R_2'''$ and $R_8$ are each hydrogen.

TABLE 10b

| Example | $R_1$/Y | $R_2$ | $R_3$/$R_4$ |
|---|---|---|---|
| 10K | $CH_3$ | H | H |
|  | $COCH_3$ |  | $CH_2CH_2SC_6H_5$ |
| 10L | $CH_3$ | H | H |
|  | $CH(CH_3)$ |  | $CH_2CH_2SOC_6H_5$ |
| 10M | $CH_3$ | H | H |
|  | $COCH_3$ |  | $CH=CH_2$ |
| 10N | $CH_3$ | H | H |
|  | $COCH_3$ |  | $CH_2CH_2OH$ |
| 10P | $CH_3$ | $CH_3O$ | $CH_3$ |
|  | $COCH_2CH_3$ |  | $CH_3$ |
| 10Q | $CH_3$ | $CH_3O$ | $CH_3$ |
|  | $CO(CH_2)_2CH_3$ |  | $CH_3$ |
| 10R | $C_3H_5-CH_2$ | $CH_3O$ | $CH_3$ |
|  | $CO(CH_2)_3CH_3$ |  | $CH_3$ |
| 10S | $CH_3$ | $CH_3O$ | H |
|  | $CO(CH_2)_3CH_3$ |  | $CH_3$ |
| 10T | $C_6H_5CH_2$ | $CH_3O$ | $CH_3$ |
|  | $CO(CH_2)_3CH_3$ |  | $CH_3$ |
| 10U | $CH_3$ | $CH_3O$ | $CH_3$ |
|  | $COCH_2CH(CH_3)_2$ |  | $CH_3$ |
| 10V | $C_6H_5CH_2$ | H | $CH_3$ |
|  | $CO(CH_2)_4CH_3$ |  | $CH_3$ |
| 10W | $C_6H_5CH_2$ | $CH_3O$ | $CH_3$ |
|  | $CO(CH_2)_4CH_3$ |  | $CH_3$ |
| 10X | $CH_3$ | $CH_3O$ | $CH_3$ |
|  | $CO(CH_2)_2(CH_3)_2$ |  | $CH_3$ |
| 10Y | $CH_3$ | $CH_3O$ | $CH_3$ |
|  | $CO(CH_2)_5CH_3$ |  | $CH_3$ |
| 10Z | $CH_3$ | $CH_3O$ | $CH_3$ |
|  | $COCH_2$—cyclopropyl |  | $CH_3$ |
| 10AA | $CH_3$ | $CH_3O$ | $CH_3$ |
|  | $CO(CH_2)_2$—cyclopropyl |  | $CH_3$ |
| 10AB | $CH_3$ | $CH_3O$ | $CH_3$ |
|  | $COCH_2$—cyclobutyl |  | $CH_3$ |
| 10AC | $CH_3$ | $CH_3O$ | $CH_3$ |
|  | $CO(CH_2)_2$—cyclobutyl |  | $CH_3$ |
| 10AD | $CH_3$ | $CH_3O$ | $CH_3$ |
|  | $COCH_2$—cyclopentyl |  | $CH_3$ |
| 10AE | $CH_3$ | $CH_3O$ | $CH_3$ |
|  | $CO(CH_2)_2$—cyclopentyl |  | $CH_3$ |
| 10AF | $CH_3$ | $CH_3O$ | $CH_3$ |
|  | $COCH_2$—cyclohexyl |  | $CH_3$ |
| 10AG | $CH_3$ | $CH_3O$ | $CH_3$ |
|  | $CO(CH_2)_2$—cyclohexyl |  | $CH_3$ |
| 10AH | $CH_3$ | $CH_3O$ | $CH_3$ |
|  | $CO(CH_2)_2CH_3$ |  | $CH_3$ |
| 10AJ | $CH_3$ | $CH_3O$ | $CH_3$ |
|  | $CO(CH_2)_2C_6H_5$ |  | $CH_3$ |
| 10AK | $CH_3CO$ | H | H |
|  | $CO(CH_2)_3CH_3$ |  | H |
| 10AL | $CH_3$ | H | $CH_3$ |
|  | $CO(CH_2)_2$—cyclopentyl |  | $CH_3$ |
| 10AM | $CH_3$ | $CH_3O$ | $CH_3$ |
|  | $COCH_2C_6H_5$ |  | $CH_3$ |
| 10AN | $CH_3$ | H | $CH_3$ |
|  | $COC_6H_5$ |  | $CH_3$ |
| 10AP | $CH_3$ | $CH_3O$ | $CH_3$ |
|  | $COC_6H_5$ |  | $CH_3$ |
| 10AQ | $CH_3$ | $CH_3O$ | $CH_3$ |
|  | $COC_6H_4CH_3^{(3)}$ |  | $CH_3$ |
| 10AR | $CH_3$ | $CH_3O$ | $CH_3$ |
|  | $COC_6H_4CH_3^{(4)}$ |  | $CH_3$ |
| 10AS | $CH_3$ | $CH_3O$ | $CH_3$ |
|  | $COCH_3$ |  | $CH_3$ |
| 10AT | $CH_3$ | H | $CH_3$ |
|  | $CO(CH_2)_4CH_3$ |  | $CH_3$ |
| 10AU | $CH_3$ | $CH_3O$ | $CH_3$ |
|  | $CO(CH_2)_4CH_3$ |  | $C_2H_5$ |
| 10AV | $CH_3$ | H | $CH_3$ |
|  | $CO(CH_2)_2CH(CH_3)_2$ |  | $CH_3$ |
| 10AW | $C_6H_5CH_2$ | $CH_3O$ | $CH_3$ |
|  | $CO(CH_2)_2CH(CH_3)_2$ |  | $CH_3$ |
| 10AX | $CH_3$ | $CH_3O$ | H |
|  | $CO(CH_2)_2CH(CH_3)_2$ |  | $CH_3$ |
| 10AY | $CH_3$ | $CH_3O$ | $CH_3$ |
|  | $CO(CH_2)_2CH(CH_3)_2$ |  | $C_2H_5$ |
| 10AZ | $CH_3$ | $CH_3O$ |  |
|  | $CO(CH_2)_2CH(CH_3)_2$ |  | $\mid$<br>$(CH_2)_4$<br>$\mid$ |
| 10BA | $CH_3$ | $CH_3O$ | $CH_3$ |
|  | $CO(CH_2)_3CH(CH_3)_2$ |  | $CH_3$ |
| 10BB | $CH_3$ | $CH_3O$ | $CH_3$ |
|  | $CO(CH_2)_3CH(CH_3)_2$ |  | $CH_3$ |

EXAMPLE 11

A. A solution of 2.8 g. (0.01 mole) of 1-methyl-3-acetyl-5α-ethyl-1,2,3,4,4a,5,10,10a-octahydro-2,5-methanobenzo[g]quinoline (from the hydrochloride described in Example 10A) in 25 ml. of diethyl ether was added dropwise to a solution of 40 ml. (0.032 mole) of a 0.8 M solution of propyl lithium in diethyl ether. When addition was complete, the mixture was allowed to stand for one hour, poured into an ice/aqueous ammonium chloride solution and worked up in the manner described in Example 9A. The product thus obtained was converted to the hydrochloride salt which was recrystallized from ethanol/ether to give 1.2 g. of 1-methyl-3-(2-hydroxy-2-pentyl)-5α-ethyl-1,2,3,4,4a,5,10,10a-octahydro-2,5-methano-benzo[g]quinoline hydrochloride, m.p. 227°–230° C. (designated isomer A).

B. The compound, 1-methyl-3-(2-hydroxy-2-pentyl)-5α-ethyl-1,2,3,4,4a,5,10,10a-octahydro-2,5-methanobenzo[g]quinoline, m.p. 103°–105° C. (from hexane) (the hydrochloride salt shows m.p. 263°–265° C., from isopropanol/DMF), isomeric in the configuration of the 3-(2-hydroxy-2-pentyl) group with isomer A above and designated isomer B, was prepared in a similar fashion by reaction of 1-methyl-3-butyryl-5α-ethyl-1,2,3,4,4a,5,10,10a-octahydro-2,5-methanobenzo[g]quinoline (from the hydrochloride salt described in Example 10B) with methyl lithium.

Following a procedure similar to that described in Example 11A, using an appropriate 7-$R_2$-1-$R_1$-3-acetyl-4aα-$R_3$-5α-$R_4$-1,2,3,4,4a,5,10,10a-octahydro-2,5-methanobenzo[g]quinoline described in Examples 2G and 2K, respectively, and methyl lithium, the following compounds of formula II in Table 11 were prepared where, in each case, Y is C(CH$_3$)$_2$OH and R$_2'$, R$_2''$, R$_2'''$ and R$_8$ are each hydrogen. All melting points are for the hydrochloride salts.

TABLE 11

| Example | R$_1$ | R$_2$ | R$_3$/R$_4$ | Wt. S.M./ Wt. Prod. | m.p. (°C.)/Solv. |
|---|---|---|---|---|---|
| 11C | CH$_3$ | H | CH$_3$<br>C$_2$H$_5$ | 5.0 (base)<br>4.4 | 247–248<br>ethanol/ether |
| 11D | C$_6$H$_5$CH$_2$ | CH$_3$O | H<br>CH$_3$ | 15.0 (base)<br>12.2 | 236–237<br>ethanol/ether |

EXAMPLE 12

A. A solution of 0.076 mole of ethyl 1-methyl-5α-ethyl-1,2,3,4,4a,5,10,10a-octahydro-2,5-methanobenzo[g]quinoline-3-carboxylate (obtained from 26.7 g. of the hydrochloride salt described in Example 4A) in 250 ml. of anhydrous diethyl ether was added in a fine stream to a stirred suspension of 2.9 g. (0.076 mole) of lithium aluminum hydride in 125 ml. of diethyl ether. When addition was complete, the mixture was stirred for about one hour, treated dropwise with 5.8 ml. of water, stirred for an additional ten minutes, and then filtered through filter aid. The filter cake was washed with several portions of diethyl ether, and the combined filtrates were evaporated to dryness to give 20.8 g. of the product in the form of the free base, 7.0 g. of which was dissolved in 35 ml. of ethanol and acidified with ethereal hydrogen chloride. The solid which separated was collected and recrystallized from ethanol/diethyl ether to give 7.6 g. of 1-methyl-3-hydroxymethyl-5α-ethyl-1,2,3,4,4a,5,10,10a-octahydro-2,5-methanobenzo[g]quinoline hydrochloride, m.p. 273°–278° C.

Following a procedure similar to that described in Example 12A using the ethyl 1-methyl-4aα,5α-dimethyl-1,2,3,4,4a,5,10,10a-octahydro-2,5-methanobenzo[g]quinoline-3-carboxylates described in Examples 7P, 2W and 7Q, respectively, there were obtained the following compounds of formula II where in each instance R$_1$, R$_3$ and R$_4$ are each CH$_3$ and R$_2$, R$_2'$, R$_2''$ and R$_2'''$ are each hydrogen. The products were isolated and characterized as the hydrochloride salts.

TABLE 12

| Example | Y/R$_8$ | Wt. S.M./ Wt. Prod. | m.p. (°C.)/Solv. |
|---|---|---|---|
| 12B | CH$_2$OH (Isomer A)<br>H | 10.5 (base)<br>7.5 | 245–247<br>ethanol/ether |
| 12C | CH$_2$OH (Isomer B)<br>H | 13.4 (base)<br>10.6 | 270–274<br>ethanol/ether |
| 12D | CH$_2$OH<br>CH$_3$ | 3.8 (base)<br>2.5 | 232–234<br>ethanol/ether |

EXAMPLE 13

A. A solution of 8.5 g. (0.3 mole) of 1-methyl-3-acetyl-5α-ethyl-1,2,3,4,4a,5,10,10a-octahydro-2,5-methanobenzo[g]quinoline hydrochloride (described in Example 10A) in 135 ml. of ethanol was added in a fine stream to a solution of 1.2 g. (0.03 mole) of sodium borohydride in 25 ml. of ethanol. When addition was complete, the mixture was stirred for four and one half hours and then decanted from the precipitated solids. The liquid layer was evaporated to dryness, the residue dissolved in dilute hydrochloric acid and the solution basified with concentrated ammonium hydroxide. Extraction of the mixture with diethyl ether afforded 7.5 g. of crude base which was converted to the hydrochloride salt to give 3.3 g. of 1-methyl-3-(1-hydroxyethyl)-5α-ethyl-1,2,3,4,4a,5,10,10a-octahydro-2,5-methanobenzo[g]quinoline hydrochloride, m.p. 305°–307° C.

Following a procedure similar to that described in Example 13A, using the lower-alkyl 1-R$_1$-4aα-R$_3$-5α-R$_4$-7-R$_2$-1,2,3,4,4a,5,10,10a-octahydro-2,5-methanobenzo[g]quinoline-3-carboxylates described in Examples 2M and 6D, respectively, there are obtained the following compounds of formula II where R$_2'$, R$_2''$, R$_2'''$ and R$_8$ in each case is hydrogen. The compounds were prepared from the free bases and the products isolated and characterized either as the free base or the hydrochloride salt as indicated.

TABLE 13

| Example | R$_1$/Y | R$_2$ | R$_3$/R$_4$ | Wt. S.M./ Wt. Prod. | m.p. (°C.)/ Solv. |
|---|---|---|---|---|---|
| 13B | CH$_3$<br>CH$_2$OH | CH$_3$O | H<br>CH$_3$ | 25.0<br>21.4 (HCl) | 264–268<br>ethanol/ether |
| 13C | H<br>CH$_2$OH | H | CH$_3$<br>CH$_3$ | 15.2<br>3.7 (base) | 165–166<br>isopropyl acetate/hexane |

EXAMPLE 14

A. A solution of 4.8 g. (0.018 mole) of 1-methyl-3-hydroxymethyl-5α-ethyl-1,2,3,4,4a,5,10,10a-octahydro-2,5-methanobenzo[g]quinoline hydrochloride (described in Example 12A) in 50 ml. of pyridine was treated with 4.8 g. (0.02 mole) of 3,4,5-trimethoxybenzoyl chloride, the solution heated on a steam bath for six and one half hours and then allowed to stand overnight. The solid material which had separated was collected and recrystallized from ethanol/ether to give 7.1 g. of 1-methyl-3-(3,4,5-trimethoxybenzoyloxymethyl)-5α-ethyl-1,2,3,4,4a,5,10,10a-octahydro-2,5-methanobenzo[g]quinoline hydrochloride, m.p. 247°–249° C.

B. Following a procedure similar to that described in Example 14A, using 7.9 g. (0.029 mole) of the 1-methyl-3-hydroxymethyl-5α-ethyl-1,2,3,4,4a,5,10,10a-octahydro-2,5-methanobenzo[g]quinoline described in Example 12A and 80 ml. of propionic anhydride, and isolation of the product in the form of the hydrochloride salt, there was obtained 3.9 g. of 1-methyl-3-propionyloxymethyl-5α-ethyl-1,2,3,4,4a,5,10,10a-octahydro-2,5-methanobenzo[g]quinoline hydrochloride, m.p. 264°–266° C. (from ethanol/ether).

Following a procedure similar to that described in Example 14A using the 1-methyl-3-hydroxymethyl-5α-ethyl-1,2,3,4,4a,5,10,10a-octahydro-2,5-methanobenzo[g]quinoline described in Example 12A and an appropriate acid chloride in the presence of pyridine, the following compounds of formula II described in Table 14 are prepared where, in each instance, R$_1$ is CH$_3$; R$_2$, R$_2'$, R$_2''$, R$_2'''$, R$_3$ and R$_8$ are hydrogen; R$_4$ is C$_2$H$_5$; and Y is CH$_2$OR$_7$.

TABLE 14

| Example | R$_7$ |
|---|---|
| 14C | 4-CH$_3$C$_6$H$_4$CO |
| 14D | 4-HOC$_6$H$_4$CO |
| 14E | 3-ClC$_6$H$_4$CO |
| 14F | 3-BrC$_6$H$_4$CO |
| 14G | 3-FC$_6$H$_4$CO |
| 14H | 3-CF$_3$C$_6$H$_4$CO |

EXAMPLE 15

A. A solution of 427 g. (0.97 mole) of ethyl 2-benzyl-3-(4-methoxybenzyl)-5-methyl-2-azabicyclo[2.2.2]oct-5-ene-7-carboxylate hydrochloride (described in Example 1H) was dissolved in 1800 ml. of ethanol and reduced in two portions with hydrogen over 10 g. of palladium-on-charcoal. The product was worked up in the manner described above in Example 1AN to give 273 g. of ethyl 3-(4-methoxybenzyl)-5-methyl-2-azabicyclo[2.2.2]oct-5-ene-7-carboxylate.

The latter was dissolved in 700 ml. of dry ethanol, and the solution added to a solution of 11 g. (0.48 mole) of sodium dissolved in 2 liters of dry ethanol. The resulting solution was stirred and refluxed for seventy-two hours, treated with 39 ml. of glacial acetic acid, cooled to room temperature and filtered through filter aid. The solution was evaporated to dryness, the solid residue was refluxed with ethyl acetate, the mixture was filtered, and the filtrate diluted with hexane to give one crop of 75 g. of product, m.p. 130° C. The filtrate, on extraction with dilute mineral acid, evaporation to dryness and recrystallization of the residue from ethyl acetate/hexane gave an additional 23 g. of product (total yield 98 g.), 2-(4-methoxybenzyl)-8-methylene-3-azabicyclo[3.3.1]non-6-en-4-one. A small sample, recrystallized twice from ethyl acetate/hexane, gave material having m.p. 132°–133° C.

B. Following a procedure similar to that described in Example 15A, catalytic debenzylation of the ethyl 2,3-dibenzyl-5-methyl-2-azabicyclo[2.2.2]oct-5-ene-7-carboxylate hydrochloride described in Example 1F and base catalyzed rearrangement of the resulting ethyl 3-benzyl-5-methyl-2-azabicyclo[2.2.2]oct-5-ene-7-carboxylate affords 2-benzyl-8-methylene-3-azabicyclo[3.3.1]non-6-en-4-one.

EXAMPLE 16

To a solution of 0.15 mole of sodium ethoxide (prepared by dissolving 3.5 g. of sodium in 250 ml. of absolute ethanol) was added 28.5 g. (0.095 mole) of ethyl 4a$\alpha$,5$\alpha$-dimethyl-1,2,3,4,4a,5,10,10a-octahydro-2,5-methanobenzo[g]-quinoline-3-carboxylate (described above in Example 6C), and the solution was stirred and refluxed for about eight hours, then neutralized by the addition of 8.6 ml. of glacial acetic acid, evaporated to dryness, and the residue dissolved in 200 ml. of water and 200 ml. of dilute hydrochloric acid. The aqueous solution was washed twice with ether, basified by the addition of about 30 ml. of concentrated ammonium hydroxide, and extracted twice with ether. The combined ether extracts, on washing with water, then with saturated sodium chloride, drying, filtering and evaporation to dryness, afforded 23.8 g. of a syrup which was dissolved in absolute ethanol, and treated with ethanolic hydrogen chloride. The solid which separated was removed by filtration, and the filtrate evaporated to dryness to give a residue which was dissolved in 200 ml. of water. The solution was washed once with ether, then basified by the addition of concentrated ammonium hydroxide, and extracted two times with diethyl ether. The ether extracts on washing, drying, filtering and evaporation to dryness afforded 19.0 g. of a solid which was dissolved in 100 ml. of ethyl acetate and treated with a solution of 12.1 g. of p-toluenesulfonic acid monohydrate in 200 ml. of ethyl acetate. There was thus obtained a solid which was recrystallized from ethanol/ether to give 7.0 g. of ethyl 4a$\alpha$,5$\alpha$-dimethyl-1,2,3,4,4a,5,10,10a-octahydro-2,5-methanobenzo[g]quinoline-3-carboxylate p-toluenesulfonate, m.p. 216°–220° C., isomeric at the 3-position with the starting material.

EXAMPLE 17

To a solution of 30 ml. of 2.0 M butyl lithium in hexane was added with cooling in an external ice bath a solution of 8.4 g. of cyclohexylisopropylamine (0.06 mole) in 45 ml. of pentane. When addition was complete, the solution was evaporated to dryness, and the resulting gum was dissolved in 60 ml. of tetrahydrofuran and the solution cooled to −70° C. with a dry ice-/acetone bath. The solution was then treated with a solution of 11.7 g. of ethyl 1-benzyl-4a$\alpha$,5$\alpha$-dimethyl-1,2,3,4,4a,5,10,10a-octahydro-2,5-methanobenzo[g]quinoline-3-carboxylate (described in Example 2N) in 120 ml. of tetrahydrofuran. When addition was complete the solution was stirred at −70° C. for about thirty minutes, allowed to warm to −20° C., and then treated with a solution of 12.8 g. (0.09 mole) of methyl iodide in 120 ml. of dimethylsulfoxide. The solution was stirred at ambient temperature for one hour and then poured into one liter of cold water and extracted three times with 200 ml. of ether. The ether extracts on washing with water and brine and evaporation to dryness afforded 17.5 g. of yellow oil which was chromatographed in 10% ether/hexane on a column of 2 kg. of silica. The product was eluted with 10% ether/hexane, the first 4.7 liters of eluate being discarded. The next two liters were combined and evaporated to dryness to give 3.13 g. of crude ethyl 1-benzyl-3,4a$\alpha$,5$\alpha$-trimethyl-1,2,3,4,4a,5,10 10a-octahydro-2,5-methanobenzo[g]quinoline-3-carboxylate.

The latter was dissolved in 200 ml. of absolute ethanol containing 0.7 ml. of concentrated hydrochloric acid, 0.5 g. of 10% palladium-on-charcoal was added, and the mixture was reduced under about 50 p.s.i. of hydrogen using the procedure described above in Example 6A. The product was converted to the methanesulfonate salt which was recrystallized from ethanol/ether to give 2.0 g. of ethyl 3,4a$\alpha$,5$\alpha$-trimethyl-1,2,3,4,4a,5,10,10a-octahydro-2,5-methanobenzo[g]-quinoline-3-carboxylate methanesulfonate, m.p. 225°–229° C.

Reaction of the above-described ethyl 1-benzyl-3,4a$\alpha$,5$\alpha$-trimethyl-1,2,3,4,4a,5,10,10a-octahydro-2,5-methanobenzo[g]quinoline-3-carboxylate with one mole of methyl lithium using the procedure described in Example 10A affords 1-benzyl-3-acetyl-3,4a$\alpha$,5$\alpha$-trimethyl-1,2,3,4,4a,5,10,10a-octahydro-2,5-methanobenzo[g]quinoline.

PREPARATION OF FINAL PRODUCTS

EXAMPLE 18

A. A solution of 11 g. (0.039 mole) of 1-methyl-3-acetyl-5$\alpha$-ethyl-1,2,3,4,4a,5,10,10a-octahydro-2,5-methanobenzo[g]quinoline hydrochloride (described in Example 10A) in 20 ml. of a solution prepared by adding 89 ml. of trimethylamine to 94 ml. of formic acid was stirred and heated under reflux for about 15 minutes. The mixture was allowed to cool, diluted with 100 ml. of water and washed with 50 ml. of diethyl ether. The aqueous layer was basified with 15 ml. of concentrated ammonium hydroxide and extracted twice with diethyl ether. The combined organic extracts, on washing once with water, drying and concentration to dryness, afforded 10 g. of a solid residue which was dissolved in about 30 ml. of absolute ethanol, the solution acidified with 13 ml. of ethereal hydrogen chloride, and diluted to 250 ml. with additional ether. The solid which separated was collected, washed, and set aside. (See Example 35A). The filtrate was washed with dilute ammonium hydroxide, dried, filtered and taken to dryness to give 3.1 g. of residue which was dissolved in diethyl ether and acidified with ethereal hydrogen chloride. The gummy, semi-crystalline material which separated was recrystallized from ethanol/ether to give 0.8 g. of 6(eq)-ethyl-1,2,3,4,5,6-hexahydro-3-methyl-11(eq)-(3-oxobutyl)-2,6-methano-3-benzazocine hydrochloride, m.p. 192°–196° C.

B. An alternative method for the preparation of the compounds of formula I from the compounds of formula II is illustrated by the following procedure:

A mixture of 10.0 g. (0.03 mole) of 1-methyl-3-acetyl-5α-ethyl-7-hydroxy-1,2,3,4,4a,5,10,10a-octahydro-2,5-methanobenzo[g]quinoline described in Example 10C in 675 ml. of mesitylene and 25 ml. of formic acid was stirred and refluxed for about eight hours while adding additional formic acid from time to time in order to maintain the pot temperature at 117°–119° C. The mixture was then cooled, extracted with dilute hydrochloric acid and the acid extracts washed first with diethyl ether, then basified with ammonium hydroxide and extracted once again with ethyl acetate. The organic extracts, on washing with brine, drying and evaporation to dryness, afforded 8.4 g. of solid which was recrystallized from ethyl acetate to give 3.7 g. of 6(eq)-ethyl-1,2,3-4,5,6-hexahydro-3-methyl-8-hydroxy-11(eq)-(3-oxobutyl)-2,6-methano-3-benzazocine, m.p. 190°–192° C.

Following a procedure similar to that described in Example 18A or B above, using an appropriate 7-$R_2$-1-$R_1$-3-$COR_5$-4aα-$R_3$-5α-$R_4$-1,2,3,4,4a,5,10,10a-octahydro-2,5-methanobenzo[g]quinoline of formula II, the following 8-$R_2$-6(eq)-$R_4$-1,2,3,4,5,6-hexahydro-3-$R_1$-11(ax)-$R_3$-11(eq)-(oxo-lower-alkyl)-2,6-methano-3-benzazocines of formula I in Table 18a are prepared, where $R_2'$, $R_2''$, $R_2'''$ and $R_8$ in each case are hydrogen. The particular procedure used, that of Example 18A or 18B, is indicated by the letter designation (A) or (B), respectively, below the Example number. Unless noted otherwise, products were isolated as, and melting points recorded for, the free base form.

TABLE 18a

| Example | $R_1$/$CH_2Z$ | $R_2$ | $R_3$/$R_4$ | Wt.II/Wt.I | m.p. (°C.)/Solv. |
|---|---|---|---|---|---|
| 18C | $CH_3$ | H | $CH_3$ | 10 (base) | 207–208 (a) |
| (A) | $CH_2CH_2COCH_3$ | | $C_2H_5$ | 2.1 (salt) | ethanol/ether |
| | | | | (a) | |
| 18D | $C_3H_5$—$CH_2$ (c) | H | H | 16 (base) | 206–208 (b) |
| (B) | $CH_2CH_2COCH_3$ | | $C_2H_5$ | 7.8 (base) | ethanol/ether |
| 18E | $C_6H_5CH_2$ | $CH_3O$ | H | 18.8 (base) | 104–106 |
| (B) | $CH_2CH_2COCH_3$ | | $CH_3$ | 7.2 (base) | ethanol |
| 18F | $C_6H_5CH_2$ | $CH_3O$ | H | 39 (base) | 122–125 |
| (B) | $CH_2CH_2COCH_3$ | | $C_2H_5$ | 10.6 (base) | ethanol |
| 18G | $C_6H_5CH_2$ | $CH_3O$ | $CH_3$ | 19.5 (base) | 132–135 |
| (B) | $CH_2CH_2COCH_3$ | | $CH_3$ | 11.5 (base) | ethanol |
| 18H | $CH_3$ | $CH_3O$ | H | 4.9 (base) | 132–134 |
| (B) | $CH_2CH_2COC_5H_{11}$ | | $CH_3$ | 3.3 (salt) | ethanol/ether |
| | | | | (d) | |
| 18J | $C_6H_5CH_2$ | H | $CH_3$ | 55.3 (base) | 229–232 |
| (B) | $CH_2CH_2COCH_3$ | | $CH_3$ | 37.7 (HCl) | ethanol/ether |
| 18K | $C_6H_5CH_2$ | $CH_3O$ | H | 18.7 (base) | 244–246 |
| (B) | $CH_2CH_2COC(CH_3)_3$ | | $CH_3$ | 15.3 (HCl) | ethanol/ether |
| 18L | $C_6H_5CH_2$ | $CH_3O$ | $CH_3$ | 39.2 (base) | 248–255 |
| (B) | $CH_2CH_2COC(CH_3)_3$ | | $CH_3$ | 33.0 (HCl) | ethanol/ether |
| 18M | $CH_3$ | $CH_3O$ | $CH_3$ | base | 217–221 |
| (B) | $CH_2CH_2COCH_2CH_3$ | | $CH_3$ | salt (e) | ethanol/ether |
| 18N | $CH_3$ | $CH_3O$ | $CH_3$ | base | 176–179 |
| (B) | $CH_2CH_2CO(CH_2)_2CH_3$ | | $CH_3$ | salt (e) | acetone/ether |
| 18P | $C_3H_5$—$CH_2$ (c) | $CH_3O$ | $CH_3$ | base | 219–220 |
| (B) | $CH_2CH_2CO(CH_2)_3CH_3$ | | $CH_3$ | HCl | acetone |
| 18Q | $CH_3$ | $CH_3O$ | H | base | 183.5–185 |
| (B) | $CH_2CH_2CO(CH_2)_3CH_3$ | | $CH_3$ | salt (f) | acetone |
| 18R | $C_6H_5CH_2$ | $CH_3O$ | $CH_3$ | base | 226–228 |
| (B) | $CH_2CH_2CO(CH_2)_3CH_3$ | | $CH_3$ | HCl | acetone |
| 18S | $CH_3$ | $CH_3O$ | $CH_3$ | base | 146–148 |
| | $CH_2CH_2COCH_2CH(CH_3)_2$ | | $CH_3$ | salt (e) | acetone/ether |
| 18T | $C_6H_5CH_2$ | H | $CH_3$ | base | 190–193 |
| | $CH_2CH_2CO(CH_2)_4CH_3$ | | $CH_3$ | HCl | acetone/ether |
| 18U | $C_6H_5CH_2$ | $CH_3O$ | $CH_3$ | base | 226–227 |
| | $CH_2CH_2CO(CH_2)_4CH_3$ | | $CH_3$ | HCl | acetone/ether |
| 18V | $CH_3$ | $CH_3O$ | $CH_3$ | base | 229–231 |
| | $CH_2CH_2CO(CH_2)_2CH(CH_3)_2$ | | $CH_3$ | HCl | acetone |
| 18W | $CH_3$ | $CH_3O$ | $CH_3$ | base | 178–181 (g) |
| | $CH_2CH_2CO(CH_2)_5CH_3$ | | $CH_3$ | HCl | acetone/ether |
| 18X | $CH_3$ | $CH_3O$ | H | base | oil |
| | $CH_2CH_2CO(CH_2)_2CH(CH_3)_2$ | | $CH_3$ | base | |
| 18Y | $CH_3$ | $CH_3O$ | $CH_3$ | base | 209–212 |
| | $CH_2CH_2CO(CH_2)_3CH_3$ | | $CH_3$ | HCl | ethanol/ether |
| 18Z | $CH_3$ | $CH_3O$ | $CH_3$ | base | 137–141 |

TABLE 18a-continued

| Example | R₁/CH₂Z | R₂ | R₃/R₄ | Wt.II/Wt.I | m.p. (°C.)/Solv. |
|---|---|---|---|---|---|
| | $CH_2CH_2CO(CH_2)_2C_6H_5$ | | $CH_3$ | $HBr \cdot H_2O$ | $H_2O$ |

(a) p-Toluenesulfonate hemihydrate
(b) Hydrochloride
(c) Cyclopropylmethyl
(d) p-Toluenesulfonate
(e) Methanesulfonate
(f) Picrate
(g) The p-toluenesulfonate has m.p. 188–190° C. (from acetone)

Following a procedure similar to that described in Example 18A or 18B above, using an appropriate 7-R₂-1-R₁-3-lower-alkanoyl-4aα-R₃-5α-R₄-1,2,3,4,4a,5,10,-10a-octahydro-2,5-methanobenzo[g]quinoline of formula II, there are obtained the following 8-R₂-6(eq)-R₄-1,2,3,4,5,6-hexahydro-3-R₁-11(ax)-R₃-11(eq-)—(CH₂CH₂COR₅)—2,6-methano-3-benzazocines of formula I in Table 18b, where in each case R₂′, R₂″R₂‴ and R₈ are each hydrogen.

TABLE 18b

| Example | R₁/CH₂Z | R₂ | R₃/R₄ |
|---|---|---|---|
| 18AA | $CH_3$ | $CH_3O$ | $CH_3$ |
| | $CH_2CH_2COCH_3$ | | $CH_3$ |
| 18AB | $CH_3$ | H | $CH_3$ |
| | $CH_2CH_2CO(CH_2)_4CH_3$ | | $CH_3$ |
| 18AC | $CH_3$ | H | $CH_3$ |
| | $CH_2CH_2CO(CH_2)_2CH(CH_3)_2$ | | $CH_3$ |
| 18AD | $CH_3$ | $CH_3O$ | H |
| | $CH_2CH_2CO(CH_2)_2CH(CH_3)_2$ | | $CH_3$ |
| 18AE | $CH_3$ | $CH_3O$ | |
| | $CH_2CH_2CO(CH_2)_2CH(CH_3)_2$ | | $\|$ $(CH_2)_4$ $\|$ |
| 18AF | $CH_3$ | $CH_3O$ | $CH_3$ |
| | $CH_2CH_2CO(CH_2)_3CH(CH_3)_2$ | | $CH_3$ |
| 18AG | $CH_3$ | $CH_3O$ | $CH_3$ |
| | $CH_2CH_2CO(CH_2)_2C_3H_5$ (a) | | $CH_3$ |
| 18AH | $CH_3$ | $CH_3O$ | $CH_3$ |
| | $CH_2CH_2COCH_2C_4H_7$ (b) | | $CH_3$ |
| 18AJ | $CH_3$ | $CH_3O$ | $CH_3$ |
| | $CH_2CH_2CO(CH_2)_2C_5H_9$ (c) | | $CH_3$ |
| 18AK | $CH_3$ | H | $CH_3$ |
| | $CH_2CH_2CO(CH_2)_2C_5H_9$ (c) | | $CH_3$ |

TABLE 18b-continued

| Example | R₁/CH₂Z | R₂ | R₃/R₄ |
|---|---|---|---|
| 18AL | $CH_3$ | $CH_3O$ | $CH_3$ |
| | $CH_2CH_2COCH_2C_6H_5$ | | $CH_3$ |
| 18AM | $CH_3$ | H | $CH_3$ |
| | $CH_2CH_2COC_6H_5$ | | $CH_3$ |
| 18AN | $CH_3$ | $CH_3O$ | $CH_3$ |
| | $CH_2CH_2COC_6H_5$ | | $CH_3$ |
| 18AP | $CH_3$ | $CH_3O$ | $CH_3$ |
| | $CH_2CH_2COC_6H_4CH_3^{(3)}$ | | $CH_3$ |
| 18AQ | $CH_3$ | $CH_3O$ | $CH_3$ |
| | $CH_2CH_2COC_6H_4CH_3^{(4)}$ | | $CH_3$ |
| 18AR | $CH_3$ | $CH_3O$ | $CH_3$ |
| | $CH_2CH_2CO(CH_2)_4CH_3$ | | $C_2H_5$ |
| 18AS | $C_6H_5CH_2$ | $CH_3O$ | $CH_3$ |
| | $CH_2CH_2CO(CH_2)_2CH(CH_3)_2$ | | $CH_3$ |
| 18AT | $CH_3$ | $CH_3O$ | $CH_3$ |
| | $CH_2CH_2CO(CH_2)_2CH(CH_3)_2$ | | $C_2H_5$ |
| 18AU | $CH_3$ | $CH_3O$ | $CH_3$ |
| | $CH_2CH_2CO(CH_2)_3CH(CH_3)_2$ | | $CH_3$ |
| 18AV | $CH_3$ | $CH_3O$ | $CH_3$ |
| | $CH_2CH_2COCH_2CH_2C_4H_7$ | | $CH_3$ |

(a) Cyclopropyl
(b) Cyclobutyl
(c) Cyclopentyl

Following a procedure similar to that described above in Example 18A or 18B, using an appropriate 7-R₂-8-R₂′-1-R₁-3-lower-alkanoyl-4aα-R₃-5α-R₄-1,2,3,4,4a,5,10,10a-octahydro-2,5-methanobenzo[g-]quinoline of formula II, it is contemplated that the following 8-R₂′-6(eq)-R₄-1,2,3,4,5,6-hexahydro-3R₁-11(ax)-R₃-11(eq)—(CH₂CH₂COR₅)—2,6-methano-3-benzazocines of formula I in Table 18c can be prepared, where in each case R₂″, R₂‴ and R₈ are hydrogen.

TABLE 18c

| Example | R₁/CH₂Z | R₂/R₂′ | R₃/R₄ |
|---|---|---|---|
| 18AW | $C_6H_5CH_2$ | H | H |
| | $CH_2CH_2COCH_3$ | H | $C_2H_5$ |
| 18AX | $CH_3$ | H | $CH_3$ |
| | $CH_2CH_2COCH_3$ | H | $CH_3$ |
| 18AY | $C_6H_5CH_2$ | H | H |
| | $CH_2CH_2COCH_3$ | H | $CH_3$ |
| 18AZ | $C_6H_5CH_2$ | HO | H |
| | $CH_2CH_2COCH_3$ | H | $CH_3$ |
| 18BA | $CH_3$ | H | H |
| | $CH_2CH_2COC_3H_7$ | H | $C_2H_5$ |
| 18BB | $C_6H_{11}$ | $CH_3S$ | H |
| | $CH_2CH_2COCH_3$ | H | $CH_3$ |
| 18BC | $4\text{-}BrC_6H_4CH_2CH_2$ | $CH_3O$ | H |
| | $CH_2CH_2COCH_3$ | H | $CH_3$ |
| 18BD | $4\text{-}ClC_6H_4CH_2CH_2$ | $CH_3CONH$ | H |
| | $CH_2CH_2COCH_3$ | H | $CH_3$ |
| 18BE | $4\text{-}FC_6H_4CH_2CH_2$ | $C_2H_5OCONH$ | H |
| | $CH_2CH_2COCH_3$ | H | $CH_3$ |
| 18BF | $4\text{-}Cl\text{-}3\text{-}CH_3C_6H_3CH_2CH_2$ | H | H |
| | $CH_2CH_2COCH_3$ | H | $CH_3$ |
| 18BG | $3\text{-}CH_3COOC_6H_4CH_2CH_2$ | H | H |
| | $CH_2CH_2COCH_3$ | H | $CH_3$ |
| 18BH | $3,4\text{-}(CH_3O)_2C_6H_3CH_2CH_2$ | H | H |
| | $CH_2CH_2COCH_3$ | H | $CH_3$ |
| 18BJ | $4\text{-}CH_3SC_6H_4CH_2CH_2$ | H | H |
| | $CH_2CH_2COCH_3$ | H | $CH_3$ |
| 18BK | $3\text{-}CF_3C_6H_4CH_2CH_2$ | H | H |
| | $CH_2CH_2COCH_3$ | H | $CH_3$ |
| 18BL | $3\text{-}CH_3CONHC_6H_4CH_2CH_2$ | H | H |

TABLE 18c-continued

| Example | R₁/CH₂Z | R₂/R₂' | R₃/R₄ |
|---|---|---|---|
| | CH₂CH₂COCH₃ | H | CH₃ |
| 18BM | | H | H |
| | 3,4-OCH₂OC₆H₃CH₂CH₂ | | |
| | CH₂CH₂COCH₃ | H | CH₃ |
| 18BN | CH₃ | H | H |
| | CH₂CH₂COCH₃ | Cl | CH₃ |
| 18BP | CH₃ | H | H |
| | CH₂CH₂COCH₃ | Br | CH₃ |
| 18BQ | CH₃ | H | H |
| | CH₂CH₂COCH₃ | F | CH₃ |
| 18BR | CH₃ | H | H |
| | CH₂CH₂COCH₃ | CF₃ | CH₃ |
| 18BS | CH₃ | H | H |
| | CH₂CH₂COCH₃ | CH₃ | CH₃ |
| 18BT | CH₃ | C₆H₅ | H |
| | CH₂CH₂COCH₃ | H | CH₃ |
| 18 BU | CH₃ | | H |
| | CH₂CH₂COCH₃ | CH₂(O-O) | CH₃ |
| 18BV | CH₃ | H | H |
| | CH₂CH₂COCH₃ | H | H |
| 18BW | CH₃ | H | H |
| | CH₂CH₂COCH₃ | H | CH₂CH₂Cl |
| 18BX | CH₃ | H | |
| | CH₂CH₂(COCH₃ | | (CH₂)₃ |
| 18BY | CH₃ | H | |
| | CH₂CH₂COCH₃ | H | (CH₂)₄ |
| 18BZ | CH₃ | H | H |
| | CH₂CH₂COCH₃ | H | CH₂CH₂OCH₃ |
| 18CA | CH₃ | H | H |
| | CH₂CH₂COC₆H₅ | H | C₂H₅ |
| 18CB | CH₃ | H | H |
| | CH₂CH₂COCH₃ | H | CH₂CH₂SC₆H₅ |
| 18CC | CH₃ | H | H |
| | CH₂CH₂COCH₃ | H | CH₂CH₂SOC₆H₅ |
| 18CD | CH₃ | H | H |
| | CH₂CH₂COCH₃ | H | CH=CH₂ |
| 18CE | CH₃ | H | H |
| | CH₂CH₂COCH₃ | H | CH₂CH₂SCH₃ |
| 18CF | CH₃ | H | H |
| | CH₂CH₂COCH₃ | H | CH₂CH₂OH |
| 18CG | CH₃ | CH₃O | CH₃ |
| | COCH₂-cyclopropyl | H | CH₃ |
| 18CH | CH₃ | CH₃O | CH₃ |
| | COCH₂-cyclopentyl | H | CH₃ |
| 18CJ | CH₃ | CH₃O | CH₃ |
| | COCH₂-cyclohexyl | H | CH₃ |
| 18CK | CH₃ | CH₃O | CH₃ |
| | CO(CH₂)₂-1-cyclohexyl | H | CH₃ |

Example 18CL

Heating the 1,5α,8-trimethyl-3-acetyl-1,2,3,4,4a,5,10,10a-octahydro-2,5-methanobenzo[g]quinoline described in Example 2AR with formic acid in mesitylene using the procedure described above in Example 18B affords 3,6(eq),9-tri-methyl-1,2,3,4,5,6-hexahydro-11(eq)-(3-oxobutyl)-2,6-methano-3-benzazocine.

Example 18 CM

Heating the 1-benzyl-3-acetyl-3,4aα,5α-trimethyl-1,2,3,4,4a,5,10,10a-octahydro-2,5-methanobenzo[g]quinoline described in Example 17 with formic acid in mesitylene using the procedure described above in Example 18B affords 3-benzyl-11(ax),6(eq)-dimethyl-1,2,3,4,5,6-hexahydro-11(eq)-(2-methyl-3-oxobutyl)-2,6-methano-3-benzazocine.

Example 18 CN

Heating the 1-acetyl-3-pentanoyl-1,2,3,4,4a,5,10,10a-octahydro-2,5-methanobenzo[g]quinoline described above in Example 10AK with formic acid in mesitylene using the procedure described above in Example 18B affords 3-acetyl-1,2,3,4,5,6-hexahydro-11(eq)-(3-oxoheptyl)-2,6-methano-3-benzazocine.

Example 19

A. A solution of 27.0 g. (0.072 mole) of 3-benzyl-8-methoxy-6(eq)-methyl-1,2,3,4,5,6-hexahydro-11(eq)-(3-oxobutyl)-2,6-methano-3-benzazocine (described in Example 18E) was dissolved in 250 ml. of 48% hydrobromic acid and the mixture heated under reflux for about eleven hours. The mixture was concentrated to a small volume in vacuo, diluted with 100 ml. of water, concentrated again, and finally boiled with about 50 ml.

of isopropanol. The solid which separated was collected and dried to give 23 g. of 3-benzyl-8-hydroxy-6(eq)-methyl-1,2,3,4,5,6-hexahydro-11(eq)-(3-oxobutyl)-2,6-methano-3-benzazocine hydrobromide, m.p. 156°–165° C.

Following a procedure similar to that described in Example 19A above using an appropriate 8-methoxy-3-methyl-11(ax)-R$_3$-6(eq)-methyl-1,2,3,4,5,6-hexahydro-11(eq)—CH$_2$CH$_2$COR$_5$—2,6-methano-3-benzazocine of formula I, the following 8-hydroxy-3-R$_1$-11(ax)-R$_3$-6(eq)-R$_4$-1,2,3,4,5,6-hexahydro-11(eq)—CH$_2$CH$_2$COR$_5$—2,6-methano-3-benzazocines of formula I in Table 19a were prepared where, unless noted otherwise, in each case R$_2$ is hydroxy, R$_2'$, R$_2''$, R$_2'''$ and R$_8$ are each hydrogen, and R$_1$, R$_3$ and R$_4$ are each methyl. The form (base or salt) of the starting material and product is given in parentheses along with the respective weights.

TABLE 19a

| Example | R$_5$ | Wt.S.M./ Wt. Prod. | m.p.(°C.)/Solv. |
| --- | --- | --- | --- |
| 19B | C$_5$H$_{11}$ (b) | 4.0 (salt) (a) 1.8 (base) | 107–109 ethanol |
| 19C | C$_2$H$_5$ | 3.5 (base) 2.5 (HCl) | 265–268 ethanol/ether |
| 19D | C$_3$H$_7$ | 5.0 (base) 3.7 (HCl) | 264–266 ethanol |
| 19E | C$_4$H$_9$ (b) | 5.1 (base) 1.9 (base) | 120–122 ethyl acetate |
| 19F | (CH$_2$)$_2$CH(CH$_3$)$_2$ | 4.0 (HCl) 3.3 (HCl) | 260–263 (d) isopropanol |
| 19G | C$_6$H$_{13}$ | 4.5 (HCl) 2.8 (HCl) | 206–209 isopropanol |
| 19H | C$_5$H$_{11}$ | 4.5 (HCl) 1.7 (HCl) | 252–255 (e) isopropanol |
| 19J | CH$_2$CH(CH$_3$)$_2$ | 5.5 (base) 2.6 (HCl) | 251–254 ethanol |
| 19K | (CH$_2$)$_2$CH(CH$_3$)$_2$ (b) | 7.0 (base) 1.6 (base) | 101–103.5 ethyl acetate/hexane |
| 19L | (CH$_2$)$_2$C$_6$H$_5$ | 8.1 (salt) (a) 1.6 (CH$_3$SO$_3$H) | 233–235 ethanol |
| 19M | CH$_3$ | 5.8 (base) 1.3 (base) | 170–173 (f) ethanol |
| 19N | (CH$_2$)$_4$CH$_3$ (g) | 3.3 (base) 1.4 (base) | 140–143 ethanol |
| 19P | (CH$_2$)$_4$CH$_3$ (h) | 9.7 (base) 4.4 (base) | 138.5–141.5 ethanol |
| 19Q | (CH$_2$)$_4$CH$_3$ (i) | 9.2 (base) 8.6 (HCl) | 253–257 acetone/ether |
| 19R | (CH$_2$)$_3$CH(CH$_3$)$_2$ | 6.5 (base) 4.2 (base) | 116.5–118.5 ethyl acetate/hexane |
| 19S | (CH$_2$)$_2$CH(CH$_3$)$_2$ (g) | 5.4 (base) 2.2 (HCl) | 264.5–267 ethanol |
| 19T | (CH$_2$)$_2$CH(CH$_3$)$_2$ (i) | 21.7 (base) 24.0 (HCl) | 160.5–163.5 ethanol/ether |
| 19U | (CH$_2$)$_2$CH(CH$_3$)$_2$ (j) | 4.0 (HCl) 3.0 (HCl) | 270–273 ethanol/ether |
| 19V | (CH$_2$)$_2$cyclopentyl | 12.7 (base) 4.8 (H$_2$SO$_4$) | 230–235 (h) ethanol/ether |
| 19W | C$_6$H$_5$ | 5.8 (base) 1.9 (base) | 182–184.5 ethyl acetate/hexane |
| 19X | 3-CH$_3$C$_6$H$_4$ | 6.5 (base) 1.9 (base) | 203–206 methanol |
| 19Y | 4-CH$_3$C$_6$H$_4$ | 3.0 (base) 1.8 (CH$_3$SO$_3$H) | 273–276 methanol |
| 19Z | CH$_2$C$_6$H$_5$ | 4.2 (base) 3.1 (CH$_3$SO$_3$H) | 228–231 methanol |
| 19AA | CH$_2$C$_6$H$_4$CH$_3$ (3) | 5 (base) | 232–234 |

TABLE 19a-continued

| Example | R$_5$ | Wt.S.M./ Wt. Prod. | m.p.(°C.)/Solv. |
| --- | --- | --- | --- |
| | | 3.0 (CH$_3$SO$_3$H) | methanol |

(a) p-Toluenesulfonate
(b) R$_3$ is hydrogen
(c) A sample of the racemic base was resolved with l- and d-mandelic acid to give, respectively, the l-mandelate, m.p. 190-193° C. (from acetone), $[\alpha]_D^{25} = -6.9°$, and the d-mandelate, m.p. 191-193° C. (from acetone), $[\alpha]_D^{25} = +5.5°$. Cleavage of the two mandelate salts to the respective free bases and conversion of the latter to the hydrochlorides gave, respectively, the l- and d-hydrochlorides, m.p. 240-242° C. (from ethanol/ether), $[\alpha]_D^{25} = -32.2°$ and m.p. 240-242° C. (from ethanol/ether), $[\alpha]_D^{25} = +32.1°$.
(d) The methanesulfonate has m.p. 189-191° C. (from acetone/diethyl ether).
(e) The methanesulfonate has m.p. 178-179° C. (from acetone); the free base has m.p. 131-133° C. (from methanol); and the 2-naphthalenesulfonate has m.p. 195-198° C. (from methanol/diethyl ether). A sample of the racemic base was resolved with l- and d- mandelic acid to give, respectively, the l- mandelate; m.p. 196-198° C. (from acetone), $[\alpha]_D^{25} = -5.2°$, and the d- mandelate, m.p. 195-197° C. (from acetone), $[\alpha]_D^{25} = 5.3°$. Cleavage of the two mandelate salts to the respective free bases and conversion of the latter to the methanesulfonates gave, respectively, the l- and d-methanesulfonates, m.p. 212-214° C. (from methanol/diethyl ether), $[\alpha]_D^{25} = -25.7°$ and m.p. 212-214° C. (from methanol/diethyl ether), $[\alpha]_D^{25} = +26.7°$.
(f) The methanesulfonate has m.p. 265-268° C. (from ethanol/ether)
(g) R$_4$ is C$_2$H$_5$
(h) R$_1$ is hydrogen
(i) R$_1$ is benzyl
(j) R$_3$/R$_4$ are —(CH$_2$)$_4$—
(k) A sample of the racemic base was resolved with d- and l- mandelic acid to give, respectively, the d-mandelate, m.p. 200-202° C. (from acetone) and the l-mandelate, m.p. 198-201° C. (from acetone). Cleavage of the mandelate salts to the respective free bases and conversion of the latter to the methanesulfonates gave, respectively, the l- and d- methanesulfonates, m.p. 247-249° C. (from methanol/ether), $[\alpha]_D^{25} = -24.4°$ and m.p. 246-248° C. (from methanol/ether), $[\alpha]_D^{25} = +25.8°$.

Following a procedure similar to that described in Example 19A above, using an appropriate 8-methoxy-3,6(eq),11(ax)-trimethyl-1,2,3,4,5,6-hexahydro-11(eq)-CH$_2$CH$_2$COR$_5$-2,6-methano-3-benzazocine of formula I, the following 8-hydroxy-3,6(eq),11(ax)-trimethyl-1,2,3,4,5,6-hexahydro-11(eq)-CH$_2$CH$_2$COR$_5$-2,6-methano-3-benzazocines are prepared where, in each case R$_2$ is hydroxy, R$_2'$, R$_2''$, R$_2'''$ and R$_8$ are each hydrogen, and R$_1$, R$_3$ and R$_4$ are each methyl.

TABLE 19b

| Example | R$_5$ |
| --- | --- |
| 19AB | CH$_2$-cyclopropyl |
| 19AC | CH$_2$-cyclobutyl |
| 19AD | CH$_2$CH$_2$-cyclobutyl |
| 19AE | CH$_2$-cyclopentyl |
| 19AF | CH$_2$-cyclohexyl |
| 19AG | CH$_2$CH$_2$-cyclohexyl |

Example 20

A. A solution of 23.1 g. (0.05 mole) of 3-benzyl-8-hydroxy-6-(eq)-methyl-1,2,3,4,5,6-hexahydro-11(eq)-(3-oxobutyl)-2,6-methano-3-benzazocine hydrobromide (described in Example 19A) in 150 ml. of DMF was reduced with hydrogen over 10 g. of 10% palladium-on-charcoal using the procedure described above in Example 3. The product obtained was recrystallized from ethanol to give 16.1 g. of 8-hydroxy-6(eq)-methyl-1,2,3,4,5,6-hexahydro-11(eq)-(3-oxobutyl)-2,6-methano-3-benzazocine hydrobromide, m.p. 235°–237° C. (from ethanol).

Following a procedure similar to that described in Example 20A above using an appropriate 8-R$_2$-3-benzyl-11(ax)-R$_3$-6(eq)-R$_4$-1,2,3,4,5,6-hexahydro-11(eq)—CH$_2$Z—2,6-methano-3-benzazocine of formula I, the following 8-R$_2$-11(ax)-R$_3$-6(eq)-R$_4$-1,2,3,4,5,6-hexahydro-11(eq)-CH$_2$Z-2,6-methano-3-benzazocines of formula I in Table 20 were prepared where in each case R$_1$, R$_2'$, R$_2''$, R$_2'''$ and R$_8$ are hydrogen. Compounds for which no value for R$_6$ is given are the ketones (Z is $CH_2COR_5$). Otherwise the compounds are the carbinols [Z is $CH_2C(R_5)(R_6)OH$]. The form (base or salt) of the starting material and product is given in parentheses along with the respective weights.

TABLE 20

| Example | $R_2$ | $R_5/R_6$ | $R_3/R_4$ | Wt. S.M./Wt. Prod. | m.p. (°C.)/Solv. |
|---|---|---|---|---|---|
| 20B | $CH_3O$ | $CH_3$ | H | 21.2 (base) | 189–193 |
| | | — | $CH_3$ | 11.4 (HCl) | ethanol |
| 20C | $CH_3O$ | $C_5H_{11}$ | $CH_3$ | 13.8 (HCl) | 179–182 |
| | | — | $CH_3$ | 5.8 (HCl) | methanol/ether |
| 20D | H | $C_5H_{11}$ | $CH_3$ | 4.2 (HCl) | 155–157 |
| | | — | $CH_3$ | 2.2 (HCl) | acetone/ether |
| 20E | $CH_3O$ | $CH_3$ | $CH_3$ | 11.8 (HCl) | 130.0–132.5 |
| | | $CH_3$ | $CH_3$ | 6.5 (base) | — |
| 20F | $CH_3O$ | $C_4H_9$ | $CH_3$ | 9.0 (HCl) | 170–172 |
| | | — | $CH_3$ | 6.3 (HCl) | acetone |
| 20G | HO | $(CH_2)_4CH_3$ | $CH_3$ | 4.7 (HCl) | 209–211 |
| | | — | $CH_3$ | 2.6 (HCl) (a) | ethanol |
| 20H | HO | $(CH_2)_2CH(CH_3)_2$ | | | |
| | | | $CH_3$ | 24.0 (HCl) | 160.5–163.5 |
| | | — | $CH_3$ | 4.6 (base) | ethyl acetate |

(a) The free base has m.p. 138–141° C. (from ethyl acetate)

Example 21

A. A mixture of 11.4 g. (0.03 mole) of 8-hydroxy-6(eq)-methyl-1,2,3,4,5,6-hexahydro-11(eq)-(3-oxobutyl)-2,6-methano-3-benzazocine hydrobromide (described in Example 20A), 5.4 g. of sodium bicarbonate and 5.2 g. (0.04 mole of cyclopropylmethyl bromide in 150 ml. of DMF was heated under reflux for about nine hours and then concentrated to a small volume in vacuo. The residue was partitioned between ammonium hydroxide and ethyl acetate, the organic layer separated, and the aqueous layer extracted with additional portions of ethyl acetate. The combined extracts were washed once with water, then with brine, dried, filtered and taken to dryness to give 12.1 g. of crude product which was converted to the hydrochloride salt. The latter was recrystallized once from acetonitrile and once from ethanol/ether to give 5.2 g. of 3-cyclopropylmethyl-8-hydroxy-6(eq)-methyl-1,2,3,4,5,6-hexahydro-11(eq)-(3-oxobutyl)-2,6-methano-3-benzazocine hydrochloride, m.p. 147°–154° C.

B. Following a procedure similar to that described in Example 21A, 3-cyclopropylmethyl-8-methoxy-6(eq)-methyl-1,2,3,4,5,6-hexahydro-11(eq)-(3-oxobutyl)-2,6-methano-3-benzazocine (12.9 g.) was prepared by reaction of 15.0 g. (0.04 mole) of 8-methoxy-6(eq)-methyl-1,2,3,4,5,6-hexahydro-11-(eq)-(3-oxobutyl)-2,6-methano-3-benzazocine (described in Example 20B) with cyclopropylmethyl bromide in the presence of sodium bicarbonate in DMF.

C. 3,6(eq)-Dimethyl-8-hydroxy-1,2,3,4,5,6-hexahydro-11(eq)-(3-oxobutyl)-2,6-methano-3-banzazocine p-toluenesulfonate (9.9 g.) m.p. 199°–201° C. (from ethanol), was prepared by reductive alkylation of 11.4 g. of 8-hydroxy-6(eq)-methyl-1,2,3,4,5,6-hexahydro-11(eq)-(3-oxobutyl)-2,6-methano-3-benzazocine hydrobromide (described in Example 20A) with formaldehyde and triethylamine over palladium-on-charcoal in ethanol under about 50 p.s.i. of hydrogen using the procedure described in Example 42.

D. 3,6(eq)-Dimethyl-8-methoxy-1,2,3,4,5,6-hexahydro-11(eq)-(3-oxobutyl)-2,6-methano-3-benzazocine (7.5 g.) was prepared by reductive alkylation of 8.2 g. of 8-methoxy-6(eq)-methyl-1,2,3,4,5,6-hexahydro-11(eq)-(3-oxobutyl)-2,6-methano-3-benzazocine hydrochloride (described in Example 20B) with formaldehyde and triethylamine over palladium-on-charcoal in ethanol under about 50 p.s.i. of hydrogen using the procedure described in Example 42. The hydrochloride salt gives m.p. 181°–183° C. (from ethanol).

E. 3,6(eq),11(ax)-Trimethyl-8-methoxy-1,2,3,4,5,6-hexahydro-11(eq)-(3-oxooctyl)-2,6-methano-3-benzazocine hydrochloride (5.5 g.), m.p. 212°–214° C. (from acetone) was prepared by reductive alkylation of 7.2 g. of 6(eq),11(ax)-dimethyl-8-methoxy-1,2,3,4,5,6-hexahydro-11(eq)-(3-oxooctyl)-2,6-methano-3-benzazocine with 2.0 cc. of 37% aqueous formaldehyde and 3.8 cc. of 97% formic acid. The p-toluenesulfonate gives m.p. 200°–201° C. (from ethanol/diethyl ether).

F. 3-Cyclobutylmethyl-6(eq),11(ax)-dimethyl-8-methoxy-1,2,3,4,5,6-hexahydro-11(eq)-(3-oxooctyl)-2,6-methano-3-benzazocine hydrochloride (2.1 g.), m.p. 207°–209° C. (from acetone) was prepared by reaction of 0.15 mole (from 5.9 g. of the hydrochloride) of 6(eq),11(ax)-dimethyl-8-methoxy-1,2,3,4,5,6-hexahydro-11(eq)-(3-oxooctyl)-2,6-methano-3-benzazocine with 2.5 g. of cyclobutylmethyl bromide in 60 ml. of DMF in the presence of 1.5 g. of sodium bicarbonate.

G. 3,6(eg),11(ax)-Trimethyl-8-methoxy-1,2,3,4,5,6-hexahydro-11(eg)-(3-oxoheptyl)-2,6-methano-3-benzazocine hydrochloride (3.2 g.), m.p. 209°–211° C. (from acetone/ether) was prepared by the reductive alkylation of 5.3 g. of 6(eg),11(ax)-dimethyl-8-methoxy-1,2,3,4,5,6-hexahydro-11(eg)-(3-oxoheptyl-2,6-methano-3-benzazocine with 1.5 ml. of 37% aqueous formaldehyde in 100 ml. of ethanol over 1.0 g. of palladiumon charcoal under a hydrogen pressure of about 45 p.s.i.

H. 3-Ethyl-6(eg),11(ax)-dimethyl-1,2,3,4,5,6-hexahydro-11(eg)-(3-oxooctyl-2,6-methano-3-benazazocine was prepared by reaction of 0.02 mole of 6(eq),11(ax)-dimethyl-1,2,3,4,5,6-hexahydro-11(eq)-(3-oxooctyl)-2,6-methano-3-benzazocine with 5 ml. of acetic anhydride in 50 ml. of dry pyridine. The resulting 3-acetyl-6(eg),1-1(ax)-dimethyl-1,2,3,4,5,6-hexahydro-11(eq)-(3-oxooctyl)-2,6-methano-3-benzazocine (3.4 g., m.p. 56°–59° C.) was dissolved in 100 ml. of toluene with 11 ml. of ethylene glycol and 0.5 g. of p-toluenesulfonic acid and the mixture distilled until no further water was produced. The corresponding ethylene glycol ketal (4.0 g.) was isolated as an oil from the toluene solution after washing the latter with aqueous bicarbonate. Reduction of the ketal with 1.2 g. of lithium aluminum hydride in 150 ml. of tetrahydrofuran using the procedure described above in Example 12A afforded 1.7 g. of the final product in the form of the ethylene glycol ketal hydrochloride, m.p. 198°–201° C. (from ethyl acetate). Hydrolysis of the latter in dilute hydrochloric acid gives the free ketone.

J. 3-Cyclopropylmethyl-6(eq),11(ax)-dimethyl-8-hydroxy-1,2,3,4,5,6-hexahydro-11(eq)-(3-oxooctyl)-2,6-methano-3-benzazocine methanesulfonate (2.4 g.), m.p. 211°–213° C. (from methanol) was prepared by reaction of 3.8 g. (0.01 mole) of 6(eg),11(ax)-dimethyl-8-hydroxy-1,2,3,4,5,6-hexahydro-11(eg)-(3-oxooctyl)-2,6-methano-3-benzazocine with 1.7 g. (0.013 mole) of cyclopropylmethyl bromide in 25 ml. of DMF in the presence of 2.1 g. of sodium bicarbonate.

K. 3-Ethyl-6(eg),11(ax)-dimethyl-8-hydroxy-1,2,3,4,5,6-hexahydro-11(eq)-(3-oxo-6-methylheptyl)-2,6-methano-3-benzazocine (1.6 g.) m.p. 116°–118.5° L C. (from ethyl acetate/hexane) was prepared by reaction of 6.0 g. (0.018 mole) of 6(eq), 11(ax)-dimethyl-8-hydroxy-1,2,3,4,5,6-hexahydro-11(eq)-(3-oxo-6-methylheptyl-2,6-methano-3-benzazocine with 2.11 ml. (0.026 mole) of ethyl iodide in 45 ml. of DMF in the presence of 2.2 g. of sodium bicarbonate.

L. 3-Cyclopropylmethyl-6(eq),11(ax)-dimethyl-8-hydroxy-1,2,3,4,5,6-hexahydro-11(eq)-(3-oxo-6-methylheptyl-2,6-methanesulfonate (2.2g.), m.p. 190.5–193.0 (from ethanol/ether) was prepared by reaction of 4.2 g. (0.012 mole) of 6(eq),11l (ax)-dimethyl-8-hydroxy-1,2,3,4,5,6-hexahydro-11-(eq)-(3-oxo-6-methylheptyl)-2,6-methano-3-benzazocine with 1.8 g. (0.013 mole of cyclopropylmethyl bromide in 30 ml. of DMF in the presence of 1.1 g. of sodium bicarbonate.

M. 3-Ethyl-6(eq),11(ax)-dimethyl-8-hydroxy-1,2,3,4,5,6-hexahydro-11(eq)-(3-oxooctyl)-2,6-methano-3-benzazocine (3.8 g.), m.p. 140.5°–144° C. (from ethanol) was prepared by reaction of 6.2 g. (0.018 mole) of 6(eq),11(ax)-dimethyl-8-hydroxy-1,2,3,4,5,6-hexahydro-11(eq)-(3-oxooctyl)-2,6-methano-3-benzazocine with 2.2 ml. (0.027 mole) of ethyl iodide in 45 ml. of DMF in the presence of 2.3 g. of sodium bicarbonate.

N. 3-Propyl-6(eq),11(ax)-dimethyl-8-hydroxy-1,2,3,4,5,6-hexahydro-11(eq)-(3-oxooctyl)-2,6-methano-3-benzazocine methanesulfonate (2.1 g.), m.p. 154°–157° C. (from ethanol) was prepared by reaction of 3.6 g. (0.011 mole) of 6(eq),11(ax)-dimethyl-8-hydroxy-1,2,3,4,5,6-hexahydro-11(eq)-(3-oxooctyl)-2,6-methano-3-benzazocine with 1.53 ml. (0.016 mole) of propyl iodide in 30 ml. of DMF in the presence of 1.32 g. of sodium bicarbonate.

Following a procedure similar to that described in Example 21A, using the 8-hydroxy-6(eq)-methyl-1,2,3,4,5,6-hexahydro-11(eq)-(3-oxobutyl)-2,6-methano-3-benzazocine described in Example 20A and an appropriate alkylating agent, $R_1$Hal. there are prepared the following compounds of formula I in Table 21, where in each instance $R_2$ is HO; $R_2'$, $R_2''$, $R_2'''$ and $R_3$ are each hydrogen; $R_4$ is $CH_3$; and $CH_2Z$ is $CH_2CH_2COCH_3$.

TABLE 21

| Example | $R_1$ |
|---------|-------|
| 21 P | $CH_2CH=CH_2$ |
| 21 Q | $CH_2CH=C(CH_3)_2$ |
| 21 R | $CH_2C\equiv CH$ |
| 21 S | $CH_2C\equiv CCH_3$ |
| 21 T | $CH_2CH=CCl_2$ |

Example 22

A. A solution of 4.7 g. (0.16 mole) of 6(eq)-ethyl-1,2,3,4,5,6-hexahydro-3-methyl-11(eq)-(3-oxobutyl)-2,6-methano-3-benzazocine (from the hydrochloride described in Example 18A) in 28 ml. of diethyl ether was added dropwise with stirring to 28 ml. (0.05 mole) of a 1.8 M solution of methyl lithium in diethyl ether. The mixture was stirred under nitrogen for about one hour, poured into an ice/aqueous ammonium chloride solution, and the ether layer separated and washed with water. The organic layer was dried, filtered, and taken to dryness to give 4.9 g. of residue which was converted to the methanesulfonate salt in methanol/diethyl ether. The latter was recrystallized from methanol/diethyl ether to give 2.5 g. of 3-methyl-6(eq)-ethyl-1,2,3,4,5,6-hexahydro-11(eq)-(3-methyl-3-hydroxy-butyl)-2,6-methano-3-benzazocine methanesulfonate, m.p. 173°–174° C.

Following a procedure similar to that described in Example 22A, using an appropriate 8-$R_2$-6-(eq)-$R_4$-1,2,3,4,5,6-hexahydro-3-$R_1$-11(eq)-(3-oxobutyl)-2,6-methano-3-benzazocine described above and an appropriate lower-alkyl lithium ($R_6$Li), there were prepared the 8-$R_2$-6(eq)-$R_4$-1,2,3,4,5,6-hexahydro-3-$R_1$-11(eq)-(3-methyl-3-hydroxy-lower-alkyl)-2,6-methano-3-benzazocines of formula I in Table 22a where, in each instance, $R_2'$, $R_2''$, $R_2'''$ and $R_7$ are hydrogen. Unless noted otherwise, products were isolated as, and melting points recorded for, the free base form.

TABLE 22a

| Example | $R_1/R_2$ | $R_3/R_4$ | $R_5R_6$ | Wt. S.M./Wt. Prod. | m.p.(°C.)/Solv. |
|---------|-----------|-----------|----------|-------------------|-----------------|
| 22B | $CH_3$ | H | $CH_3$ | 3.6 (base) | 203–206 |
|  | HO | $C_2H_5$ | $CH_3$ | 1.2 (base) | ethyl acetate |
| 22C | $C_3H_5$—$CH_2$ (a) | H | $CH_3$ | 4.0 (base) | 184–186 |
|  | H | $C_2H_5$ | $CH_3$ | 2.2 (HCl) | $CH_3CN$/ether |
| 22D | $C_3H_5$—$CH_2$ (a) | H | $CH_3$ | 11.4 (base) | 138–140 |
|  | HO | $CH_3$ | $CH_3$ | 3.3 (base) | ethyl acetate |
| 22E | T-$C_6H_5CH_2$ | H | $CH_3$ | 3.78 (base) | 252 |
|  | $CH_3O$ | $CH_3$ | t—$C_4H_9$ | 1.25 (HCl) | ethanol |
| 22F | $CH_3$ | H | $CH_3$ | 4.2 (base) | 182–183 |
|  | HO | $CH_3$ | $CH_3$ | 2.6 (base) | ethyl acetate |
| 22G | $CH_3$ | H | $CH_3$ | 7.5 (base) | oil |
|  | $CH_3O$ | $CH_3$ | $C_4H_9$ | 11.3 (base) |  |
| 22H | $C_6H_5CH_2$ | H | $CH_3$ | 3.78 (base) | oil |
|  | $CH_3O$ | $CH_3$ | $C_2H_5$ | 4.5 (base) |  |
| 22J | $C_3H_5$—$CH_2$ (a) | H | $CH_3$ | 13.4 (base) | 184–185 (c) |
|  | HO (C) | $CH_3$ | $C_4H_9$ | 10.2 (b) | ethanol/ether |
| 22K | $C_6H_5CH_2$ | H | $CH_3$ | 20.0 (base) | oil |
|  | $CH_3O$ | $CH_3$ | $C_3H_7$ | 21.8 (base) |  |
| 22L | $C_6H_5CH_2$ | $CH_3$ | $CH_3$ | 11.5 (base) | 223–227 |
|  | $CH_3O$ | $CH_3$ | t-$C_4H_9$ | 2.4 (HCl) | ethanol/ether |
| 22M | $C_3H_5CH_2$ (a) | H | $CH_3$ | 12.0 (base) | — |
|  | $CH_3O$ | $C_2H_5$ | t-$C_4H_9$ | 12.9 (base) | — |
| 22N | $C_6H_5CH_2$ | $CH_3$ | $CH_3$ | 18.8 (HCl) | 246–248 |

TABLE 22a-continued

| Example | $R_1/R_2$ | $R_3/R_4$ | $R_5R_6$ | Wt. S.M./Wt. Prod. | m.p.(°C.)/Solv. |
|---|---|---|---|---|---|
| | H | $CH_3$ | $t-C_4H_9$ | 3.6 (HCl) | ethanol/ether |
| 22P | $C_6H_5CH_2$ | $CH_3$ | $CH_3$ | 13.7 (base) | 233–234 |
| | $CH_3O$ | $CH_3$ | $CH_3$ | 12.1 (HCl) | ethanol/ether |
| 22Q | $C_6H_5CH_2$ | H | $t-C_4H_9$ | 37.7 (base) | 249 |
| | $CH_3O$ | $CH_3$ | $CH_3$ | 8.7 (HCl) | ethanol/ether |
| 22R | $C_6H_5CH_2$ | $CH_3$ | $t-C_4H_9$ | 11.9 (base) | 249–252 |
| | $CH_3O$ | $CH_3$ | $CH_3$ | 4.0 (HCl) | ethanol |
| 22S | $CH_3$ | $CH_3$ | $(CH_2)_2CH(CH_3)_2$ | | |
| | $CH_3O$ | $CH_3$ | $CH_3$ | 20.4 (base) (d) | |

(a) Cyclopropylmethyl
(b) Methanesulfonate
(c) Starting material was methyl ether described in Example 21B, and the product obtained from reaction with butyl lithium was cleaved, without characterization, to the 8-HO compound with sodium propanethiol using the procedure described in Example 26A.
(d) The product was separated into two isomeric pairs of racemates by high pressure liquid chromatography on silica gel in 60% hexane/40% ethyl acetate. There was thus obtained 3.6 g. of one isomer, designated Isomer I, isolated as the hydrochloride, m.p. 195–197° C. (from ethanol/ether) and 3.5 g. of another isomer, designated Isomer II, isolated as the free base, as a syrup.

Following a procedure similar to that described in Example 22A, using an appropriate 8-$R_2$-6(eq)-$R_4$-1,2,3,4,5,6-hexahydro-3-$R_1$-11(ax)-$R_3$-11(eq)—$CH_2CH_2COR_5$—2,6-methano-3-benzazocine described above and an appropriate lower-alkyl, phenyl or phenyl-lower-alkyl lithium, $R_6Li$, there are obtained the respective 8-$R_2$-6(eq)-$R_4$-1,2,3,4,5,6-hexahydro-3-$R_1$-11(ax)-$R_3$-11(eq)-$CH_2CH_2C(R_5)(R_6)OH$—2,6-methano-3-benzazocines of formula I listed in Table 22b where, in each instance, $R_2'$, $R_2''$, $R_2'''$, $R_7$ and $R_8$ are hydrogen.

TABLE 22b

| Example | $R_1$ | $R_2$ | $R_3$ | $R_4$ | $R_5$ | $R_6$ |
|---|---|---|---|---|---|---|
| 22T | $C_6H_{11}$ | $CH_3S$ | H | 3 | $CH_3$ | $CH_3$ |
| 22U | $4-BrC_6H_4CH_2CH_2$ | $CH_3O$ | H | $CH_3$ | $CH_3$ | $CH_3$ |
| 22V | $4-ClC_6H_4CH_2CH_2$ | $CH_3CONH$ | H | $CH_3$ | $CH_3$ | $CH_3$ |
| 22W | $4-FC_6H_4CH_2CH_2$ | $C_2H_5OCONH$ | H | $CH_3$ | $CH_3$ | $CH_3$ |
| 22X | $4-Cl-3-CH_3C_6H_3CH_2CH_2$ | H | H | $CH_3$ | $CH_3$ | $CH_3$ |
| 22Y | $3-CH_3COOC_6H_4CH_2CH_2$ | H | H | $CH_3$ | $CH_3$ | $CH_3$ |
| 22Z | $3,4-(CH_3O)_2C_6H_3CH_2CH_2$ | H | H | $CH_3$ | $CH_3$ | $CH_3$ |
| 22AA | $4-CH_3SC_6H_4CH_2CH_2$ | H | H | $CH_3$ | $CH_3$ | $CH_3$ |
| 22AB | $3-CF_3C_6H_4CH_2CH_2$ | H | H | $CH_3$ | $CH_3$ | $CH_3$ |
| 22AC | $3-CH_3CONHC_6H_4CH_2CH_2$ | H | H | $CH_3$ | $CH_3$ | $CH_3$ |
| 22 AD | 3,4-OCH$_2$OC$_6$H$_3$CH$_2$CH$_2$ | H | H | $CH_3$ | $CH_3$ | $CH_3$ |
| 22AE | $CH_3$ | H | H | $C_2H_5$ | $C_6H_5$ | $CH_3$ |
| 22AF | $CH_3$ | H | H | $C_2H_5$ | $CH_3$ | $C_6H_5$ |
| 22AG | $CH_3$ | H | $CH_3$ | $C_2H_5$ | $CH_3$ | $C_6H_5CH_2CH_2$ |

Example 22AH

Reaction of 3,6(eq),9-trimethyl-1,2,3,4,5,6-hexahydro-11(eq)-(3-oxobutyl)-2,6-methano-3-benzazocine (described in Example 18BJ) with methyl lithium in diethyl ether using the procedure described in Example 22A affords 3,6(eq),9-trimethyl-1,2,3,4,5,6-hexahydro-11(eq)-(3-hydroxy-3-methylbutyl)-2,6-methano-3-benzazocine.

Example 23

A. Reaction of the 3-[2-(4-fluorophenyl)ethyl]-8-ethoxycarbonylamino-6(eq)-methyl-1,2,3,4,5,6-hexahydro-11(eq)-(3-methyl-3-hydroxybutyl)-2,6-methano-3-benzazocine (described in Example 22V) with aqueous alkali in ethanol affords 3-[2-(4-fluorophenyl)ethyl]-8-amino-6(eq)-methyl-1,2,3,4,5,6-hexahydro-11(eq)-(3-methyl-3-hydroxybutyl)-2,6-methano-3-benzazocine.

Following a procedure similar to that described in Example 23A, the following 8-$R_2$-6(eq)-$R_4$-1,2,3,4,5,6-hexahydro-3-$R_1$-11(eq)-(3-methyl-3-hydroxy-lower-alkyl)-2,6-methano-3-benzazocines of formula I are also prepared:

B. 3-[2-(3-Hydroxyphenyl)ethyl]-6(eq)-methyl-1,2,3,4,5,6-hexahydro-11(eq)-(3-methyl-3-hydroxybutyl)-2,6-methano-3-benzazocine by alkaline hydrolysis of 3-[2-(3-acetoxyphenyl)ethyl]-6(eq)-methyl-1,2,3,4,5,6-hexahydro-11(eq)-(3-methyl-3-hydroxybutyl)-2,6-methano-3-benzazocine (described in Example 22X); and C. 3-[2-(3-Aminophenyl)ethyl]-6(eq)-methyl-1,2,3,4,5,6-hexahydro-11(eq)-(3-methyl-3-hydroxybutyl)-2,6-methano-3-benzazocine by alkaline hydrolysis of 3-[2-(3-acetylaminophenyl)-ethyl]-6(eq)-methyl-1,2,3,4,5,6-hexahydro-11(eq)-(3-methyl-3-hydroxybutyl)-2,6-methano-3-benzazocine (described in Example 22AB).

Example 24

A. Reaction of 8-hydroxy-3,6(eq)-dimethyl-1,2,3,4,5,6-hexahydro-11(eq)-(3-methyl-3-hydroxybutyl)-2,6-methano-3-benzazocine (described in Example 22F) with acetic anhydride affords 8-acetoxy-3,6(eq)-dimethyl-1,2,3,4,5,6-hexahydro-11(eq)-(3-methyl-3-acetoxybutyl)-2,6-methano-3-benzazocine.

Following a procedure similar to that described in Example 24A, using the 3-methyl-6(eq)-ethyl-1,2,3,4,5,6-hexahydro-11(eq)-(3-methyl-3-hydroxybutyl)-2,6-methano-3-benzazocine described in Example 22A and an appropriate acid chloride in the presence of pyridine, there are obtained the following 3-methyl-6(eq)-ethyl-1,2,3,4,5,6-hexahydro-11(eq)-(3-methyl-3-$R_7O$-butyl)-2,6-methano-3-benzazocines of formula I in Table 24 where, in each instance, $R_1$, $R_5$ and $R_6$ are $CH_3$; $R_2$, $R_2'$, $R_2''$, $R_2'''$, $R_3$ and $R_8$ are each hydrogen; and $R_4$ is $C_2H_5$.

TABLE 24

| Example | $R_7$ |
|---|---|
| 24B | $C_6H_5CO$ |
| 24C | $4$-$CH_3C_6H_4CO$ |
| 24D | $3$-$CH_3OC_6H_4CO$ |
| 24E | $4$-$ClC_6H_4CO$ |
| 24F | $4$-$BrC_6H_4CO$ |
| 24G | $4$-$FC_6H_4CO$ |
| 24H | $3$-$CF_3C_6H_4CO$ |

Example 25

A. The 3,6(eq)-dimethyl-8-methoxy-1,2,3,4,5,6-hexahydro-11(eq)-(3-oxooctyl)-2,6-methano-3-benzazocine p-toluenesulfonate (15.9 g., 0.03 mole) described in Example 18H was hydrolyzed to the free base, and the latter (10.5 g.) dissolved in diethyl ether was added to a stirred slurry of 600 mg. (0.005 mole) of lithium aluminum hydride in ether. The mixture was refluxed for one hour, quenched by the careful addition of 1.2 ml. of water in 10 ml. of tetrahydrofuran followed by excess dilute sodium hydroxide, filtered and the filtrate evaporated to dryness. The residue (10 g.) was converted to the p-toluenesulfonate salt which was recrystallized from ethanol/ether to give 6.2 g. of 3,6(eq)-dimethyl-8-methoxy-1,2,3,4,5,6-hexahydro-11(eq)-(3-hydroxyoctyl)-2,6-methano-3-benzazocine p-toluenesulfonate, m.p. 135°–137° C.

B. Reaction of 3-cyclopropylmethyl-6(eq)-ethyl-1,2,3,4,5,6-hexahydro-11(eq)-(3-oxobutyl)-2,6-methano-3-benzazocine (described in Example 18D) with lithium aluminum hydride in diethyl ether using the procedure described in Example 25A affords 3-cyclopropylmethyl-6(eq)-ethyl-1,2,3,4,5,6-hexahydro-11(eq)-(3-hydroxybutyl)-2,6-methano-3-benzazocine.

Example 26

A. A solution of 4.72 g. (0.01 mole) of 3-benzyl-6(eg)-methyl-8-methoxy-1,2,3,4,5,6-hexahydro-11(eq)-(3-hydroxy-3,4,4-trimethylpentyl)-2,6-methano-3-benzazocine (described in Example 22E) in 50 ml. of DMF was reduced with hydrogen over 0.5 g. of palladium-on-charcoal under a hydrogen pressure of about 50 p.s.i. using the procedure described in Example 3. When reduction was complete, the catalyst was removed by filtration, and the solution, containing 6(eq)-methyl-8-methoxy-1,2,3,4,5,6-hexahydro-11(eq)-(3-hydroxy-3,4,4-trimethylpentyl)-2,6-methano-3-benzazocine was treated with 1.68 g. (0.02 mole) of sodium bicarbonate and 2.0 g. (0.015 mole) of cyclopropylmethyl bromide, and the mixture was warmed with stirring on a steam bath for one hour.

The reaction mixture containing crude 3-cyclopropylmethyl-6(eq)-methyl-8-methoxy-1,2,3,4,5,6-hexahydro-11(eq)-(3-hydroxy-3,4,4-trimethylpentyl)-2,6-methano-3-benzacine, was distilled at atmospheric pressure, collecting 25 ml. of distillate, and then treated with 2.1 g. (0.05 mole) of a 57% dispersion of sodium hydride in mineral oil and 5 ml. of DMF. The mixture was cooled in an ice bath and treated dropwise with stirring under nitrogen with 4.6 ml. of propanethiol. After refluxing and stirring for about four hours, the reaction mixture was poured into a solution of aqueous ammonium chloride and extracted with 50 ml. of diethyl ether. The product was isolated in the usual manner in the form of the free base which was recrystallized from ethanol to give 2.4 g. of 3-cyclopropylmethyl-6(eq)-methyl-8-hydroxy-1,2,3,4,5,6-hexahydro-11(eq)-(3-hydroxy-3,4,4-trimethylpentyl)-2,6-methano-3-benzazocine, m.p. 195°–198° C. The methanesulfonate gave m.p. 232° C.

Following a procedure similar to that described in Example 26A, using an appropriate 8-methoxy-6(eq)-methyl-1,2,3,4,5,6-hexahydro-3-benzyl-11(ax)-$R_3$-11(eq)—$CH_2Z$—2,6-methano-3-benzazocine and an appropriate alkylating agent, $R_1$-Hal, (or reductive alkylation with formaldehyde and formic acid using the procedure described in Example 38), there were obtained the 8-hydroxy-6(eq)-methyl-1,2,3,4,5,6-hexahydro-3-$R_1$-11(ax)-$R_3$-11(eq)—$CH_2Z$—2,6-methano-3-benzazocines of formula I in Table 26 where, in each instance unless noted otherwise, $R_2$ is hydroxy; $R_2'$, $R_2''$, $R_2'''$, $R_7$ and $R_8$ are each hydrogen; and $R_4$ is $CH_3$. Compounds for which no value for $R_6$ is given are the ketones (Z is $CH_2COR_5$). The compounds are otherwise the carbinols [Z is $CH_2C(R_5)(R_6)OH$]. Melting points of the products are given in each case for the methanesulfonate salt, and yields are also given for the methanesulfonate unless noted otherwise.

TABLE 26

| Example | $R_1/R_3$ | $R_5/R_6$ | Wt. S.M./Wt. Prod | m.p. (°C.)/Solv. |
|---|---|---|---|---|
| 26B | $CH_3$ | $CH_3$ | 4.72 (HCl) | 206–208 |
|  | H | t-$C_4H_9$ | 2.7 | methanol/ether |
| 26C | $CH_3$ | $CH_3$ | 10.9 (base) | 144–146 |
|  | H | $C_3H_7$ | 7.4 (base) | acetone |
| 26D | $C_3H_5$—$CH_2^{(a)}$ | $CH_3$ | 2.5 (HCl) | 249–252 |
|  | $CH_3$ | t-$C_4H_9$ | 1.4 | methanol/ether |
| 26E | $C_3H_5$—$CH_2^{(a)}$ | $CH_3$ | 9.2 (base) | 182–183 |
|  | H | $C_3H_7$ | 1.8 | ethanol/ether |
| 26F | $C_3H_5$—$CH_2^{(a)}$ | $CH_3$ | 12.9 (base) | 225–228 |
|  | $H^{(b)}$ | t-$C_4H_9$ | 0.42 | methanol/ether |
| 26G | $C_3H_5$—$CH_2^{(a)}$ | t-$C_4H_9$ | 3.4 (HCl) | 266–268$^{(h)}$ |
|  | $CH_3$ | $CH_3^{(c)}$ | 1.4 | methanol/ether |
| 26H | $CH_3$ | t-$C_4H_9$ | 4.9 (HCl) | 219–223 (base) |
|  | $CH_3$ | $CH_3$ | 1.1 (base) | ethyl acetate |
| 26J | $CH_3$ | $CH_3$ | 11.8 (HCl) | 179–182 (base) |
|  | $CH_3$ | $CH_3$ | 1.3 (base) | ethyl acetate |
| 26K | $CH_3$ | $C_4H_9$ | 9.0 (HCl) | 283–285 (HCl) |
|  | $CH_3$ | — | 2.1 (HCl) | methanol/ether |
| 26L | $CH_3$ | t-$C_4H_9$ | 4.7 (HCl) | 190–195$^{(d)}$ |
|  | $CH_3$ | — | 1.5$^{(d)}$ | ethanol/ether |
| 26M | $C_3H_5$—$CH_2^{(a)}$ | t-$C_4H_9$ | 12.3 (HCl) | 248–250 ($CH_3SO_3H$) |
|  | H | $CH_3^{(j)}$ | 1.3 ($CH_3SO_3H$) | methanol/ether |
| 26N | $C_3H_5$—$CH_2^{(a)}$ | $CH_3$ | 11.8 (HCl) | 236–238 (HCl) |

TABLE 26-continued

| Example | $R_1/R_3$ | $R_5/R_6$ | Wt. S.M./Wt. Prod | m.p. (°C.)/Solv. |
|---|---|---|---|---|
| | $CH_3$ | $CH_3$ | 1.2 (HCl) | ethanol |
| 26P | $C_4H_7$—$CH_2$[(e)(f)] | $C_5H_{11}$ | 5.9 (HCl) | 213–216 (HCl) |
| | $CH_3$ | — | 3.2 (HCl) | isopropanol |
| 26Q | $CH_3$ | t-$C_4H_9$ | 2.4 (HCl) | 242–247[(g)] |
| | $CH_3$ | $CH_3$ | 2.4 ($CH_3SO_3H$) | methanol |
| 26R | $CH_3$ | t-$C_4H_9$ | 5.2 (HCl) | 212–215 |
| | H | $CH_3$ | 2.3 ($CH_3SO_3H$) | methanol |

[(a)]Cyclopropylmethyl
[(b)]$R_4$ is $C_2H_5$
[(c)]Isomeric with compound of Example 26D which was prepared via compound of Example 22L. Compound of Example 26G prepared via compound of Example 18L.
[(d)]Ethanesulfonate.
[(e)]Cyclobutylmethyl
[(f)]Debenzylated product reacted with 0.013 mole of cyclobutane carboxylic acid chloride in chloroform in the presence of triethylamine, and the resulting amide, without purification, converted to the ethylene glycol ketal by reaction with ethylene glycol in the presence of p-toluenesulfonic acid in toluene. The ketal was then reduced in tetrahydrofuran with lithium aluminum hydride using the procedure of Example 12A and the product, identical with the compound of Example 21F isolated from an acid medium and then cleaved with sodium propylsulfide.
[(g)]Isomeric with the compound of Example 26H. Isomers both prepared by reaction of methyl lithium with the same t-butyl ketone ($R_5$ is t-$C_4H_9$). Isomeric products, i.e. 3-benzyl-6(eq), 11(ax)-dimethyl-8-methoxy-1,2,3,4,5,6-hexahydro-11 (eq)-(3-hydroxy-3,4,4-trimethylpentyl)-2,6-methano-3-benzazocine, are readily separated from one another in the crude product by conversion to the hydrochloride salt. One isomeric form is insoluble in ethanol and gives rise to the isomer of Example 26H. The other, much more soluble in ethanol, gives rise to the isomer of Example 26Q. The isomer of Example 26Q predominates over that of Example 26H when methyl lithium is reacted with the t-butyl ketone. The opposite is true when t-butyl lithium is reacted with the methyl ketone ($R_5$ is $CH_3$).
[(h)]Samples of the free base were resolved into the two optical isomers by treating the corresponding racemic des N-cyclopropyl methyl ether ($R_1$ is hydrogen and $R_2$ is $CH_3O$) with d- and l- mandelic acid. The former afforded the corresponding d-base . d-mandelate (m.p. 163–166° C., from ethyl acetate) and the latter the corresponding l-base . l-mandelate (m.p. 162–165° C., from ethyl acetate). Conversion of each of these to the free bases and conversion of the free bases to the corresponding N-cyclopropylmethyl-8-hydroxy compounds using the procedure described in Example 26A, and isolation of the products in the form of the methanesulfonate salts afforded the respective d-base . methanesulfonate, m.p. 279–282° C. (from methanol), $[\alpha]_D^{25} = +61.0$ and l-base . methanesulfonate, m.p. 281–285° C. (from methanol), $[\alpha]_D^{25} = -61.3°$.
[(i)]Isomeric with compound of Example 26A which was prepared via compound of Example 18E. Compound of Example 26M prepared via compound of Example 18K.

EXAMPLE 27

Using a procedure similar to that described above in Example 26A, 3.19 g. (0.007 mole) of 3-benzyl-6(eq), 11(ax)-dimethyl-1,2,3,4,5,6-hexahydro-11(eq)-(3-hydroxy-3,4,4-trimethylpentyl)-2,6-methano-3-benzazocine (described in Example 22 N) was debenzylated by reduction over 0.35 g. of palladium-on-charcoal and the resulting 6(eq), 11(ax)-dimethyl-1,2,3,4,5,6-hexahydro-11(eq)-(3-hydroxy-3,4,4-trimethylpentyl)-2,6-methano-3-benzazocine reacted with 2.0 g. (0.015 mole) of cyclopropylmethyl bromide and 1.7 g. (0.020 mole) of sodium bicarbonate and the product isolated in the form of the hydrochloride salt to give 1.5 g. of 3-cyclopropylmethyl-6(eq), 11(ax)-dimethyl-1,2,3,4,5,6-hexahydro-11(eq)-(3-hydroxy-3,4,4-trimethylpentyl)-2,6-methano-3-benzazocine hydrochloride, m.p. 232°–233° C. (from ethanol/ether).

EXAMPLE 28

A. A solution of 15 g. (0.04 mole) of 3-benzyl-8-methoxy-6(eq)-methyl-1,2,3,4,5,6-hexahydro-11(eq)-(3-oxo-butyl)-2,6-methano-3-benzazocine (described in Example 18E) was catalytically debenzylated and the resulting nor-base alkylated with cyclopropylmethyl bromide in the presence of sodium bicarbonate using the procedure described in Example 26A. The resulting 3-cyclopropylmethyl-8-methoxy-6(eq)-methyl-1,2,3,4,5,6-hexahydro-11(eq)-(3-oxobutyl)-2,6-methano-3-benzazocine (12.9 g.) was dissolved in 125 ml. of toluene and added to 45 ml. of a 2.1 M solution of n-butyl lithium in hexane at −65° C. using the procedure described in Example 22A. The resulting 3-cyclopropyl-methyl-8-methoxy-6(eq)-methyl-1,2,3,4,5,6-hexahydro-11(eq)-(3-hydroxy-3-methylheptyl)-2,6-methano-3-benzazocine (13.4 g.) was dissolved in 130 ml. of DMF and the ether group cleaved by treatment with 7.1 g. (0.168 mole) of a 57% mineral oil dispersion of sodium hydride and 12.8 g. (0.168 mole) of propanethiol in the manner described above in Example 26A. The product was converted to the methanesulfonate salt which was recrystallized from ethanol/ether to give 10.2 g. of 3-cyclopropylmethyl-8-hydroxy-6(eq)-methyl-1,2,3,4,5,6-hexahydro-11(eq)-(3-hydroxy-3-methylheptyl)-2,6-methano-3-benzazocine methanesulfonate, m.p. 184°–185° C.

Following a procedure similar to that described in Example 28A, using the 3-benzyl-8-methoxy-6(eq)-methyl-1,2,3,4,5,6-hexahydro-11(eq)-3-oxobutyl)-2,6-methano-3-benzazocine described in Example 18E, ethyl lithium and an appropriate alkylating agent, $R_1$-Hal, (or reductive alkylation with formaldehyde and formic acid using the procedure described in Example 42), there were obtained the 8-hydroxy-3-$R_1$-6(eq)-methyl-1,2,3,4,5,6-hexahydro-11(eq)-(3-hydroxy-3-methylpentyl)-2,6-methano-3-benzazocines of formula I in Table 28 where, in each instance, $R_2$ is hydroxy; $R_2'$, $R_2''$, $R_2'''$, $R_3$, $R_7$ and $R_8$ are hydrogen; $R_4$ and $R_5$ are $CH_3$; and $R_6$ is $C_2H_5$. In each instance, the melting points are given for the methanesulfonate salt, and the yield of product is given for the free base.

TABLE 28

| Example | $R_1$ | Wt.S.M./Wt.Prod. | M.P.(°C.)/Solv. |
|---|---|---|---|
| 28B | cyclopropyl—$CH_2$ | 15.0 (base) | 195–196 |
| | | 8.3 (base) | acetone |
| 28C | $CH_3$ | 15.0 (base) | 155–157 |
| | | 11.0 (base) | ethanol |

EXAMPLE 29

A. A 5.7 g. sample of 3-methyl-8-methoxy-6(eq)-methyl-1,2,3,4,5,6-hexahydro-11(eq)-(3-hydroxy-3-methylheptyl)-2,6-methano-3-benzazocine described in Example 22G in DMF was cleaved with sodium propylsulfide (0.063 mole) using the procedure described in Example 26A and the product (3.4 g. of crude base) converted to the methanesulfonate salt which was recrystallized from ethanol/ether to give 2.6 g. of 3-methyl-8-hydroxy-6(eq)-methyl-1,2,3,4,5,6-hexahydro-11(eq)-(3-hydroxy-3-methylheptyl)-2,6-methano-3-benzazocine methanesulfonate, m.p. 184°–186° C.

Following a procedure similar to that described in Example 29A using an appropriate 8-methoxy-6(eq)-methyl-11(ax)-$R_3$-1,2,3,4,5,6-hexahydro-3-$R_1$-11(eq)-$CH_2Z$-2,6-methano-3-benzazocine, the following 8-hydroxy-6(eq)-methyl-11(ax)-$R_3$-1,2,3,4,5,6-hexahydro-3-$R_1$-11(eq)-$CH_2Z$-2,6-methano-3-benzazocines of formula I were prepared where, in each case, $R_2'$, $R_2''$, $R_2'''$, $R_7$ and $R_8$ are hydrogen; $R_4$ is $CH_3$; and $R_2$ is hydroxy. Where no value for $R_6$ is given, the compound has the ketone structure (Z is $CH_2COR_5$) but otherwise has the carbinol structure [Z is $CH_2C(R_5)(R_6)OH$].

(0.028 mole) of 3,6(eq)-dimethyl-8-methoxy-1,2,3,4,5,6-hexahydro-11(eq)-(3-methyl-2-butenyl)-2,6-methano-3-benzazocine as an oil which, without further characterization, was cleaved with 0.15 mole of sodium propylsulfide in 75 ml. of DMF using the procedure described in Example 26A. The product was converted to the methanesulfonate salt which was recrystallized from ethanol to give 1.6 g. of 3,6(eq)-dimethyl-8-hydroxy-1,2,3,4,5,6-hexahydro-11(eq)-(3-methyl-2-butenyl)-2,6-methano-3-benzazocine methanesulfonate, m.p. 226°–229° C.

Following a procedure similar to that described in Example 30A, using the 7-$R_2$-1-$R_1$-3-$C(R_5)(R_6)OR_7$-4aα-$R_3$-5α-$R_4$-1,2,3,4,4a,5,10,10a-octahydro-2,5-methanobenzo[g]quinolines described in Examples 9A, 9B, 9C, 9D, 9G, 9E, 11A, 11C and 13A in refluxing mesitylene/formic acid, there are obtained the respective 8-$R_2$-6(eq)-$R_4$-1,2,3,4,5,6-hexahydro-3-$R_1$-11(ax)-$R_3$-11(eq)-(2-lower-alkenyl)-2,6-methano-3-benzazocines of formula I in Table 30 where, in each instance, $R_2'$, $R_2''$, $R_2'''$ and $R_8$ are hydrogen, and Z is —CH=$CR_5R_6$.

TABLE 29

| Example | $R_1/R_3$ | $R_5/R_6$ | Wt. S.M./Wt. Prod. | m.p.(°C.)/Solv. |
|---|---|---|---|---|
| 29B | $CH_3$ | $C_5H_{11}$ | 6.4 (base) | 176–177 (a) |
|  | H | H | 1.8 (a) | acetone |
| 29C | $C_3H_5$—$CH_2$ | $C_4H_9$ | 5.0 (base) | 235–237 (HCl) |
|  | $CH_3$ | — | 2.5 (HCl) | isopropanol |
| 29D | $CH_3$ | $CH_2CH_2$—$C_3H_5$ | 6.2 (base) | 128–130 (b) |
|  | $CH_3$ | — | 0.9 (base) | ethyl acetate/hexane |
| 29E | $CH_3$ | $(CH_2)_2CH(CH_3)_2$ (c) | 2.9 (HCl) | 204–206 |
|  | $CH_3$ | $CH_3$ | 2.13 ($CH_3SO_3H$) | methanol/ether |
| 29F | $CH_3$ | $(CH_2)_2CH(CH_2)_2$ (d) | 3.15 (base) | 238–241 |
|  | $CH_3$ | $CH_3$ | 1.48 (HCl) | ethanol/ether |

(a) p-Toluenesulfonate
(b) The hydrochloride has m.p. 271–273° C. (from methanol/ether)
(c) Isomer I, prepared from Isomer I of Example 22S, and isomeric with compound of Example 29F.
(d) Isomer II, prepared from Isomer II of Example 22S, and isomeric with compound of Example 29E.

EXAMPLE 30

A. A solution of 1.8 g. (0.0046 mole) of 1-benzyl-3-(2-hydroxy-2-propyl)-5α-methyl-7-methoxy-1,2,3,4,4a,5,10,10a-octahydro-2,5-methanobenzo[g]quinoline hydrochloride (described in Example 11D) was dissolved in 100 ml. of mesitylene and the solution treated with 3.8 ml. (0.1 mole) of formic acid and refluxed and stirred for about twenty-four hours. On cooling, the mixture was extracted with three 5 ml. portions of 1 M phosphoric acid, and the combined aqueous extracts washed twice with diethyl ether and then basified by the cautious addition of 6.6 g. of potassium hydroxide pellets. The oil which separated was extracted with diethyl ether, and the ether extracts worked up in the usual manner to give an oil which was converted to the hydrochloride salt. The latter was recrystallized from ethanol/ether to give 0.3 g. of 3-benzyl-6(eq)-methyl-8-methoxy-1,2,3,4,5,6-hexahydro-11(eq)-(3-methyl-2-butenyl)-2,6-methano-3-benzazocine hydrochloride, m.p. 232°–235° C.

B. Following a procedure similar to that described in Example 30A, 19.6 g. (0.062 mole) of 1-methyl-3-(2-hydroxy-2-propyl)-5α-methyl-7-methoxy-1,2,3,4,4a,5,10,10a-octahydro-2,5-methanobenzo[g]quinoline described in Example 9F in 1 liter of mesitylene and 38 ml. of formic acid was heated and stirred under reflux for twenty-four hours and worked up in the manner described in Example 30A to give 8.5 g.

TABLE 30

| Example | $R_1$ | $R_2$ | $R_3$ | $R_4$ | $R_5$ | $R_6$ |
|---|---|---|---|---|---|---|
| 30C | $CH_3$ | H | H | $C_3H_7$ | $CH_3$ | $CH_3$ |
| 30D | $CH_3$ | H | H | $C_2H_5$ | $CH_3$ | $CH_3$ |
| 30E | $CH_3$ | H | H | $CH_3$ | $CH_3$ | $CH_3$ |
| 30F | $CH_3$ | HO | H | $C_2H_5$ | $CH_3$ | $CH_3$ |
| 30G | cyclopropyl-$CH_2$ | H | H | $C_2H_5$ | $CH_3$ | $CH_3$ |
| 30H | $C_6H_5CH_2CH_2$ | H | H | $C_2H_5$ | $CH_3$ | $CH_3$ |
| 30J | $CH_3$ | H | H | $C_2H_5$ | $CH_3$ | $C_3H_7$ |
| 30K | $CH_3$ | H | $CH_3$ | $C_2H_5$ | $CH_3$ | $CH_3$ |
| 30L | $CH_3$ | H | H | $C_2H_5$ | $CH_3$ | H |

EXAMPLE 31

A. To a solution of 0.042 mole of diisopropylamide in hexane (prepared from 16.8 ml. of a 2.5 M solution of butyl lithium in hexane and 4.2 g. of diisopropylamine) was added a solution of 2.72 g. (0.02 mole) of phenylacetic acid in 200 ml. of tetrahydrofuran (THF) over a twenty minute period while maintaining the temperature at 0° to −5° C. The mixture was stirred for about one hour at 0° C. and then treated with a solution of 3.45 g. (0.01 mole) of ethyl β-[3,6(eq), 11(ax)-trimethyl-8-methoxy-1,2,3,4,5,6-hexahydro-2,6-methano-3-benzazocine-11(eq)-yl]propionate in 25 ml. of THF. The mixture was stirred at ambient temperature for about two hours, the solvent removed in vacuo and the residual gum was treated with 30 ml. of dilute hydrochloric acid and 75 ml. of water. The mixture was refluxed with stirring for about an hour, poured onto ice, basified with 10% sodium hydroxide and extracted three times with ether. Washing of the combined extracts with saturated brine, drying over anhydrous magnesium sulfate and evaporation to dryness afforded 4.0 g. of an oil which was dissolved in acetone and treated with a solution of methanesulfonic acid in acetone. There was thus obtained 2.2 g. of 3,6(eq),11(ax)-trimethyl-8-methoxy-1,2,3,4,5,6-hexahydro-11(eq)-(3oxo-4-phenylbutyl)-2,6-methano-3-benzazocine methanesulfonate, m.p. 189°–192° C.

B. Following a procedure similar to that described in Example 31A, 6.5 g. (0.043 mole) of 3-methylphenylacetic acid was reacted with 0.096 mole of diisopropylamide (prepared from 47 ml. of a 2.0 M solution of n-butyl lithium in hexane and 9.6 g. of diisopropylamine) and the resulting lithio salt reacted with 7.5 g. (0.022 mole) of ethyl β-[3,6(eq), 11(ax)-trimethyl-8-methoxy-1,2,3,4,5,6-hexahydro-2,6-methano-3-benzazocine-11(eq)-yl]propionate in 400 ml. of THF. The product was isolated in the form of the free base to give 7.4 g. of 3,6(eq),11(ax)-trimethyl-8-methoxy-1,2,3,4,5,6-hexahydro-11(eq)-[3-oxo-4-(3-methylphenyl)butyl]-2,6-methano-3-benzazocine as an oil. A small amount was converted to the hydrochloride salt which, on repeated recrystallization from methanol/ether, afforded material having m.p. 180°–181° C.

EXAMPLE 32

A solution of 5.0 g. (0.013 mole) of 3,6(eq), 11(ax)-trimethyl-8-hydroxy-1,2,3,4,5,6-hexahydro-11(eq)-(3-oxooctyl)-2,6-methano-3-benzazocine hydrochloride, 1.25 g. (0.017 mole) of hydroxylamine hydrochloride and 1.25 g. of sodium acetate in 50 ml. of ethanol and 10 ml. of water was heated on a steam bath for thirty minutes. The mixture was then cooled to room temperature and diluted with 100 ml. of water and the solid which separated was collected and dried to give 4 g. of crude product which was boiled with toluene for about an hour and then collected and dried to give 3.0 g. of 3,6(eq),11(ax)-trimethyl-8-hydroxy-1,2,3,4,5,6-hexahydro-11(eq)-(3-oxooctyl)-2,6-methano-3-benzazocine oxime hydrochloride, m.p. 214°–216° C.

EXAMPLE 33

A. A solution of 6.9 g. (0.018 mole) of 3,6(eq), 11(ax)-trimethyl-8-hydroxy-1,2,3,4,5,6-hexahydro-11(eq)-(3-oxooctyl)-2,6-methano-3-benzazocine hydrochloride, 2.1 g. (0.019 mole) of O-carboxymethylhydroxylamine hemihydrochloride and 5.2 g. (0.038 mole) of sodium acetate in 100 ml. of ethanol and 30 ml. of water was refluxed for about twelve hours, diluted with 50 ml. of hot water, and the solid which separated was collected and dried to give 5.5 g. of 3,6(eq),11(ax)-trimethyl-8-hydroxy-1,2,3,4,5,6-hexahydro-11(eq)-(3-oxooctyl)-2,6-methano-3-benzazocine O-carboxymethyloxime hydrate.

B. Following a procedure similar to that described in Example 33A, 7.96 g. (0.02 mole) of 3,6(eq),11(ax)-trimethyl-8-hydroxy-1,2,3,4,5,6-hexahydro-11(eq)-(3-oxo-6-methylheptyl)-2,6-methano-3-benzazocine hydrochloride was reacted with 2.4 g. (0.02 mole) of carboxymethylhydroxylamine hemihydrochloride in 100 ml. of ethanol and 30 ml. of water in the presence of 6.0 g. of sodium acetate to give 6.5 g. of 3,6(eq),11(ax)-trimethyl-8-hydroxy-1,2,3,4,5,6-hexahydro-11(eq)-(3-oxo-6-methylheptyl)-2,6-methano-3-benzazocine O-carboxymethyloxime hydrate.

The preparation of the compounds of Formula I using the process of Lewis and Michne U.S. Pat. No. 4,119,628 and c.i.p. thereof, application Ser. No. 878,308, now U.S. Pat. No. 4,148,794, patented Apr. 10, 1979, is illustrated by the following preparations in Examples 34A–34T, inclusive.

EXAMPLE 34

A. A solution of 24.5 g. (0.056 mole) of ethyl 3-(1-oxo-3-cyclopropylpropyl)-7-methoxy-1,4aα,5α-trimethyl-1,2,3,4,4a,5,10,10a-octahydro-2,5-methanobenzo[g]quinoline-3-carboxylate in a solution of 1120 ml. of mesitylene and 42 ml. of formic acid was stirred and refluxed at 117° C. for twenty-four hours. The mixture was extracted with 420 ml. of water and 60 ml. of dilute hydrochloric acid, the organic layer washed with water, and the combined aqueous layers extracted once with diethyl ether and basified with 35% sodium hydroxide. Extraction of the aqueous layer with diethyl ether, washing the ether extracts first with water, then with brine, drying and evaporation to dryness afforded 5.3 g. of an oil which was dissolved in ethanol and treated with ethereal hydrogen chloride. There was thus obtained 4.6 g. of 3,6(eq),11(ax)-trimethyl-8-methoxy-1,2,3,4,5,6-hexahydro-11(eq)-(3-oxo-5-cyclopropylpentyl)-2,6-methano-3-benzazocine hydrochloride, m.p. 224°–226° C. whose preparation is also described above in Example 18 AG.

Following a procedure similar to that described in Example 34A, using an appropriate lower-alkyl 1-R$_1$-3-R$_5$CO—4aα-R$_3$-5α-R$_4$-7-R$_2$-1,2,3,4,4a,5,10,10a-octahydro-2,5-methanobenzo[g]quinoline-3-carboxylate of formula IX, which are described in Lewis and Michne U.S. Pat. No. 4,119,628 and c.i.p. thereof Ser. No. 878,308, New U.S. Pat. No. 4,148,794, patented Apr. 10, 1979 there were prepared the 3-R$_1$-6(eq)-R$_4$-11(ax)-R$_3$-1,2,3,4,5,6-hexahydro-11(eq)—CH$_2$CH$_2$COR$_5$—2,6-methano-3-benzazocines of formula I in Table 34 where, in each instance, R$_2'$, R$_2''$ and R$_2'''$ are hydrogen and Z is CH$_2$COR$_5$. The Example numbers where the alternative preparations of the same species from the 7-R$_2$-1-R$_1$-3—COR$_5$—4aα-R$_3$-5α-R$_4$-1,2,3,4,4a,5,10,10a-octahydro-2,5-methanobenzo[g]quinolines of formula II have been described above are given in parentheses in the column headed "Example". The reaction conditions used, that is procedure A described in Example 18A using trimethylammonium formate or procedure B described in Example 18B using formic acid in refluxing mesitylene, are also indicated in the column headed "Example" by the respective designations A and B.

TABLE 34

| Example | R$_1$/R$_2$ | R$_3$/R$_4$ | R$_5$ | Wt. S.M. Wt. Prod. | M.P. (°C.) Solv. |
|---|---|---|---|---|---|
| 34B(18AA) | CH$_3$ | CH$_3$ | CH$_3$ | 57.1(base) | 183–186 |
| B | CH$_3$O | CH$_3$ | | 6.6(HCl) | ethanol/ether |
| 34C(18U) | C$_6$H$_5$CH$_2$ | CH$_3$ | (CH$_2$)$_4$CH$_3$ | 139.9(base) | 223–227 |
| B | CH$_3$O | CH$_3$ | | 35.9(HCl) | ethanol/ether |
| 34D(18AB) | CH$_3$ | CH$_3$ | (CH$_2$)$_4$CH$_3$ | 24.1(base) | oil |
| B | H | CH$_3$ | | 17.8(base) | |
| 34E(18AR) | CH$_3$ | CH$_3$ | (CH$_2$)$_4$CH$_3$ | 7.0(base) | 225–227.5 |

TABLE 34-continued

| Example | $R_1/R_2$ | $R_3/R_4$ | $R_5$ | Wt. S.M. Wt. Prod. | M.P. (°C.) Solv. |
|---|---|---|---|---|---|
| B | $CH_3O$ | $C_2H_5$ | | 4.1(HCl) | acetone/ether |
| 34F(18AC) | $CH_3$ | $CH_3$ | $(CH_2)_2CH(CH_3)_2$ | 27.9(base) | oil |
| B | H | $CH_3$ | | 20.7(base) | |
| 34G(18AS) | $C_6H_5CH_2$ | $CH_3$ | $(CH_2)_2CH(CH_3)_2$ | 75.9(base) | oil |
| B | $CH_3O$ | $CH_3$ | | 57.1(base) | |
| 34H(18AD) | $CH_3$ | H | $(CH_2)_2CH(CH_3)_2$ | 28.3(base) | 159–162.5 |
| B | $CH_3O$ | $CH_3$ | | 9.8(oxalate) | ethanol/ether |
| 34J(18AT) | $CH_3$ | $CH_3$ | $(CH_2)_2CH(CH_3)_2$ | 31.2(base) | 250–252 |
| B | $CH_3O$ | $C_2H_5$ | | 7.3(HCl) | ethanol/ether |
| 34K(18AF) | $CH_3$ | $CH_3$ | $(CH_2)_3CH(CH_3)_2$ | 23.7(base) | 197–200 |
| B | $CH_3O$ | $CH_3$ | | 8.2(HCl) | ethanol/ether |
| 34L(18AE) | $CH_3$ | | $(CH_2)_2CH(CH_3)_2$ | 13.5(base) | 169–173 |
| B | $CH_3O$ | $\mid$<br>$(CH_2)_4$<br>$\mid$ | | 6.6(HCl) | ethanol/ether |
| 34M(18AH) | $CH_3$ | $CH_3$ | $CH_2C_4H_7$ | 20(base) | oil |
| A | $CH_3O$ | $CH_3$ | | 8.9(base) | |
| 34N(18AJ) | $CH_3$ | $CH_3$ | $(CH_2)_2C_5H_9$ | 43.7(base) | 219–223 |
| B | $CH_3$ | $CH_3$ | | 19.5(HCl) | ethanol/ether |
| 34P(18AK) | $CH_3$ | $CH_3$ | $(CH_2)_2C_5H_9$ | 20.6(base) | 231–235[a] |
| B | H | $CH_3$ | | 8.5($H_2SO_4$) | ethanol/ether |
| 34Q(18AM) | $CH_3$ | $CH_3$ | $C_6H_5$ | 21.6(base) | 94–97 |
| B | H | $CH_3$ | | 6.0(base) | ethanol |
| 34R(18AN) | $CH_3$ | $CH_3$ | $C_6H_5$ | 35.2(base) | 102–106 |
| B | $CH_3O$ | $CH_3$ | | 14.8(base) | ethanol |
| 34S(18AP) | $CH_3$ | $CH_3$ | $C_6H_4CH_3(3)$ | 12.6(base) | 94–96 |
| A | $CH_3O$ | $CH_3$ | | 6.9(base) | methanol |
| 34T(18AQ) | $CH_3$ | $CH_3$ | $C_6H_4CH_3(4)$ | 4.0(base) | 87–89 |
| A | $CH_3O$ | $CH_3$ | | 2.1(base) | methanol |
| 34U(18AV) | $CH_3$ | $CH_3$ | $(CH_2)_2C_4H_7$ | 12.4(base) | 153–155 |
| A | $CH_3O$ | $CH_3$ | | 8.3($CH_3SO_3H$) | acetone/ether |

[a]The free base was obtained as an amber oil.

EXAMPLE 35

A. Two grams of the solid hydrochloride salt obtained as an initial precipitate from the ethanol/ether crystallization in Example 18A was recrystallized once again from ethanol/ether to give 1.3 g. of 1,2-dimethyl-5α-ethyl-1,2,3,4,4a,5,10,10a-octahydro-3,5-ethenobenzo[g]quinoline hydrochloride, m.p. 262°–264° C.

A solution of 5.3 g. (0.017 mole) of the latter in 50 ml. of ethanol was reduced with 0.1 g. of platinum oxide. When reaction was complete, the catalyst was removed by filtration, and the product isolated in the form of the hydrochloride salt in the usual manner to give 2.4 g. of 1,2-dimethyl-5α-ethyl-1,2,3,4,4a,5,10,10a-octahydro-3,5-ethanobenzo[g]quinoline hydrochloride m.p. 319°–329° C.

The following 1-$R_1$-2-methyl-4aα-$R_3$-5α-ethyl-1,2,3,4,4a,5,10,10a-octahydro-3,5-ethenobenzo[g]quinolines of formula IIIa in Table 35a where, in each instance, $R_2$, $R_2'$, $R_2''$ and $R_2'''$ are hydrogen; $R_4$ is $C_2H_5$ and Q is $CH_3$ were obtained as byproducts with the main products of Examples 18C and 18D, respectively. The yields and melting points for the compounds of Examples 35B and 35C are given for the hydrochloride and p-toluenesulfonate salts, respectively.

TABLE 35a

| Example | $R_1$ | $R_3$ | Wt. II/Wt. IIIa | m.p. (°C.)/Solv. |
|---|---|---|---|---|
| 35B | $CH_3$ | $CH_3$ | 10 (base)<br>1.2 | 234–235<br>acetone |
| 35C | cyclopropyl-$CH_2$ | H | 16 (base)<br>2.5 | 187–189<br>ethyl acetate |

The following 1$R_1$-2-Q-4aα-$R_3$-5α-$R_4$-7-$R_2$-8-$R_2'$-1,2,3,4,4a,5,10,10a-octahydro-3,5-ethenobenzo[g]quinolines of formula IIIa, where $R_2''$ and $R_2'''$ in each instance are hydrogen, are obtained as by-products from the preparations described, respectively, in Example 18E, 18K, 18P, 18Q, 18R, 18S, 18T, 18U, 18V, 18W, 18X, 18Y, 18Z, 18AA, 18AB, 18AC, 18AD, 18AE, 18AF, 18AG, 18AH, 18AJ, 18AK, 18AL, 18AM, 18AN, 18AQ, 18AR, 18AS, 18AT, 18AU and 10D.

TABLE 35b

| Example | $R_1/Q$ | $R_2/R_2'$ | $R_3/R_4$ |
|---|---|---|---|
| 35D | $C_6H_5CH_2$<br>$CH_3$ | $CH_3O$<br>H | H<br>$CH_3$ |
| 35E | $C_6H_5CH_2$<br>$CH_3$ | H<br>H | H<br>$C_2H_5$ |
| 35F | $CH_3$<br>$C_3H_7$ | H<br>H | H<br>$C_2H_5$ |
| 35G | $C_6H_{11}$<br>$CH_3$ | $CH_3S$<br>H | H<br>$CH_3$ |
| 35H | 4-$BrC_6H_4CH_2CH_2$<br>$CH_3$ | $CH_3O$<br>H | H<br>$CH_3$ |
| 35J | 4-$ClC_6H_4CH_2CH_2$<br>$CH_3$ | $CH_3CONH$<br>H | H<br>$CH_3$ |
| 35K | 4-$FC_6H_4CH_2CH_2$<br>$CH_3$ | $C_2H_5OCONH$<br>H | H<br>$CH_3$ |
| 35L | 4-Cl-3-$CH_3C_6H_3CH_2CH_2$<br>$CH_3$ | H<br>H | H<br>$CH_3$ |
| 35M | 3-$CH_3COOC_6H_4CH_2CH_2$<br>$CH_3$ | H<br>H | H<br>$CH_3$ |
| 35N | 3,4-$(CH_3O)_2C_6H_3CH_2CH_2$<br>$CH_3$ | H<br>H | H<br>$CH_3$ |
| 35P | 4-$CH_3SC_6H_4CH_2CH_2$<br>$CH_3$ | H<br>H | H<br>$CH_3$ |
| 35Q | 3-$CF_3C_6H_4CH_2CH_2$<br>$CH_3$ | H<br>H | H<br>$CH_3$ |
| 35R | 3-$CH_3CONHC_6H_4CH_2CH_2$<br>$CH_3$ | H<br>H | H<br>$CH_3$ |
| 35S | ⌈‾‾‾⌉<br>3,4-$OCH_2OC_6H_3CH_2CH_2$<br>$CH_3$ | H<br>H | H<br>$CH_3$ |
| 35T | $CH_3$<br>$CH_3$ | H<br>Cl | H<br>$CH_3$ |
| 35U | $CH_3$<br>$CH_3$ | H<br>Br | H<br>$CH_3$ |

TABLE 35b-continued

| Example | R₁/Q | R₂/R₂' | R₃/R₄ |
|---|---|---|---|
| 35V | CH₃<br>CH₃ | H<br>F | H<br>CH₃ |
| 35W | CH₃<br>CH₃ | H<br>CF₃ | H<br>CH₃ |
| 35X | CH₃<br>CH₃ | H<br>CH₃ | H<br>CH₃ |
| 35Y | CH₃<br>CH₃ | C₆H₅<br>H | H<br>CH₃ |
| 35Z | CH₃<br>CH₃ | H<br>CH₂<O-O (methylenedioxy) | H<br>CH₃ |
| 35AA | CH₃<br>CH₃ | H<br>H | H<br>H |
| 35AB | CH₃<br>CH₃ | H<br>H | H<br>CH₂CH₂Cl |
| 35AC | CH₃<br>CH₃ | H<br>H | H<br>(CH₂)₃ (cyclic) |
| 35AD | CH₃<br>CH₃ | H<br>H | H<br>(CH₂)₄ (cyclic) |
| 35AE | CH₃<br>CH₃ | H<br>H | H<br>CH₂CH₂OCH₃ |
| 35AF | CH₃<br>CH₃ | H<br>H | H<br>CH₂CH₂SC₆H₅ |
| 35AG | CH₃<br>CH₃ | H<br>H | H<br>CH₂CH₂SOC₆H₅ |
| 35AH | CH₃<br>CH₃ | H<br>H | H<br>CH=CH₂ |
| 35AJ | CH₃<br>CH₃ | H<br>H | H<br>CH₂CH₂SCH₃ |
| 35AK | CH₃<br>CH₃ | H<br>H | H<br>CH₂CH₂OH |
| 35AL | CH₃<br>C₆H₅ | H<br>H | H<br>C₂H₅ |

EXAMPLE 35AM

Heating the 1,5α,8-trimethyl-3-acetyl-1,2,3,4,4a,5,10,-10a-octahydro-2,5-methanobenzo[g]quinoline described in Example 2AR with formic acid in mesitylene using the procedure described in Example 18B affords, in addition to the benzazocine of formula I described in Example 18AU, 1,2,5α,8-tetramethyl-1,2,3,4,4a,5,10,-10a-octahydro-3,5-ethenobenzo[g]-quinoline.

Reduction of the compounds disclosed in Examples 35D-35AM, inclusive, with hydrogen over platinum oxide using the procedure described in Example 35A affords the corresponding 1-R₁-2-Q-4aα-R₃-5α-R₄-7-R₂-8-R₂'-1,2,3,4,4a,5,10,10a-octahydro-3,5-ethanobenzo[g]quinolines of formula IIIb.

EXAMPLE 36

A. Hydrolysis with aqueous alkali in an ethanol solvent of 1-[2-(4-chlorophenyl)ethyl]-7-acetylamino-2,5α-dimethyl-1,2,3,4,4a,5,10,10a-octahydro-3,5-ethenobenzo[g]quinoline and 1-[2-(4-chlorophenyl)ethyl]-7-acetylamino-2,5α-dimethyl-1,2,3,4,4a,5,10,10a-octahydro-3,5-ethanobenzo[g]quinoline (described in Example 35J) afford, respectively, 7-amino-1-[2-(4-chlorophenyl)ethyl]-2,5α-dimethyl-1,2,3,4,4a,5,10,10a-octahydro-3,5-ethenobenzo[g]quinoline and 7-amino-1-[2-(4-chlorophenyl)ethyl]-2,5α-dimethyl-1,2,3,4,4a,5,10,10a-octahydro-3,5-ethanobenzo[g]quinoline.

Following a procedure similar to that described in Example 36A, the following compounds of formulas IIIa and IIIb are similarly prepared:

B. 7-Amino-1-[2-(4-fluorophenyl)ethyl]-2,5α-dimethyl-1,2,3,4,4a,5,10,10a-octahydro-3,5-ethenobenzo[g]quinoline and 7-amino-1-[2-(4-fluorophenyl)ethyl]-2,5α-dimethyl-1,2,3,4,4a,5,10,10a-octahydro-3,5-ethanobenzo[g]quinoline, by alkaline saponification, respectively, of 1-[2-(4-fluorophenyl)ethyl]-2,5α-dimethyl-7-ethoxycarbonylamino-1,2,3,4,4a,5,10,10a-octahydro-3,5-ethenobenzo[g]quinoline and 1-[2-(4-fluorophenyl)-ethyl]-2,5α-dimethyl-7-ethoxycarbonylamino-1,2,3,4,4a,5,10,10a-octahydro-3,5-ethanobenzo[g]quinoline (described in Example 35K);

C. 1-[2-(3-Aminophenyl)ethyl]-2,5α-dimethyl-1,2,3,4,4a,5,10,10a-octahydro-3,5-ethenobenzo[g]quinoline and 1-[2-(3-aminophenyl)ethyl]-2,5α-dimethyl-1,2,3,4,4a,5,10,10a-octahydro-3,5-ethanobenzo[g]quinoline, by alkaline saponification, respectively, of 1-[2-(3-acetylaminophenyl)ethyl]-2,5α-dimethyl-1,2,3,4,4a,5,10,10a-octahydro-3,5-ethenobenzo[g]quinoline and 1-[2-(3-acetylaminophenyl)ethyl]-2,5α-dimethyl-1,2,3,4,4a,5,10,10a-octahydro-3,5-ethanobenzo[g]quinoline (described in Example 35R).

EXAMPLE 37

A solution of 88 g. (0.33 mole) of 2-(4-methoxybenzyl)-8-methylene-3-azabicyclo[3.3.1]non-6-en-4-one (described in Example 15A) was dissolved in a solution of 800 ml. of glacial acetic acid and 180 ml. of concentrated sulfuric acid, and the mixture stirred and heated on a steam bath for one hour. The mixture was then poured into four liters of an ice/water mixture. The gum which separated slowly solidified and was collected and recrystallized three times from DMF to give 4.3 g. of 7-methoxy-5α-methyl-3,4,4a,5,10,10a-hexahydro-3,5-ethenobenzo[g]quinoline-2(1H)-one, m.p. 268°-272° C.

EXAMPLE 38

A solution of 5.38 g. (0.02 mole) of 7-methoxy-5α-methyl-3,4,4a,5,10,10a-hexahydro-3,5-ethenobenzo[g]quinoline-2-(1H)-one (described in Example 37) in 250 ml. of tetrahydrofuran was added slowly to a stirred suspension of 1.52 g. (0.04 mole) of lithium aluminum hydride in 108 ml. of tetrahydrofuran, and the mixture was heated under reflux for one and one half hours and then worked up in the manner described above in Example 12A. The product was isolated in the form of the hydrochloride salt which was recrystallized from ethanol/diethyl ether to give 3.08 g. of 7-methoxy-5α-methyl-1,2,3,4,4a,5,10,10a-octahydro-3,5-ethenobenzo[g]quinoline hydrochloride, m.p. 254°-255° C.

EXAMPLE 39

A solution of 18.0 g. (0.07 mole) of 7-methoxy-5α-methyl-1,2,3,4,4a,5,10,10a-octahydro-3,5-ethenobenzo[g]-quinoline hydrochloride (described in Example 38) in 200 ml. of ethanol was reduced with hydrogen over 1.8 g. of palladium-on-charcoal under a hydrogen pressure of about 55 p.s.i. When reduction was complete, the product was worked up in the manner described above in Example 3 to give 3.6 g. of 7-methoxy-5α-methyl-1,2,3,4,4a,5,10,10a-octahydro-3,5-ethanobenzo[g]quinoline, m.p. 82°-84° C. (from hexane).

EXAMPLE 40

A. A solution of 12.0 g. (0.047 mole) of 7-methoxy-5α-methyl-1,2,3,4,4a,5,10,10a-octahydro-3,5-ethenobenzo[g]quinoline hydrochloride (described in Example 38) in 60 ml. of 48% hydrobromic acid was refluxed and stirred for 15 minutes, then cooled and worked up in the manner described above in Example 19A. The product was isolated in the form of the free base to give 5.7 g. of 7-hydroxy-5α-methyl-1,2,3,4,4a,5,10,10a-octahydro-3,5-ethenobenzo[g]quinoline, m.p. 298°–310° C. (from DMF);

B. Following a procedure similar to that described in Example 40A, 12.5 g. (0.049 mole) of 7-methoxy-5α-methyl-1,2,3,4,4a,5,10,10a-octahydro-3,5-ethanobenzo[g]quinoline (described in Example 39) was reacted with 62 ml. of 48% hydrobromic acid, and the product, in the form of the hydrobromide salt, was recrystallized from water to give 5.6 g. of 7-hydroxy-5α-methyl-1,2,3,4,4a,5,10,10a-octahydro-3,5-ethanobenzo[g]quinoline hydrobromide, m.p. 305°–311° C.

EXAMPLE 41

A. A mixture of 4.8 g. (0.02 mole) of 7-hydroxy-5α-methyl-1,2,3,4,4a,5,10,10a-octahydro-3,5-ethenobenzo[g]-quinoline (described in Example 40A), 1.7 g. (0.02 mole) of sodium bicarbonate and 1.9 ml. (0.022 mole) of allyl bromide in 50 ml. of DMF was heated with stirring under reflux for one hour and then worked up in the manner described above in Example 7A. The product was isolated in the form of the hydrochloride salt which was recrystallized from ethanol/diethyl ether to give 2.6 g. of 1-allyl-7-hydroxy-5α-methyl-1,2,3,4,4a,5,10,-10a-octahydro-3,5-ethenobenzo[g]quinoline hydrochloride, m.p. 246°–248° C.

Following a procedure similar to that described in Example 41A, using the 7-hydroxy-5α-methyl-1,2,3,4,4a,5,10,10a-octahydro-3,5-ethenobenzo[g]quinoline or the 7-hydroxy-5α-methyl-1,2,3,4,4a,5,10,10a-octahydro-3,5-ethanobenzo[g]quinoline described in Examples 40A and 40B, respectively, and an appropriate alkylating agent, $R_1Hal$, there are prepared the corresponding 1-$R_1$-7-hydroxy-5α-methyl-1,2,3,4,4a,5,10,-10a-octahydro-3,5-ethenobenzo[g]quinolines and 1-$R_1$-7-hydroxy-5α-methyl-1,2,3,4,4a,5,10,10a-octahydro-3,5-ethanobenzo[g]quinolines of formulas IIIa and IIIb, respectively, in Table 41 below where, in each instance, $R_2'$, $R_2''$, $R_2'''$ and $R_3$ are hydrogen; Q is $H_2$; $R_2$ is HO; and $R_4$ is $CH_3$. The yields of products and the melting points are given, in each case, for the hydrochloride salts unless noted otherwise. The nature of the starting material and final product, whether the 3,5-etheno compounds of formula IIIa or the 3,5-ethano compounds of formula IIIb, is indicated by the designations IIIa and IIIb, respectively.

TABLE 41

| Example | $R_1$ | Wt. S.M. | Wt. Prod. | m.p. (°C.) | Solvent |
|---|---|---|---|---|---|
| 41B (IIIa) | $C_6H_5CH_2CH_2$ | 4.82 (base) | 5.4 | 190–192 | ethanol/ether |
| 41C (IIIb) | $CH_2=CHCH_2$ | 6.5 (HBr) | 5.3 | 238–241 | ethanol/ether |
| 41D (IIIb) | $C_6H_5CH_2CH_2$ | 6.49 (HBr) | 5.1 | 259–262 | ethanol |
| 41E (IIIa) | $C_3H_7$ | 4.82 (base) | 3.8[a] | 210–211[a] | $CH_3CN$/ether |
| 41F (IIIb) | $C_3H_5$—$CH_2$[b] | 6.49 (HBr) | 2.5 | 252 | ethanol/ether |
| 41G (IIIb) | $C_3H_7$ | 6.49 (HBr) | 3.1 | 260–264 | ethanol/ether |
| 41H (IIIa) | $C_3H_5$—$CH_2$[b] | 4.82 (base) | 2.6 | 251–253[c] | ethanol/ether |

[a] Methanesulfonate salt
[b] Cyclopropylmethyl
[c] Hydrobromide

EXAMPLE 42

A. A mixture of 4.82 g. (0.02 mole) of 7-hydroxy-5α-methyl-1,2,3,4,4a,5,10,10a-octahydro-3,5-ethenobenzo[g]quinoline (described in Example 40A), 1.6 ml. (0.02 mole) of 37% aqueous formaldehyde and 100 ml. of ethanol was reduced with hydrogen over 2 g. of palladium-on-charcoal using a Parr-shaking apparatus. When reduction was complete, the mixture was worked up in the manner described above in Example 3 and the product isolated in the form of the hydrochloride salt to give 3.6 g. of 1,5α-dimethyl-7-hydroxy-1,2,3,4,4a,5,10,-10a-octahydro-3,5-ethenobenzo[g]quinoline hydrochloride, m.p. 302°–305° C. (from ethanol/diethyl ether);

B. Following a procedure similar to that described in Example 42A, a mixture of 6.49 g. (0.02 mole) of 7-hydroxy-5α-methyl-1,2,3,4,4a,5,10,10a-octahydro-3,5-ethanobenzo[g]quinoline hydrobromide (described in Example 40B), 1.6 ml. (0.02 mole) of 37% aqueous formaldehyde and 2.8 ml. (0.02 mole) of triethylamine in 100 ml. of ethanol was reduced with hydrogen over 2 g. of palladium-on-charcoal and the product isolated in the form of the hydrochloride salt to give 2.8 g. of 1,5α-dimethyl-7-hydroxy-1,2,3,4,4a,5,10,10a-octahydro-3,5-ethanobenzo[g]quinoline hydrochloride, m.p. 318° C. (from water).

BIOLOGICAL TEST RESULTS

The compounds of formula I are generally active in the acetylcholine-induced abdominal constriction test (Ach), a primary analgesic screening test, and also in either the rat tail flick radiant thermal heat analgesic test (Tail Flick Agon.) or the rat tail flick phenazocine antagonist test. Some of the species have also been tested and found active in the phenyl-p-quinone-induced writhing (PPQ) and anti bradykinin (BK) tests, which are also primary analgesic screening procedures.

Data so obtained from the compounds, identified by reference to the preceding examples and expressed either in terms of the $ED_{50}$ (mg./kg., subcutaneous administration) or in terms of percent inhibition, are given below. Where more than one form of a given species has been described in the examples, such as the free base, or a particular salt form or a d- or l-form, if resolution into optical isomers was carried out, the compounds are so-identified along with the example number.

The finding of inactivity in a given test is indicated by the letter I. All doses are expressed in milligrams per kilogram (mg./kg.).

| Example | Ach | Phen. | PPQ | BK | Tail Flick Agonist |
|---|---|---|---|---|---|
| 18A | 1.7 | I | — | — | 14 ± 2 |
| 18B | 0.3 | I | — | — | 6.9 ± 0.8 |
| 18C | 1.1 | — | — | — | 11 ± 1.0 |
| 18D | 7.4 | 24 | 64%/50 | — | I |
| 18H | 18 | I | — | 40%/10 | I/240 |
| 18M | 1.9 | I | — | — | 5.9 ± 0.95 |
| 18N | 0.89 | I | — | — | 2.0 ± 0.22 |
| 18P | 87%/75 33%/25 | 7.8 | — | — | I |
| 18Q | ~6.9 | I | — | — | 16%/120 14%/10 |
| 18S | 1.0 | I | — | — | 4.3 ± 0.52 |
| 18U | 53%/75 43%/25 7%/7.5 | I | — | — | I |
| 18V | 2.0 | I | — | 2.4 | 16 ± 3.3 |
| 18W | 60%/75 20%/25 | I | — | — | I |
| 18Y | 0.63 | I | — | — | 1.35 |
| 18Z | 11 | 21 | — | — | I |
| 18AA, 34B | 3.5 | — | — | — | 66%/120 |
| 18AB, 34D | 1.9 | I/80 | — | — | 16 |
| 18AC, 34F | ~1.3 | I/80 | — | — | 15 |
| 18AD, 34H | 11 | I/80 | — | — | 13%/120 |
| 18AE, 34L | 1.2 | I/80 | — | — | 31 |
| 18AF, 34K | 7.5 | I/80 | — | — | 70%/120 |
| 18AG, 34A | 1.3 | I/80 | — | — | 9.4 |
| 18AH | ~0.71 | I/1.0 | — | — | 2.6 |
| 18AJ, 34N | 10 | 26%/80 | — | — | 33%/240 12%/120 |
| 18AK, 34P (H$_2$SO$_4$) | 5.6 | I/80 | — | 28 | 16%/120 |
| 18AK (base) | 60%/75 47%/25 33%/10 | I/80 | — | — | I/240 |
| 18AL, 31A | ~0.22 | I/10 | — | — | 0.86 |
| 18AM, 34Q | 0.081 | I/10 | — | — | 0.28 |
| 18AN, 34R | 0.025 | I/0.1 | — | — | 0.18 |
| 18AP, 34S | 0.24 | I/0.1 | — | — | 0.46 |
| 18AQ, 34T | 0.90 | I/0.1 | — | — | 1.5 |
| 19B | 1.4 | I | — | 0.24 | 42 ± 21 |
| 19C | ~0.18 | I | — | — | 0.99 ± 0.14 |
| 19D | 0.023 | I | — | — | 0.099 ± 0.014 |
| 19E | 0.19 | I | — | — | 0.95 ± 0.11 |
| 19F(d,l-HCl) | 0.074 | 0.30 | 0.018 | 0.032 | 47%/240 |
| 19F(d-HCl) | 13%/10 27%/1.0 27%/0.5 | I | — | — | I |
| 19F(l-HCl) | 0.016 | ~0.088 | — | — | 9%/120 |
| 19F(d,l-CH$_3$SO$_3$H) | 0.049 | — | — | — | — |
| 19G | 12 | 0.04 | — | 2.2 | 16 |
| 19H(d,l-HCl) | 0.24 26(p.o) | 0.008 7.8(p.o.) | 0.28 | 0.043 | I |
| 19H(d,l-CH$_3$SO$_3$H) | 0.23 | — | — | — | — |
| 19H(l-CH$_3$SO$_3$H) | 0.74 0.19 | 0.005 | 0.052 | 0.022 | I/95 |
| 19H(d-CH$_3$SO$_3$H) | 6.3 ~11 | I/80 | 5.6 | I/50 | I/85 |
| 19H(napsylate) | 0.10 | ~2(i.p.) | — | — | — |
| 19J | 0.019 | I | — | — | 0.067 |
| 19K | 0.24 | I | — | — | 1.5 |
| 19L | 8.1 | 0.015 | — | 0%/10,50 | I |
| 19M(base) | 0.25 | — | — | 100%/0.5 | 70%/60 |
| 19M(CH$_3$SO$_3$H) | 0.17 | — | 0.21 | 0.19 | 2.5 |
| 19N | 4.2 | 0.42 | — | — | I/120 |
| 19R | 5.3 | 0.029 | — | — | I/120 |
| 19S | 0.15 | 1.1 | — | — | 13%/120 |
| 19U | 0.066 | 0.86 | — | — | 59%/120 36%/60 19%/30 |
| 19V | 60%/75 47%/25 | 0.012 | — | 0%/25 | I/100 |
| 19W | 0.0012 | — | — | — | 0.00135 |
| 19X | 0.0036 | I/0.001 | — | — | 0.0046 |
| 19Y | 0.011 | I/0.01 | — | — | 0.028 |
| 19Z | 1.3 | ~0.004 | — | 0.28 | I/120 |
| 19AA | 8.2 | 0.0052 | — | — | I/120 |

-continued

| Example | Ach | Phen. | PPQ | BK | Tail Flick Agonist |
|---|---|---|---|---|---|
| 20C | 13 | I | — | I/50<br>100%/50(i.p.) | 40%/60(i.p.) |
| 20D | 2.7 | I | — | — | 25%/30 |
| 20G(HCl) | 13%/25<br>13%/2.5 | I | — | — | 40%/120(i.p.)<br>33%/60(i.p.) |
| 20G(base) | 8.9 | I/80 | — | — | I/120 |
| 20H | 100%/75<br>27%/25 | I | — | — | I |
| 21A | 8.9 | 0.088 | — | — | I/120 |
| 21C | 6.9 | I | — | — | 64 ± 12 |
| 21D | 5.4 | I | — | — | 17%/120<br>64%/240 |
| 21E(HCl) | 1.5 | I | — | — | 30 ± 7.4 |
| 21F | 13%/75<br>7%/125 | I | — | — | I |
| 21H | 7%/75<br>13%/25 | I | — | — | I |
| 21J | 87%/75<br>47%/25 | 0.013 | — | — | I/120 |
| 21K | 7.5 | 0.037 | — | — | I/120 |
| 21L | 27%/75<br>27%/25 | 0.0078 | — | — | I/120 |
| 21M | 5.1 | 0.026 | — | — | I/120 |
| 21N | 40%/75<br>27%/25 | 0.011 | — | — | I/240 |
| 22A | 1.6 | I | — | — | 11 ± 2.2 |
| 22B | 2.1 | I | — | — | 10%/60 |
| 22C | 4.7 | 61%/80 | 11 | — | I |
| 22D | 16 | 0.046 | 21 | 40%/100<br>25%/50<br>40%/10 | I |
| 22F | 8.2 | I | 5.9 | — | I |
| 22S | 3.9 | I/10 | — | I/10 | — |
| 25A | 2.8 | I | — | — | 60 ± 6.9 |
| 26A | 93%/75<br>33%/25<br>27%/10 | 0.27 | — | — | — |
| 26B | 40%/75<br>27%/25 | I | — | — | I |
| 26C | 2.6 | I | — | — | 68 ± 14 |
| 26D | 67%/75<br>33%/25<br>13%/1.0 | 0.022 | — | — | I |
| 26E | 7.6 | 0.019 | — | — | I |
| 26F | 34 | 0.47 | — | — | I |
| 26G(d,l-CH$_3$SO$_3$H) | 8.9 | 0.71 | — | I/28 | I |
| 26G(l-CH$_3$SO$_3$H) | 3.8 | 0.34 | — | — | I |
| 26H | 100%/75<br>47%/25 | I | — | — | I |
| 26J | 3.8 | 2.3 | — | 7.9 | I |
| 26K | 0.017 | I | — | 0.012 | 0.039 ± 0.006 |
| 26L | 6.6 | 2.4 | — | ~5 | I |
| 26M | 9.0 | 1.1 | — | — | I/15 |
| 26N | 4.5 | 0.006 | — | — | I |
| 26P | 20%/75<br>27%/25 | 0.26 | — | — | I/120(i.p.) |
| 26Q | 100%/75<br>47%/25 | 0.33 | — | — | I |
| 26R | 87%/75<br>13%/25 | I | — | — | I |
| 27 | 33%/75<br>13%/25 | 12 | — | — | I/120 |
| 28A | 6.5 | 0.025 | — | — | I |
| 28B | 7.9 | 0.040 | — | — | I |
| 28C | 3.3 | I | — | — | 17%/120<br>43%/240 |
| 29A | 2.5 | I | — | — | 56 |
| 29B | 1.4 | 26%/10(i.p.) | — | 0.70 | 15%/60(i.p.) |
| 29C | 93%/75<br>13%/25 | 0.0034 | — | — | I |
| 29D(base) | 0.023 | 0.050 | 0.034 | 0.024 | — |
| 29D(HCl) | — | — | — | 1.0(p.o) | — |
| 29E | 22 | 0.032 | — | I/100 | I/120 |
| 29F | 14 | 0.020 | — | I/50 | I/120 |
| 30B | 1.6 | I | — | — | 22%/120<br>72%/60<br>72%/30 |
| 32 | 2.0 | 0.060 | — | — | I/120 |
| 33A | 7%/75 | I | — | — | I |

-continued

| Example | Ach | Phen. | PPQ | BK | Tail Flick Agonist |
|---------|-----|-------|-----|-----|--------------------|
| 33B | 13%/25<br>7%/75<br>20%/25 | I | — | — | — |

The compounds of Examples 18D, 19P, 19F, 19G, 19H, 21A, 22D, 26A, 26G, 26J, 26L, 26M, 26N, 28A, 29C and 26P have also been found to be active in the phenazocine tail flick antagonist test, the ED$_{50}$ (subcutaneous administration) for those species being, respectively, 24, 7.8, ~0.58, 0.040, 0.008 (0.098 vs. morphine), 0.088, 0.046, 0.27, 0.71, 2.3, 2.4, 1.1, 0.006, 0.025, 0.0034 and 0.26 mg./kg. The compounds of formulas IIIa and IIIb are generally active in the same primary analgesic screening test, the acetylcholine-induced abdominal constriction and the phenyl-p-quinone-induced writhing tests. Data so obtained are given below, all doses being expressed in mg./kg.

| Example/Formula | Ach | PPQ |
|-----------------|-----|-----|
| 35A/IIIa | 2.7 | — |
| 35A/IIIb | 17 | — |
| 35B/IIIa | 1.6 | 20 |
| 35C/IIIa | 4.1 | 36 |
| 37/IIIa | Inact. | — |
| 38/IIIa | 4.6 | 17 |
| 39/IIIb | 5.1 | 13 |
| 40A/IIIa | 3.5 | Inact. |
| 41A/IIIa | 11 | — |
| 41B/IIIa | 1.4 | 10 |
| 41C/IIIb | 12 | Inact. |
| 41D/IIIb | 16 | Inact. |
| 41E/IIIa | 4.5 | — |
| 41F/IIIb | 3.2 | 100%/70<br>43%/35 |
| 41G/IIIb | 13 | 43 |
| 42A/IIIa | 1.9 | 23 |
| 42B/IIIb | 3.0 | 23 |

Finally, certain species of formula II have been found active in the acetylcholine-induced abdominal constriction test and the anti-bradykinin test, both of which are primary analgesic screening tests, thus indicating usefulness of these species as analgesics, in addition to their usefulness as intermediates for the preparation of the products of formulas I and IIIa. The data so-obtained on subcutaneous administration expressed either in terms of the ED$_{50}$'s or the percent inhibition for the acetylcholine constriction test or in terms of the percent protection of the pain response elicited by intraarterial bradykinin injection (the anti-bradykinin test) are given below.

| Example | Ach | BK |
|---------|-----|-----|
| 5B | 33%/75<br>13%/25 | — |
| 5C | 8.6 | 20%/10<br>20%/100 |
| 5D | 87%/75<br>27%/25 | — |
| 6D | 18 | Act. |
| 6L | 22<br>73%/150(p.o.)<br>33%/50(p.o.) | 55 |
| 6M | 19 | — |
| 6N | 100%/75<br>13%/25 | — |
| 9H | 4.4 | 40%/10<br>20%/100(Inact.) |
| 2AD | 20%/75<br>33%/25 | |
| 7R | 0%/75<br>13%/25 | — |

In addition the compound of Example 5C was found to have an ED$_{50}$(s.c.) of 36 mg./kg. in the phenyl-p-quinone-induced writhing test.

I claim:

1. A compound having one of the formulas

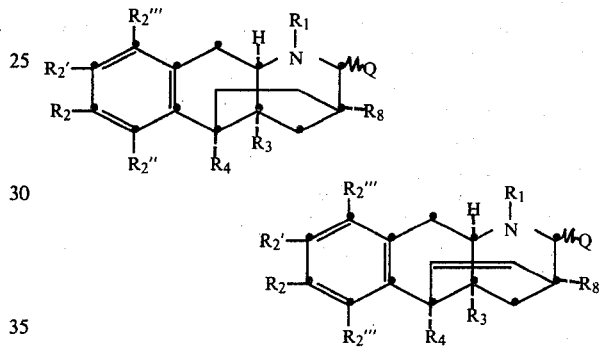

where R$_1$ is hydrogen, lower-alkyl, lower-alkanoyl (only when R$_4$ is hydrogen), lower-alkenyl, lower-alkynyl, halo-lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups, phenyl-lower-alkyl, or phenyl-lower-alkyl substituted in the phenyl ring by from one to two members of the group consisting of halogen, lower-alkyl, hydroxy, lower-alkanoyloxy, lower-alkoxy, lower-alkylmercapto, trifluoromethyl, amino, lower-alkanoylamino or a single methylenedioxy attached to adjacent carbon atoms; R$_2$, R$_2'$, R$_2''$ and R$_2'''$ are each hydrogen, or three of them are hydrogen and the fourth is halogen, lower-alkyl, hydroxy, lower-alkanoyloxy, lower-alkoxy, lower-alkylmercapto, trifluoromethyl, nitro, amino, lower-alkanoylamino, lower-alkoxycarbonylamino or phenyl, or two of the adjacent such groups together are methylenedioxy; R$_3$ is hydrogen or lower-alkyl; R$_4$ is hydrogen, lower-alkyl, lower-alkoxy-lower-alkyl, hydroxy-lower-alkyl, lower-alkylthio-lower-alkyl, lower-alkylsulfinyl-lower-alkyl, phenylthio-lower-alkyl, phenylsulfinyl-lower-alkyl, lower-alkenyl or halo-lower-alkyl, or R$_3$ and R$_4$ together are divalent lower-alkylene, —(CH$_2$)$_n$—, where n is one of the integers 3 or 4; and Q is oxo, H$_2$, CH-lower-alkyl, CH-cycloalkyl, CH-lower-alkylcycloalkyl, CH-phenyl or CH-lower-alkylphenyl, or the latter two groups substituted in the phenyl ring by from one to two members of the group consisting of lower-alkyl, lower-alkoxy, lower-alkylmercapto, trifluoromethyl or methylenedioxy attached to adjacent carbon atoms; R$_8$ is hydrogen or lower-alkyl; or an acid addition salt thereof.

2. A compound having one of the formulas

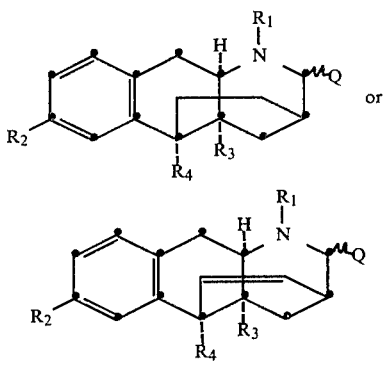

where $R_1$ is hydrogen, lower-alkyl, lower alkenyl, cycloalkyl-lower-alkyl, 2- or 3-furylmethyl, or such 2- or 3-furylmethyl substituted on the unsubstituted ring carbon atoms by from one to three methyl groups, or phenyl-lower-alkyl; $R_2$ is hydrogen, hydroxy or lower-alkoxy; $R_3$ is hydrogen or lower-alkyl; $R_4$ is lower-alkyl or lower-alkoxy-lower-alkyl or $R_3$ and $R_4$ together are divalent lower-alkylene, $-(CH_2)_n-$, where n is one of the integers 3 or 4; and Q is oxo, $H_2$ or CH-lower-alkyl or an acid addition salt thereof.

3. A compound according to claim 2 where Q is $H_2$.

4. A compound according to claim 2 where Q is CH-lower-alkyl.

5. A compound according to claim 2 wherein Q is oxo.

6. 7-Methoxy-5α-methyl-1,2,3,4,4a,5,10,10a-octahydro-3,5-ethenobenzo[g]quinoline according to claim 3.

7. 7-Methoxy-5α-methyl-1,2,3,4,4a,5,10,10a-octahydro-3,5-ethanobenzo[g]quinoline according to claim 3.

8. 7-Hydroxy-5α-methyl-1,2,3,4,4a,5,10,10a-octahydro-3,5-ethenobenzo[g]quinoline according to claim 3.

9. 1-Allyl-7-hydroxy-5α-methyl-1,2,3,4,4a,5,10,10a-octahydro-3,5-ethenobenzo[g]quinoline according to claim 3.

10. 1-(2-Phenylethyl)-7-hydroxy-5α-methyl-1,2,3,4,4a,5,10,10a-octahydro-3,5-ethenobenzo[g]quinoline according to claim 3.

11. 1-Allyl-7-hydroxy-5α-methyl-1,2,3,4,4a,5,10,10a-octahydro-3,5-ethanobenzo[g]quinoline according to claim 3.

12. 7-Hydroxy-5α-methyl-1-(2-phenylethyl)-1,2,3,4,4a,5,10,10a-octahydro-3,5-ethanobenzo[g]quinoline according to claim 3.

13. 7-Hydroxy-5α-methyl-1-propyl-1,2,3,4,4a,5,10,-10a-octahydro-3,5-ethenobenzo[g]quinoline according to claim 3.

14. 1-Cyclopropylmethyl-7-hydroxy-5α-methyl-1,2,3,4,4a,5,10,10a-octahydro-3,5-ethanobenzo[g]quinoline according to claim 3.

15. 7-Hydroxy-5α-methyl-1-propyl-1,2,3,4,4a,5,10,-10a-octahydro-3,4-ethanobenzo[g]quinoline according to claim 3.

16. 1,5α-Dimethyl-7-hydroxy-1,2,3,4,4a,5,10,10a-octahydro-3,5-ethenobenzo[g]quinoline according to claim 3.

17. 1,5α-Dimethyl-7-hydroxy-1,2,3,4,4a,5,10,10a-octahydro-3,5-ethanobenzo[g]quinoline according to claim 3.

18. 1,2-Dimethyl-5α-ethyl-1,2,3,4,4a,5,10,10a-octahydro-3,5-ethenobenzo[g]quinoline according to claim 4.

19. 1,2-Dimethyl-5α-ethyl-1,2,3,4,4a,5,10,10a-octahydro-3,5-ethanobenzo[g]quinoline according to claim 4.

20. 5α-Ethyl-1,2,4aα-trimethyl-1,2,3,4,4a,5,10,10a-octahydro-3,5-ethenobenzo[g]quinoline according to claim 4.

21. 1-Cyclopropylmethyl-5α-ethyl-2-methyl-1,2,3,4,4a,5,10,10a-octahydro-3,5-ethenobenzo[g]quinoline according to claim 4.

22. 7-Methoxy-5α-methyl-3,4,4a,5,10,10a-hexahydro-3,5-ethenobenzo[g]quinoline-2-(1H)-one according to claim 5.

23. A compound having one of the formulas

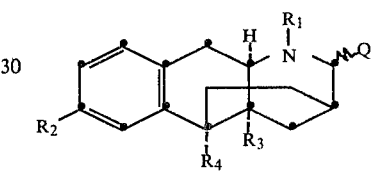

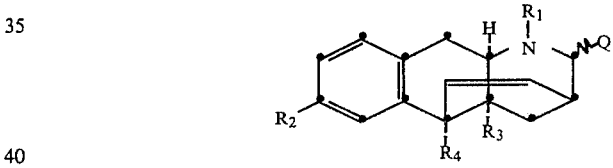

where $R_1$ is hydrogen, lower-alkyl, lower-alkenyl, cycloalkyl, cycloalkyl-lower-alkyl, 2- or 3-furylmethyl, or such 2- or 3-furylmethyl substituted on the unsubstituted ring carbon atoms by from one to three methyl groups or phenyl-lower-alkyl; $R_2$ is hydrogen, hydroxy or lower-alkoxy; $R_3$ is hydrogen or lower-alkyl; $R_4$ is lower-alkyl or lower-alkoxy-lower-alkyl, or $R_3$ and $R_4$ together are divalent lower-alkylene, $-(CH_2)_n-$, where n is one of the integers 3 or 4; and Q is CH—cycloalkyl or CH—phenyl or CH—lower-alkylphenyl substituted in the phenyl ring thereof by from one to two members of the group consisting of lower-alkyl, lower alkoxy, lower-alkylmercapto, trifluoromethyl or methylenedioxy attached to adjacent carbon atoms; or an acid addition salt thereof.

* * * * *

UNITED STATES PATENT AND TRADEMARK OFFICE
CERTIFICATE OF CORRECTION

PATENT NO. : 4,239,890

DATED : December 16, 1980

INVENTOR(S) : William F. Michne

Page 1 of 6

It is certified that error appears in the above-identified patent and that said Letters Patent are hereby corrected as shown below:

On the face page, in the third line of the paragraph headed "Related U.S. Application Data ", change "Nov., 1976" to read --Nov. 12, 1976--.

Column 1, line 8, change "Dec. 25, 1979 a continuation-in-part" to read --Dec. 25, 1979, which in turn is a continuation-in-part--.

Column 2, lines 4-5, change "($4-R_2-3-R_2''-R_2'-6-R_2'''$-benzyl)" to read --($4-R_2-3-R_2''-5-R_2'-6-R_2'''$-benzyl)--.

Column 2, line 13, change "...$3-R_1 11$..." to read --...$3-R_1-11$...--.

UNITED STATES PATENT AND TRADEMARK OFFICE
CERTIFICATE OF CORRECTION

PATENT NO. : 4,239,890

DATED : December 16, 1980

INVENTOR(S) : William F. Michne

It is certified that error appears in the above-identified patent and that said Letters Patent are hereby corrected as shown below:

Column 2, line 22, change "...$4a\alpha-5\alpha-R_4$..." to read --...$4a\alpha-R_3-5\alpha-R_4$...--.

Column 7, line 31, change "/lower-alkoxy" to read --lower-alkoxy--.

Column 13, line 35, change "and" to read --or--.

UNITED STATES PATENT AND TRADEMARK OFFICE
CERTIFICATE OF CORRECTION

PATENT NO. : 4,239,890
DATED : December 16, 1980  Page 3 of 6
INVENTOR(S) : William F. Michne It is certified that error appears in the above-identified patent and that said Letters Patent are hereby corrected as shown below:

Column 15, lines 1-10, change formula II which appears as:

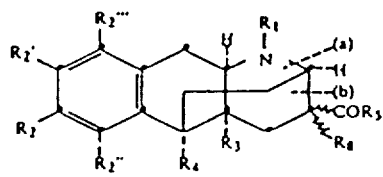

to appear as:

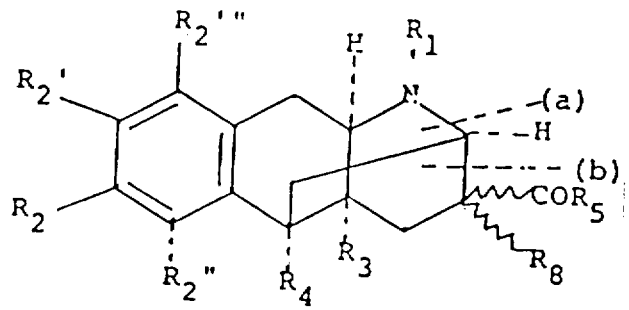

UNITED STATES PATENT AND TRADEMARK OFFICE
CERTIFICATE OF CORRECTION

PATENT NO. : 4,239,890
DATED : December 16, 1980
INVENTOR(S) : William F. Michne It is certified that error appears in the above-identified patent and that said Letters Patent are hereby corrected as shown below:

Column 15, lines 50-57, change formula IX which appears as:

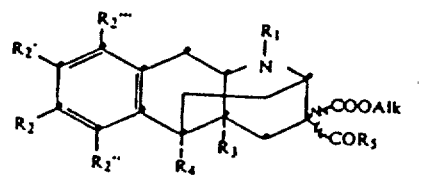

to appear as:

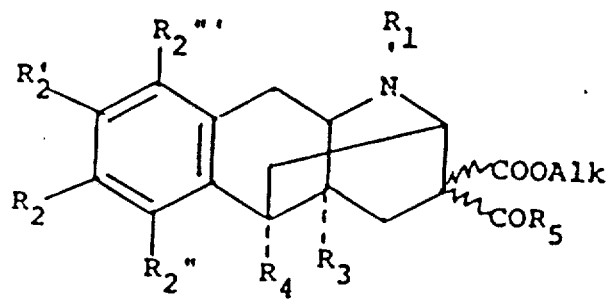

UNITED STATES PATENT AND TRADEMARK OFFICE
CERTIFICATE OF CORRECTION

PATENT NO. : 4,239,890

DATED : December 16, 1980

INVENTOR(S) : William F. Michne

It is certified that error appears in the above-identified patent and that said Letters Patent are hereby corrected as shown below:

Column 15, lines 57-65, change formula I which appears as:

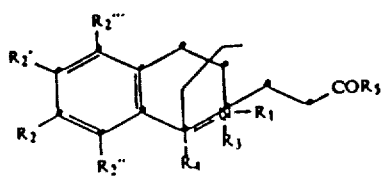

to appear as:

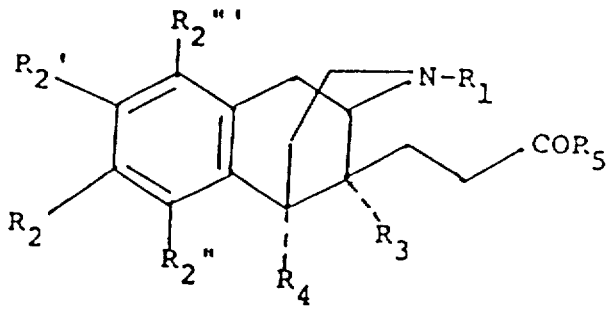

UNITED STATES PATENT AND TRADEMARK OFFICE
CERTIFICATE OF CORRECTION

PATENT NO. : 4,239,890
DATED : December 16, 1980
INVENTOR(S) : William F. Michne It is certified that error appears in the above-identified patent and that said Letters Patent are hereby corrected as shown below:

Column 19, lines 9-10, change "compound" to read --compounds--.

Column 22, line 4, change "structure" to read --structures--.

Signed and Sealed this

Third Day of January 1984

[SEAL]

Attest:

Attesting Officer

GERALD J. MOSSINGHOFF
Commissioner of Patents and Trademarks